(12) United States Patent
Hudkins et al.

(10) Patent No.: US 6,306,849 B1
(45) Date of Patent: Oct. 23, 2001

(54) SELECTED DERIVATIVES OF K-252A

(75) Inventors: Robert L. Hudkins, Chester Springs; John P. Mallamo, Glen Moore, both of PA (US); Masami Hamano, Zama (JP); Reiko Tanaka, Tokyo (JP); Chikara Murakata, Shizuoka (JP)

(73) Assignee: Cephalon, Inc., West Chester, PA (US)

( * ) Notice: Subject to any disclaimer, the term of this patent is extended or adjusted under 35 U.S.C. 154(b) by 0 days.

(21) Appl. No.: 08/867,084

(22) Filed: Jun. 2, 1997

Related U.S. Application Data

(63) Continuation-in-part of application No. 08/657,366, filed on Jun. 3, 1996.

(51) Int. Cl.[7] ................................................ A01N 43/00
(52) U.S. Cl. ...................... 514/211.01; 514/211; 514/279
(58) Field of Search ............................. 540/545; 548/416, 548/417; 514/211, 229, 211.01–211.15, 213.01–214.01

(56) References Cited

U.S. PATENT DOCUMENTS

| 4,554,402 | 11/1985 | Hawkins et al. . |
| 4,735,939 | 4/1988 | McCoy et al. . |
| 4,816,450 | 3/1989 | Bell et al. . |

(List continued on next page.)

FOREIGN PATENT DOCUMENTS

| A-17571/88 | 12/1988 | (AU) . |
| 0 238 011 A2 | 9/1987 | (EP) . |
| 0 296 110 A3 | 12/1988 | (EP) . |

(List continued on next page.)

OTHER PUBLICATIONS

Hirata et al., "K–252 Derivatives as Protein C inhibitors, Their Preparation and Formulations Containing Them", Chemical Abstracts 111:728, XP00204135 see abstract and 12th Collective Chemical Substance Index, p. 34237, c. 3 (5–7), 55–60, 66–69), p. 34238, c.1 (41–44), c.2 (25–27, 32–33), p. 3423, c.3 (48–50, 52–53).

Abe et al., "Arachidonic Acid Metabolism in Ischemic Neuronal Damage," *Annals of the New York Academy of Sciences* 559:259–268 (1989).

Borasio, "Differential effects of the protein kinase inhibitor K–252a on the in vivo survival of chick embryonic neurons," *Neuroscience Letters* 108:207–212 (1990).

(List continued on next page.)

*Primary Examiner*—Laurie Scheiner
*Assistant Examiner*—J. S. Parkin
(74) *Attorney, Agent, or Firm*—Woodcock Washburn Kurtz Mackiewicz & Norris LLP

(57) ABSTRACT

Disclosed herein are selected indolocarbazole derivatives which are represented by the general formula:

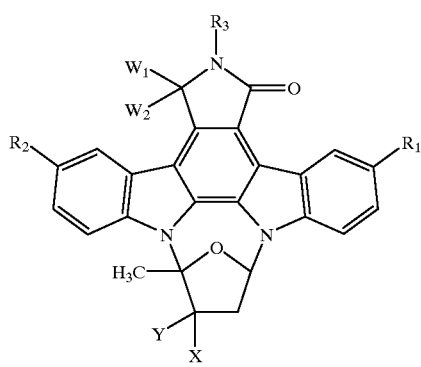

The compounds are useful for enhancing the function and/or survival of a trophic factor responsive cell. They inhibit interleukin-2 production and have immunosuppressive activity.

4 Claims, 3 Drawing Sheets

| Compd | R$^1$ | R$^2$ | R$^3$ | Y |
|---|---|---|---|---|
| a | CHO | CHO | Ac | OAc |
| b | CHO | H | Ac | OAc |
| c | H | H | Ac | OAc |

U.S. PATENT DOCUMENTS

| | | |
|---|---|---|
| 4,877,776 | 10/1989 | Murakata et al. . |
| 4,923,986 | 5/1990 | Murakata et al. . |
| 5,043,335 | 8/1991 | Kleinschroth et al. . |
| 5,093,330 | 3/1992 | Caravatti et al. . |
| 5,344,926 | 9/1994 | Murakata et al. . |
| 5,461,145 | 10/1995 | Kudo et al. . |
| 5,461,146 | 10/1995 | Lewis et al. ............... 540/545 |
| 5,468,872 | 11/1995 | Glicksman et al. ............ 548/416 |
| 5,516,771 | 5/1996 | Dionne et al. . |
| 5,516,772 | 5/1996 | Glicksman et al. ............ 514/211 |
| 5,621,100 | 4/1997 | Lewis et al. . |

FOREIGN PATENT DOCUMENTS

| | | |
|---|---|---|
| 0 323 171 A3 | 7/1989 | (EP) . |
| 0 370 236 A1 | 5/1990 | (EP) . |
| 0 558 962 A1 | 9/1993 | (EP) . |
| 0 630 898 A1 | 12/1994 | (EP) . |
| 62120388 | 6/1987 | (JP) . |
| 62155284 | 7/1987 | (JP) . |
| 62155285 | 7/1987 | (JP) . |
| 63295588 | 12/1988 | (JP) . |
| 63295589 | 12/1988 | (JP) . |
| 5086068 | 4/1993 | (JP) . |
| 5247055 | 9/1993 | (JP) . |
| 6073063 | 3/1994 | (JP) . |
| WO 88/07045 | 9/1988 | (WO) . |
| WO 89/07105 | 8/1989 | (WO) . |
| WO 91/09034 | 6/1991 | (WO) . |
| WO 93/08809 | 5/1993 | (WO) . |
| WO 94/02488 | 2/1994 | (WO) . |
| WO 95/00520 | 1/1995 | (WO) . |

OTHER PUBLICATIONS

Bozyczko–Coyne et al., "A rapid fluorometric assay to measure neuronal survial in vivo," *Journal of Neuroscience Methods* 50:205–216 (1993).

Tischler et al., "A Protein Kinase Inhibitor, Staurosporine, Mimics Nerve Growth Factor Induction of Neurotensin/Neuromedin N Gene Expression," *The Journal of Biological Chemistry* 266:1141–1146 (1991).

Vitullo, Press Release "Cephalon and Kyowa Hakko Co., Ltd. Announce Collaboration," Jun. 2, 1992.

Wolf et al., "The Protein Kinase Inhibitor Staurosporine, Like Phorbol Esters, Induces the Association of Protein Kinase C With Membranes," *Biochem. and Biophys. Research Communication* 154:1273–1279 (1988).

Wenk, G. et al., "Nucleus *basalis magnocellularis*: optimal coordinates for selective reduction of choline acetyltransferase in frontal neocortex by ibotenic acid injections," *Exp. Brain Res.* 56:335–340 (1984).

Chiu, A. et al., "A Motor Neuron–Specific Epitope and the Low Affinity Nerve Growth Factor Receptor Display . . . Development , Axotomy, and Regeneration," *Journal of Comparative Neurology* 328:351–363 (1993).

Chu–Wang et al., "Cell Death of Motoneurons in the Chick Embryo Spinal Cord," *J. Comp. Neur.*, 177:33–58.

Davis et al., "Inhibitors of Protein Kinase C.1[1] 2,3–Bisarylmaleimides," *J. Med. Chem.* 35:177–184, 1992.

Davis et al., "Potent Selective Inhibitors of Protein Kinase C," *FEBS Letters* 259:61–63 (1989).

Dunnett S. et al., "The basal forebrain—cortical cholinergic system: interpeting the functional consequences of excitotoxic lesions," *TINS* 14:494–501 (1991).

Fibiger, H., "Cholinergic mechanisms in learning, memory and dementia: a review of recent evidence," *TINS* 14:220–223 (1991).

Glicksman, M. et al., "K–252a and Staurosporine Promote Choline Acetyltransference Activity in Rat Spinal Cord Cultures," *Journal of Neurochemistry* 61:210–221 (1993).

Glicksman, M. "K–252a Molecules as Promoters . . . ", Third Int. Conference on Nerve Growth Factor (NGF) and related molecule, Chateau Lake Louise, Lake Louise, Alberta, Apr.–May 1, 1994.

Glicksman, M. et al., "K–252a Promotes Survival of Striatal Neurons in Culture," *Society of Neuroscience Abstracts* 19:680 (1993).

Hamburger, "Cell Death in the Development of the Lateral Motor Column of the Chick Embryo," *J. Comp. Neur* 160:535–546 (1975).

Hara et al., "Staurosporine, a Novel Protein Kinase C Inhibitor, Prevents Postischemic Neuronal Damage in the Gerbil and Rat," *Journal of Cerebral Blood Flow and Metabolism* 10:646–653 (1990).

Hashimoto et al., "Staurosporine–induced Neurite Outgrowth in PC12h Cells," *Experimental Cell Research* 184:351–359 (1989).

Hashimoto, "K–252a, a Potent Protein Kinase inhibitor, Blocks Nerve Growth Factor–induced Neurite Outgrowth and Changes in the Phosphorylation of Proteins in PC12h Cells," *J. Cell Biology* 107:1531–1539.

Kase et al., "K–252a, A Protein inhibitor of Protein Kinase C From Microbial Orgin," *The Journal of Antibiotics* 39:1059–1065 (1986).

Kiyoto et al., "Staurosporine, a Potent Protein Kinase . . . Caused Ornithine Decarboxylase Induction in Isolated Mouse Epidermal Cells," *Biochem, and Biophys. Research Communications* 148:740–746 (1987).

Knüsel et al., "K–252b Selectively Potentiates Cellular Actions and trk Tyrosine Phosphorylation Mediated by Neurotrophin–3", *Journal of Neurochemistry* 59:715–722 (1992).

Knüet al., "K–252b Is a Selective and Nontoxic Inhibitor of Nerve Growth Factor Action on Cultured Brain Neurons," *Journal of Neurochemistry* 57:955–962 (1991).

Koizumi et al., "K–252a: A Specific inhibitor of the Action of Nerve Growth Factor in PC12 Cells," *The Journal of Neuroscience* 8:715–721 (1988).

Lazarovici et al., "K–252a inhibits the Increase in c–fos Transcription and the Increase in Intracellular Calcium Produced by Nerve Growth Factor in PC12 Cells," *Journal of Neuroscience Research* 23:1–8 (1989).

McManamann, J. et al., "Rescue of Motoneurons from Cell Death by a Purified Skeletal Muscle Polypeptides: Effects of the ChAT Development Factor, CDF," *Neuron* 4:891–898 (1990).

Matsuda et al., "The Effect of K–252a, A Potent Microbial Inhibitor of Protein Kinase, on Activated Cyclic Nucleotide Phosphodiesterase," *Biochem J.* 256:75–80 (1988).

Moody et al., "Synthesis of the Staurosporine Aglycon", *J. Org. Chem.* 57:2105–2114 (1992).

Morioka et al., "Staurosporine–induced Differentiation in a Human Neuroblastoma Cell Line, NB–1," *Agric. Biol. Chem.* 49:1959–1963 (1985).

Nabeshima et al., "Staurosporine, a protein kinase inhibitor, attenuates basal forebrain–lesion–induced amnesia and cholinergic neuronal deficit," *Neuroscience Letters* 122::13–16 (1991).

Nabeshima et al., "Staurosporine Facilitates Recovery from the Basal Forebrain–Lesion–Induced . . . Cholinergic Neuron in Rats," *The Journal of Pharmacology and Experimental Therapeutics* 257:562–566 (1991).

Nakadate et al., "Comparison of Protein Kinase C Functional Assays to Clarify Mechanisms of Inhibitor Action," *Biochemical Pharmacology* 37:1541–1545 (1988).

Nakanishi et al., "K–252b, c and d, Potent Inhibitors of Protein Kinase C From Microbial Origin," *The Journal of Antibiotics* 39:1066–1071 (1986).

Ohno et al., "Effect of Staurosporine, a Protein Kinase C Inhibitor, on Impairment of Working Memory in Rats Exposed ot Cerebral Ischemia," *European Journal of Pharmcology* 204:113–116 (1991).

Olton, D. et al., "Dementia: Animal Models of the Cognitive Impairments . . . Cholinergic System," *Psychopharmcology: The Third Generation of Progress*, Raven Press, NY (1987).

Oppenheim, R. et al., "Reduction of Naturally Occurring Motoneuron Death in Vivo by a Target–Derived Neurotrophic Factor," *Science* 240:919–921 (1988).

Oppenheim, "The Absense of Significant Postnatal Motoneuron Death in the Brachial and Lumbar Spinal Cord of the Rat," *Journal of Comparative Neurology*, 246:281–286 (1986).

Oppenheim, R. et al., "Cell Death of Motoneurons in the Chick Embryo Spinal Cord, VI. Reduction of Naturally Occurring Cell Death . . . Terni by Nerve Growth Factor," *Journal of Comparative Neurolgy*, 210:174–189 (1982).

Rasouly et al., "Staurosporine–Induced Neurite Outgrowth in PC12–Cells is Independent of Protein Kinase–C Inhibition," *Molecular Pharmacology* 42:35–43 (1991).

Sako et al., "Contrasting Actions of Staurosporine, a Protein Kinase C Inhibitor, on Human Neurophils and Primary Mouse Epidermal Cells," *Cancer Research* 48:4646–4650 (1988).

Shea et al., "Staurosporine–induced Morphological Differentiation of Human Neuroblastoma Cells," *Cell Biology International Reports* 15:161–167 (1991).

Shepherd, "The Synaptic Organization of the Brain" Second Edition, pp. 308–314 (Oxford University Press, New York, 1979).

Siman et al., "Excitatory Amino Acids Activate Calpain I and Induce Structural Protein Breakdown in Vivo," *Neuron* 1:279–287 (1988).

Slack et al., "Effects or Retinoic Acid and Staurosporine on the Protein Kinase C Activity and the Morphology of Two Related Human Neuroblastoma Cell Line" *Biochemica et Biophysica Acta* 1053:89–96 (1990).

Smith, G., "Animal models of Alzheimer's disease: experimental cholinergic denervation," *Brain Research Reviews* 13:103–118 (1988).

Smith et al., "Effects of a Protein Kinase C Inhibitor, K–252a, on Human Polymorphonuclear Neutrophil Responsiveness," *Biochem. and Biophys. Research Communications* 152:1497–1503 (1988).

Steglich et al., "Indole Pigments from the Fruiting Bodies of the Slime Mold *Arcyria denudata*," *Agnew. Chem. Int. Ed. Engl.* 19:459–460 (1980).

Knüsel et al., "K–252 Compounds: Modulators of Neurotrophin Signal Transduction", Journal of Neurochemistry 59:1987–1996, 1992.

Beal et al., "Alzheimer's Disease and Other Dementias", Harrison's Principles on Internal Medicine, Isselbacher et al., eds., McGraw–Hill Inc., New York, pp. 2272–2273.

Brouillet et al., "Chronic Mitochondrial Energy Impairment Produces Selective Striatal Degeneration and . . ", Proc. Natl. Acad. Sci. 92:7105–7109, 1995.

Mallamo, J.P., et al., 1992, "Conformationally restricted analogues of disoxaril: a comparison of the activity against human rhinovirus type 14 and 1A", J. Medicin. Chem. 35(25):4690–4695 (abstract provided).*

Ross, A.H., et al., 1995, "Differential biological effects of K252 kinase inhibitors are related to membrane solubility but not to permeability.", J. Neurochem. 65(6):2748–2756 (abstract provided).*

Containing Them, Chemical Abstracts 111:728, XP002041235 see abstract and 12th Collective Chemical Substance Index, p. 34237, c. 3 (5–7, 55–60, 66–69), p. 34238, c.1 (41–44), c.2 (25–27, 32–33), p. 3423, c.3 (48–50, 52–53). (No date).

* cited by examiner

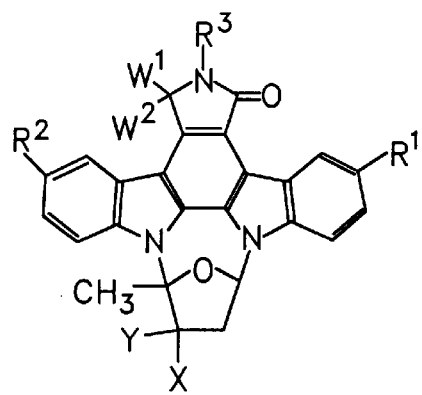 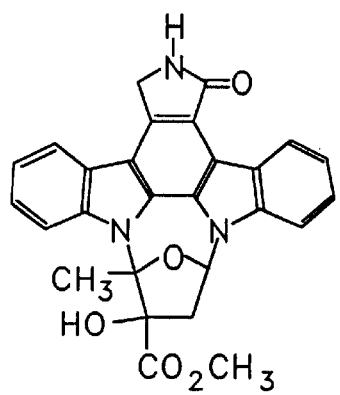
(I) FIG. 1, 3
K-252a FIG. 2
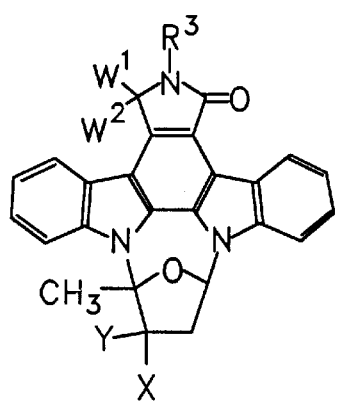 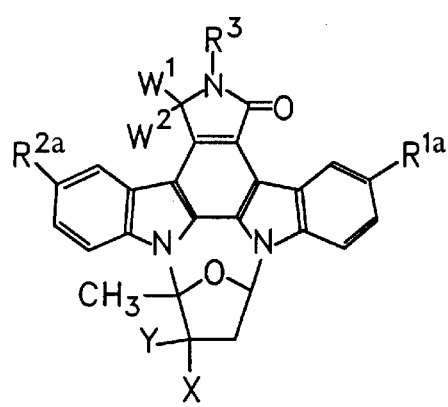
(II)     (I-1)
FIG. 4
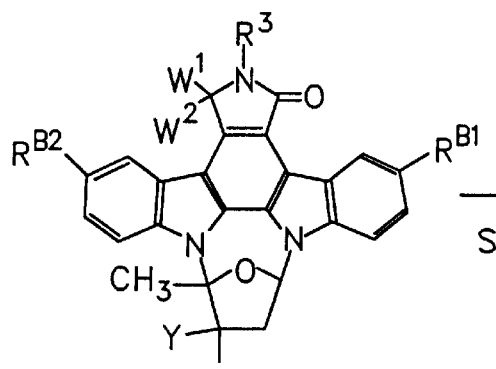 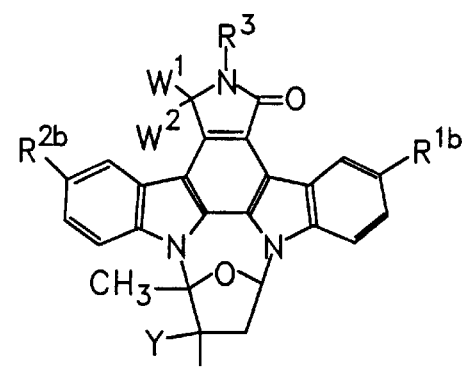
(V)     (I-2)
FIG. 5

| Compd | R¹ | R² | R³ | Y |
|-------|-----|-----|-----|-----|
| a | CHO | CHO | Ac | OAc |
| b | CHO | H | Ac | OAc |
| c | H | H | Ac | OAc |

SELECTED DERIVATIVES OF K-252A

This application is a continuation-in-part of Ser. No. 08/657,366, filed Jun. 3, 1996.

FIELD OF INVENTION

This invention features selected ring-substituted derivatives of K-252a and their use for treatment of neurological disorders.

BACKGROUND OF THE INVENTION

K-252a is a compound having an indolocarbazole skeleton represented by the following formula [Japanese Published Unexamined Patent Application No. 41489/85 (U.S. Pat. No. 4,555,402)].

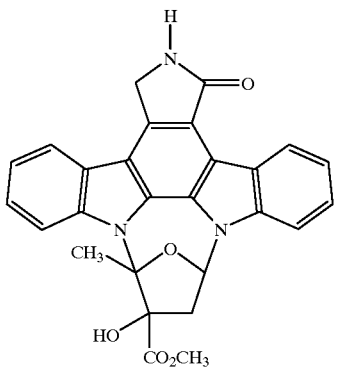

It has been reported that K-252a strongly inhibits protein kinase C (PKC) which plays a central role in regulating cell functions, and has various activities such as the action of inhibiting smooth muscle contraction (Jpn. J. Pharmacol. 43(suppl.): 284, 1987), the action of inhibiting serotonin secretion (Biochem. Biophys. Res. Commun., 144: 35, 1987), the action of inhibiting elongation of neuraxone (J. Neuroscience, 8: 715, 1988), the action of inhibiting histamine release (Allergy, 43: 100, 1988), the action of inhibiting smooth muscle MLCK (I. Biol. Chem., 263: 6215, 1988), anti-inflammatory action (Acta Physiol. Hung., 80: 423, 1992), the activity of cell survival (J. Neurochemistry, 64: 1502, 1995), etc. It has also been disclosed in Experimental Cell Research, 193: 175–182, 1991 that K-252a has the activity of inhibiting IL-2 production. Also the complete synthesis of K-252a has been achieved (J. Am. Chem. Soc., 117: 10413, 1995).

On the other hand, it has been disclosed that derivatives of K-252a have PKC inhibitory activity, the activity of inhibiting histamine release (Japanese Published Unexamined Patent Application No. 295588/88), antitumor activity [Japanese Published Unexamined Patent Application No. 168689/89 (U.S. Pat. No. 4,877,776), WO 88/07045 (U.S. Pat. No. 4,923,986)] etc., the action of increasing blood platelets [WO94/06799 (EP 630898A)], vasodepressor activity (Japanese Published Unexamined Patent Application No. 120388/87), the action of accelerating cholinergic neuron functions [WO 94/02488 (U.S. Pat. No. 5,461,146)], curative effect on prostate cancer [WO 94/27982 (U.S. Pat. No. 5,516,771)], etc.

SUMMARY OF THE INVENTION

The present invention relates to selected derivatives of K-252a represented by the general formula:

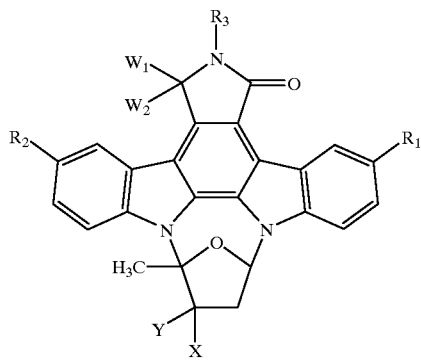

Constituent members are disclosed in detail, infra. Preferred methods for preparing these compounds and methods for using them are also disclosed.

DETAILED DESCRIPTION

I. DRAWINGS

FIGS. 1 and 3 depict the structure of the substituted K-252a derivatives of the invention.

FIG. 2 depicts the structure of K-252a.

FIG. 4 is a schematic drawing showing the synthesis of a ring-substituted K-252a derivative from a ring-unsubstituted starting material.

FIG. 5 is a schematic drawing showing the synthesis of a compound which contains at least one —CH═CH(CH$_2$)$_m$R$^{12}$ or —CH═CH(CH$_2$)$_r$R$^{18}$ ring substituent.

II. SELECTED RING-SUBSTITUTED K-252a DERIVATIVES

Figure 6:
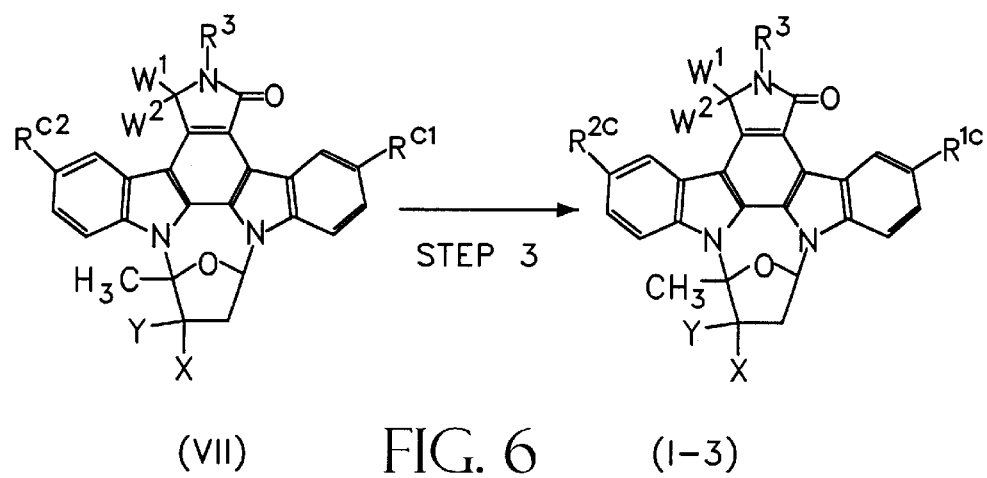
FIG. 6 is a schematic drawing showing the synthesis of a compound which contains at least one —C≡CH (CH$_2$)$_n$R$^{13}$ or —C≡CH(CH$_2$)$_u$R$^{19}$ ring substituent.
Figure 7:
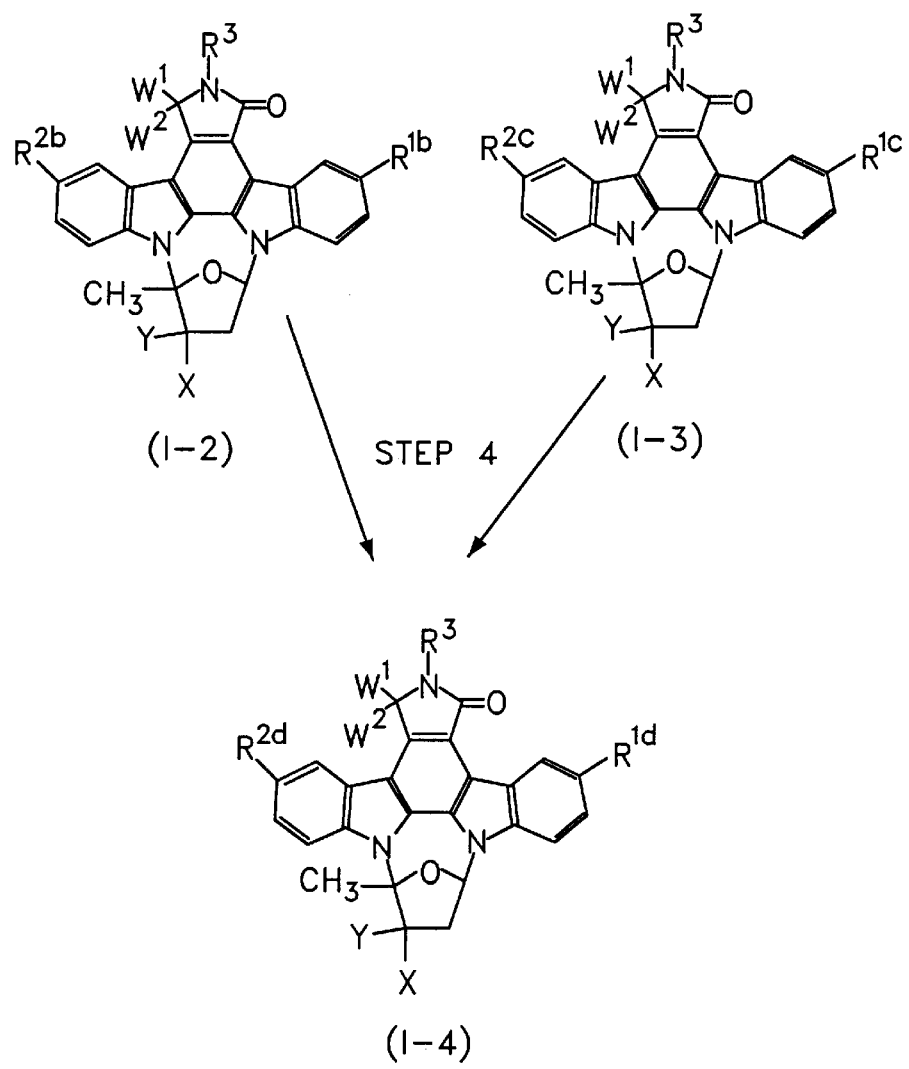
FIG. 7 is a schematic drawing showing the synthesis of a compound which contains at least one —(CH$_2$)$_k$R$^7$ or —(CH$_2$)$_t$R$^{17}$ ring substituent.
Figure 8:
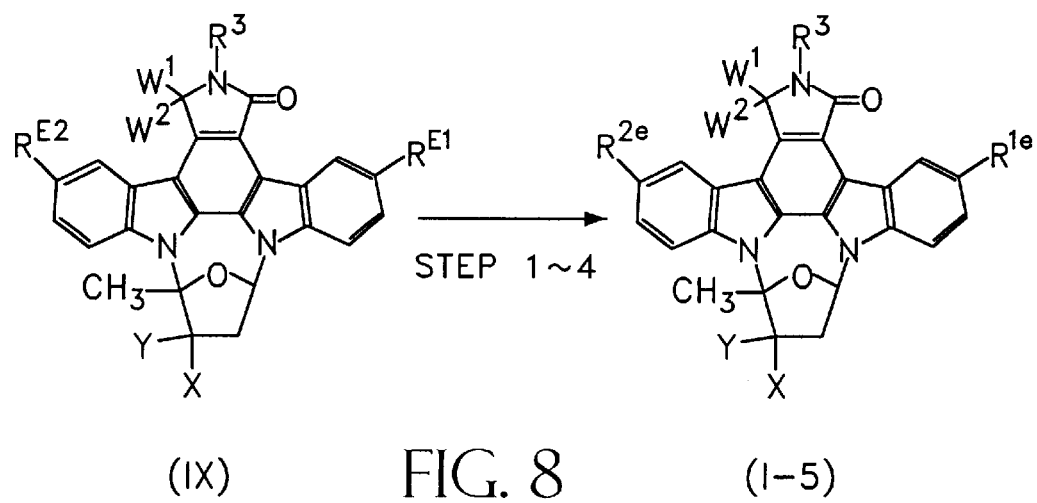
FIG. 8 is a schematic drawing showing the synthesis of a compound which contains a halogen or nitro ring substituent.

Disclosed herein are the selected ring-substituted derivatives of K-252a which are represented by the following formula:

wherein:

one of $R^1$ and $R^2$ is selected from the group consisting of:
a) —CO(CH$_2$)$_j$R$^4$, wherein j is 1 to 6, and R$^4$ is selected from the group consisting of:
 1) hydrogen and a halogen;
 2) —NR$^5$R$^6$, wherein R$^5$ and R$^6$ independently are hydrogen, substituted lower alkyl, unsubstituted lower alkyl, substituted aryl, unsubstituted aryl, substituted heteroaryl, unsubstituted heteroaryl, substituted aralkyl, unsubstituted aralkyl, lower alkylaminocarbonyl, or lower alkoxycarbonyl; or R$^5$ and R$^6$ are combined with a nitrogen atom to form a heterocyclic group;
 3) N$_3$;
 4) —SR$^{27}$, wherein R$^{27}$ is selected from the group consisting of:
  i) hydrogen;
  ii) substituted lower alkyl;
  iii) unsubstituted lower alkyl;
  iv) substituted aryl;
  v) unsubstituted aryl;
  vi) substituted heteroaryl;
  vii) unsubstituted heteroaryl;
  viii) substituted aralkyl;
  ix) unsubstituted aralkyl;
  x) thiazolinyl;
  xi) —(CH$_2$)$_a$CO$_2$R$^{28}$, wherein a is 1 or 2, and R$^{28}$ is selected from the group consisting of: hydrogen and lower alkyl; and
  xii) —(CH$_2$)$_a$CONR$^5$R$^6$; and
 5) OR$^{29}$ (wherein R$^{29}$ is hydrogen, substituted lower alkyl, unsubstituted lower alkyl, or COR$^{30}$ (wherein R$^{30}$ is hydrogen, lower alkyl, substituted aryl, unsubstituted aryl, substituted heteroaryl, or unsubstituted heteroaryl));
b) —CH(OH)(CH$_2$)$_b$R$^{4A}$, wherein b is 1 to 6 and R$^{4A}$ is hydrogen or the same as R$^4$;
c) —(CH$_2$)$_d$CHR$^{31}$CO$_2$R$^{32}$ wherein d is 0 to 5, R$^{31}$ is hydrogen, —CONR$^5$R$^6$, or —CO$_2$R$^{33}$ (wherein R$^{33}$ is hydrogen or lower alkyl), and R$^{32}$ is hydrogen or lower alkyl;
d) —(CH2)$_d$CHR$^{31}$CONR$^5$R$^6$;
e) —(CH$_2$)$_k$R$^7$ wherein k is 2 to 6, and R$^7$ is halogen, CO$_2$R$^8$ (wherein R$^8$ is hydrogen, lower alkyl, substituted aryl, unsubstituted aryl, substituted heteroaryl, or unsubstituted heteroaryl), CONR$^5$R$^6$, substituted aryl, unsubstituted aryl, substituted heteroaryl, unsubstituted heteroaryl, OR$^9$ (wherein R$^9$ is hydrogen, substituted lower alkyl, unsubstituted lower alkyl, acyl, substituted aryl, or unsubstituted aryl), SR$^{27B}$ (wherein R$^{27B}$ is the same as R$^{27}$), NR$^{10}$R$^{11}$ (wherein R$^{10}$ and R$^{11}$ are the same as R$^5$ and R$^6$) or N$_3$;
f) —CH=CH(CH$_2$)$_m$R$^{12}$ wherein m is 0 to 4, and R$^{12}$ is hydrogen, lower alkyl, CO$_2$R$^{8A}$ (wherein R$^{8A}$ is the same as R$^8$), —CONR$^5$R$^6$, substituted aryl, unsubstituted aryl, substituted heteroaryl, unsubstituted heteroaryl, OR$^{9A}$ (wherein R$^{9A}$ is the same as R$^9$), or NR$^{10A}$R$^{11A}$ (wherein R$^{10A}$ and R$^{11A}$ are the same as R$^5$ and R$^6$);
g) —CH=C(CO$_2$R$^{33A}$)$_2$, wherein R$^{33A}$ is the same as R$^{33}$;
h) —C≡C(CH$_2$)$_n$R$^{13}$, wherein n is 0 to 4, and R$^{13}$ is the same as R$^{12}$;
i) —CH$_2$OR$^{44}$, wherein R$^{44}$ is substituted lower alkyl;
and the other of R$^1$ or R$^2$ is selected from the group consisting of
j) hydrogen, lower alkyl, halogen, acyl, nitro, NR$^{14}$R$^{15}$ (wherein R$^{14}$ or R$^{15}$ is hydrogen or lower alkyl, and the other is hydrogen, lower alkyl, acyl, carbamoyl, lower alkylaminocarbonyl, substituted arylaminocarbonyl or unsubstituted arylaminocarbonyl);
k) —CH(SR$^{34}$)$_2$, wherein R$^{34}$ is lower alkyl or alkylene;
l) —CH$_2$R$^{35}$, wherein R$^{35}$ is OR$^{36}$ (wherein R$^{36}$ is tri-lower alkyl silyl in which the three lower alkyl groups are the same or different, or is the same as R$^{29}$), or SR$^{37}$ (wherein R$^{37}$ is the same as R$^{27}$);
m) —CO(CH$_2$)$_q$R$^{16}$, wherein q is 1 to 6, and R$^{16}$ is the same as R$^4$;
n) —CH(OH)(CH$_2$)$_e$R$^{38}$, wherein e is 1 to 6, and R$^{38}$ is the same as R$^{4A}$;
o) —(CH$_2$)$_f$CHR$^{39}$CO$_2$R$^{40}$, wherein f is 0 to 5, R$^{39}$ is the same as R$^{31}$ and R$^{40}$ is the same as R$^{32}$;
p) —(CH$_2$)$_r$R$^{17}$, wherein r is 2 to 6, and R$^{17}$ is the same as R$^7$;
q) —CH=CH(CH$_2$)$_t$R$^{18}$, wherein t is 0 to 4, and R$^{18}$ is the same as R$^{12}$;
r) —CH=C(CO$_2$R$^{33B}$)$_2$, wherein R$^{33B}$ is the same as R$^{33}$;
s) —C≡C(CH$_2$)$_u$R$^{19}$, wherein u is 0 to 4, and R$^{19}$ is the same as R$^{13}$);
$R^3$ is hydrogen, acyl, or lower alkyl;
X is selected from the group consisting of:
a) hydrogen;
b) formyl;
c) lower alkoxycarbonyl;
d) —CONR$^{20}$R$^{21}$, wherein:
 $R^{20}$ and $R^{21}$ independently are:
  hydrogen;
  lower alkyl;
  —CH$_2$R$^{22}$, wherein R$^{22}$ is hydroxy, or
  —NR$^{23}$R$^{24}$ (wherein R$^{23}$ or R$^{24}$ is hydrogen or lower alkyl, and the other is hydrogen, lower alky, or the residue of an α-amino acid in which the hydroxy group of the carboxyl group is excluded, or R$^{23}$ and R$^{24}$ are combined with a nitrogen atom to form a heterocyclic group); and
e) —CH=N—R$^{25}$, wherein R$^{25}$ is hydroxy, lower alkoxy, amino, guanidino, or imidazolylamino;
Y is hydroxy, lower alkoxy, aralkyloxy, or acyloxy; or
X and Y combined represent, —X—Y—, =O, —CH$_2$O(C=O)O—, —CH$_2$OC(=S)O—, —CH$_2$NR$^{26}$C(=O)—(wherein R$^{26}$ is hydrogen or lower alkyl), —CH$_2$NHC(=S)O—, —CH$_2$OS(=O)O—, or —CH$_2$OC(CH$_3$)$_2$O—; and

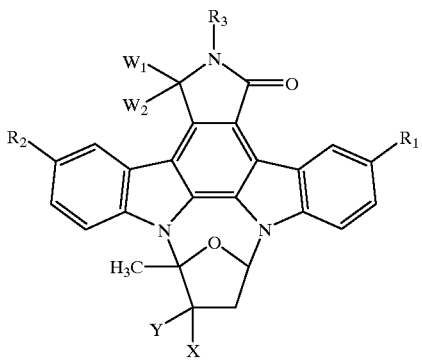

$W^1$ and $W^2$ are hydrogen, or $W^1$ and $W^2$ together represent oxygen;

or a pharmaceutically acceptable salt thereof.

The compounds represented by formula (I) are hereinafter referred to as Compound (I), and the same applies to the compounds of other formula numbers.

In the definitions of the groups in formula (I), lower alkyl means a straight-chain or branched alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl and hexyl. The lower allyl moiety of lower alkoxy, lower alkoxycarbonyl, lower alkylaminocarbonyl and tri-lower alkylsilyl has the same meaning as lower alkyl defined above. The acyl moiety of the acyl and the acyloxy groups means a straight-chain or branched alkanoyl group having 1 to 6 carbon atoms, such as formyl, acetyl, propanoyl, butyryl, valeryl, pivaloyl and hexanoyl, an arylcarbonyl group described below, or a heteroarylcarbonyl group described below. The aryl moiety of the aryl, the arylcarbonyl and the arylaminocarbonyl groups means a group having 6 to 12 carbon atoms such as phenyl, biphenyl and naphthyl. The heteroaryl moiety of the heteroaryl and the heteroarylcarbonyl groups contain at least one hetero atom selected from O, S, and N, and include pyridyl, pyrimidyl, pyrrolyl, furyl thienyl, imidazolyl triazolyl, tetrazolyl, quinolyl, isoquinolyl benzoimidazolyl thiazolyl and benzothiazolyl. The aralkyl moiety of the aralkyl and the aralkyloxy groups means an aralkyl group having 7 to 15 carbon atoms, such as benzyl, phenethyl, benzhydryl and naphthylmethyl. The substituted lower alkyl group has 1 to 3 independently-selected substituents, such as hydroxy, lower alkoxy, carboxyl, lower alkoxycarbonyl, nitro, amino, mono- or di-lower alkylamino, dioxolane, dioxane, dithiolane, and dithione. The lower alkyl moiety of the substituted lower alkyl, and the lower allyl moiety of the lower alkoxy, the lower alkoxycarbonyl, and the mono- or di-lower alkylamino in the substituents of the substituted lower alkyl group have the same meaning as lower alkyl defined above. The substituted aryl, the substituted heteroaryl and the substituted aralkyl groups each has 1 to 3 independently-selected substituents, such as lower alkyl, hydroxy, lower alkoxy, carboxy, lower alkoxycarbonyl, nitro, amino, mono- or di-lower alkylamino, and halogen. The lower alkyl moiety of the lower alkyl the lower alkoxy, the lower alkoxycarbonyl, and the mono- or di-lower alkylamino groups among the substituents has the same meaning as lower alkyl defined above. The heterocyclic group formed with a nitrogen atom includes pyrrolidinyl, piperidinyl, piperidino, morpholinyl, morpholino, thiomorpholino, N-methylpiperazinyl, indolyl, and isoindolyl. The α-amino acid groups include glycine, alanine, proline, glutamic acid and lysine, which may be in the L-form, the D-form or in the form of a racemate. Halogen includes fluorine, chlorine, bromine and iodine.

Preferably, one of $R^1$ and $R^2$ is selected from the group consisting of $-(CH_2)_kR^7$, $-CH=CH(CH_2)_mR^{12}$, $-C\equiv C(CH_2)_nR^{13}$, $-CO(CH_2)_jSR^{27}$, and $-CH_2OR^{44}$ wherein $R^{44}$ is methoxymethyl, ethoxymethyl, or methoxyethyl; and the other of $R^1$ and $R^2$ is selected from the group consisting of $-(CH_2)_rR^{17}$, $-CH=CH(CH_2)_tR^{18}$, $-C\equiv C(CH_2)_uR^{19}$, $NR^{14}R^{15}$, hydrogen, halogen, nitro, $-CH_2O-$ (substituted or unsubstituted) lower alkyl, $-CO(CH_2)_qSR^{27}$, $-CH_2R^{35}$, $-CH_2OH$, and $-CH_2SR^{37}$ wherein $R^{37}$ is selected from the group consisting of lower alkyl, pyridyl, and benzimidazole.

Preferably, $R^{35}$ is $OR^{36}$ wherein $R^{36}$, preferably, is selected from the group consisting of methoxymethyl, ethoxymethyl, and methoxyethyl.

Preferably, $R^{27}$ is selected from the group consisting of substituted or unsubstituted lower alkyl, substituted or unsubstituted phenyl, pyridyl, pyrimidinyl, thiazole, and tetrazole.

Preferably, k and r, independently, are each 2, 3, or 4.

Preferably, j and q, independently, are 1 or 2.

Preferably, $R^7$ and $R^{17}$, independently, are selected from the group consisting of (1) $CO_2R^8$ and $CO_2R^{8A}$, where $R^8$ and $R^{8A}$, independently, are hydrogen, methyl, ethyl, or phenyl; (2) phenyl, pyridyl, imidazolyl, thiazolyl, or tetrazolyl;(3) $OR^9$ and $OR^{9A}$ where $R^9$ and $R^{9A}$, independently, are hydrogen, methyl, ethyl, phenyl, or acyl; (4) $SR^{27B}$ where $R^{27B}$ is selected from the group consisting of unsubstituted lower alkyl, 2-thiazoline, and pyridyl; and (5) $NR^{10}R^{11}$ and $NR^{14}R^{15}$, where $R^{10}$, $R^{11}$, $R^{14}$, and $R^{15}$, independently, are selected from the group consisting of hydrogen, methyl, ethyl, phenyl, carbamoyl, and lower alkylaminocarbonyl.

Preferably, m, n, t and u, independently, are 0 or 1.

Preferably, $R^{12}$, $R^{13}$, $R^{18}$, and $R^{19}$, independently, are selected from the group consisting of hydrogen, methyl, ethyl, phenyl, pyridyl, imidazole, thiazole, tetrazole, $CO_2R^8$, $OR^9$, and $NR^{10}R^{11}$ where $R^8$, $R^9$, $R^{10}$, and $R^{11}$ have the preferred vales shown above.

Preferably, $R^3$ is hydrogen or acetyl, most preferably hydrogen.

Preferably, X is hydroxymethyl or lower alkoxycarbonyl with methoxycarbonyl being particularly preferred.

Preferably, Y is hydroxy or acetyloxy, most preferably hydroxy.

Preferably, each $W^1$ and $W^2$ is hydrogen.

Most preferred are the actual substituent values shown on the compounds in Table 1, with Compounds 1–157 being especially preferred.

III. Utilities

The selected ring substituted K-252a derivatives have evidenced important functional pharmacological activities which find utility in a variety of settings, including both research and therapeutic arenas. Generally, the activities of the compounds show positive effects on the function and/or survival of trophic factor responsive cells.

Effect on the function and/or survival of trophic factor responsive cells, e.g., cells of a neuronal lineage, can be established using any of the following assays: (1) cultured spinal cord chlorine acetyltransferase ("ChAT") assay; or (2) cultured basal forebrain neuron ("BFN") ChAT activity assay.

As used herein, the term "effect" when used to modify the terms "function" and "survival" means a positive or negative alteration or change. An effect which is positive can be referred to herein as an "enhancement" or "enhancing" and an effect which is negative can be referred to herein as "inhibition" or "inhibiting".

As used herein, the terms "enhance" or "enhancing" when used to modify the terms "function" or "survival" means that the presence of a substituted K-252a derivative has a positive effect on the function and/or survival of a trophic factor responsive cell compared with a cell in the absence of the derivative. For example, and not by way of limitation, with respect to the survival of, e.g., a cholinergic neuror, the derivative would evidence enhancement of survival of a cholinergic neuronal population at risk of dying (due to, e.g., injury, a disease condition, a degenerative condition or natural progression) when compared to a cholinergic neuronal population not presented with such derivative, if the treated population has a comparatively greater period of functionality than the non-treated population.

As used herein, "inhibit" and "inhibition" mean that a specified response of a designated material (e.g., enzymatic activity) is comparatively decreased in the presence of a substituted K-252a derivative.

As used herein the term "neuron," "cell of neuronal lineage" and "neuronal cell" includes, but is not limited to, a heterogeneous population of neuronal types having singular or multiple transmitters and/or singular or multiple functions; preferably, these are cholinergic and sensory neurons. As used herein, the phrase "cholinergic neuron" means neurons of the Central Nervous System (CNS) and Peripheral Nervous System (PNS) whose neurotransmitter is acetylcholine; exemplary are basal forebran, striatal, and spinal cord neurons. As used herein, the phrase "sensory neuron" includes neurons responsive to environmental cues (e.g., temperature, movement) from, e.g., skin, muscle and joints; exemplary is a neuron from the dorsal root ganglion.

A "trophic factor-responsive cell," as defined herein, is a cell which includes a receptor to which a trophic factor can specifically bind; examples include neurons (e.g., cholinergic and sensory neurons) and non-neurona cell (e.g., monocytes and nonplastic cells).

The disclosed aromatic ring substituted K-252a derivatives can be used to enhance the function and/or survival of cells of neuronal lineage. They can also be used to enhance the function and/or survival of cells of neuronal lineage in a mammal, e.g., a human. In these contexts, the derivatives can be utilized individually or with other derivatives, or in combination with other beneficial molecules which also evidence the ability to effect the function and/or survival of a designated cell.

A variety of neurological disorders are characterized by neuronal cell which are dying, injured, functionally comprised, undergoing axonal degeneration, at risk of dying, etc. These disorders include, but are not limited to: Alzheimer's disease; motor neuron disorders (e.g. amyotrophic lateral sclerosis); Parkinson's; cerebrovascular disorders (e.g., stroke, ischaemia); Huntington's; AIDS dementia; epilepsy; multiple sclerosis; peripheral neuropathies (e.g., those affecting DRG neurons in chemotherapy-associate peripheral neuropathy) including diabetic neuropathy; disorders induced by excitatory amino acids; disorders associated with concussive or penetrating injuries of the brain or spinal cord.

ChAT catalyzes the synthesis of the neurotransmitter acetylcholine, and it is considered an enzymatic marker for a functional cholinergic neuron. A functional neuron is also capable of survival. Neuron survival is assayed by quantitation of the specific uptake and enzymatic conversion of a dye (e.g., cackling AM) by living neurons.

Because of their varied utilities, the K-252a derivatives disclosed herein find utility in a variety of settings. The compounds can be used in the development of in vitro models of neuronal cell survival, function, identification, or for the screening of other synthetic compounds which have activities similar to that of the K-252a derivatives. The compounds can be utilized in a research environment to investigate, define and determine molecular targets associated with functional responses. For example, by radiolabelling a K-252a derivative associated with a specific cellular function (e.g., mitogenesis), the target entity to which the derivative binds can be identified, isolated, and purified for characterization.

The pharmaceutically acceptable salts of Compounds (I) include pharmaceutically acceptable acid addition salts, metal salts, ammonium salts, organic amine addition salts, and amino acid addition salts. Examples of the acid addition salts are inorganic acid addition salts such as hydrochloride, sulfate and phosphate, and organic acid addition salts such as acetate, maleate, fumarate, tartrate, citrate and lactate; examples of the metal salts are alkali metal salts such as lithium salt, sodium salt and potassium salt, alkaline earth metal salts such as magnesium salt and calcium salt, aluminum salt, and zinc salt, examples of the ammonium salts are ammonium salt and tetramethylammonium salt; examples of the organic amine addition salts are salts with morpholine and piperdine; and examples of the amino acid addition salts are salts with glycine, phenylalanine, glutamic acid and lysine.

Compounds provided herein can be formulated into pharmaceutical compositions by admixture with pharmaceutically acceptable nontoxic excipients and carriers. Such compositions can be prepared for use in parenteral administration, particularly in the form of liquid solutions or suspensions; or oral administration, particularly in the form of tablets or capsules; or intranasally, particularly in the form of powders, nasal drops, or aerosols; or dermal, via, for example, trans-dermal patches.

The composition can be conveniently administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful paternal delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for trans-dermal patches are preferably lipophilic emulsions.

The compounds of this invention can be employed as the sole active agent in a phamaceutical composition. Alternatively, they can be used in combination with other active ingredients, e.g., other growth factors which facilitate neuronal survival or axonal regeneration in diseases or disorders.

Compound (I) and pharmaceutically acceptable salts thereof can be administered orally or non-orally, e.g., as an ointment or an injection. The concentrations of the compounds of this invention in a therapeutic composition can vary. The concentration will depend upon factors such as the total dosage of the drug to be administered, the chemical characteristics (e.g., hydrophobicity) of the compounds employed, the route of administration, the age, body weight and symptoms of a patient, etc. The compounds of this invention typically are provided in an aqueous physiological buffer solution containing about 0.1 to 10% w/v compound for parenteral administration. Typical dose ranges are from about 1 $\mu$g/kg to about 1 g/kg of body weight per day; a preferred dose range is from about 0.01 mg/kg to 100 mg/kg of body weight per day, and preferably about 0.1 to 20 mg/kg once to four times per day. A preferred dosage of drug to be administered is likely to depend on variables such as the type and extent of progression of the disease or disorder, the overall health status of the particular patient, the relative biological efficacy of the compound selected, and formulation of the compound excipient, and its route of administration.

Compound (I) and pharmaceutically acceptable salts thereof can be administered as they are, or in the form of various pharmaceutical compositions, according to the pharmacological activity and the purpose of administration. The pharmaceutical compositions in accordance with the present invention can be prepared by uniformly mixing an effective amount of Compound (I) or a pharmaceutically acceptable salt thereof, as an active ingredient, with a pharmaceutically acceptable carrier. The carrier may take a wide range of forms according to the forms of composition suitable for administration. It is desired that such pharmaceutical compositions are prepared in a unit dose form suitable for oral or non-oral administration. The forms for non-oral administration include ointment and injection.

Tablets can be prepared using excipients such as lactose, glucose, sucrose, mannitol and methyl cellulose, disintegrating agents such as starch, sodium alginate, calcium carboxymethyl cellulose and crystalline cellulose, lubricants such as magnesium stearate and talc, binders such as gelatin, polyvinyl alcohol, polyvinyl pyrrolidone, hydroxypropyl cellulose and methyl cellulose, surfactants such as sucrose fatty acid ester and sorbitol fatty acid ester, and the like in a conventional manner. It is preferred that each tablet contains 15–300 mg of the active ingredient.

Granules can be prepared using excipients such as lactose and sucrose, disintegrating agents such as starch, binders such as gelatin, and the like in a conventional manner. Powders can be prepared using excipients such as lactose and mannitol, and the like in a conventional manner. Capsules can be prepared using gelatin, water, sucrose, gum arabic, sorbitol, glycerin, crystalline cellulose, magnesium stearate, talc, and the like in a conventional manner. It is preferred that each capsule contains 15–300 mg of the active ingredient.

Syrup preparations can be prepared using sugars such as sucrose, water, ethanol, and the like in a conventional manner.

Ointment can be prepared using ointment bases such as vaseline, liquid paraffin, lanolin and macrogol, emulsifiers such as sodium lauryl lactate, benzalkonium chloride, sorbitan mono-fatty acid ester, sodium carboxymethyl cellulose and gum arabic, and the like in a conventional manner.

Injectable preparations can be prepared using solvents such as water, physiological saline, vegetable oils (e.g., olive oil and peanut oil), ethyl oleate and propylene glycol, solubilizing agents such as sodium benzoate, sodium salicylate and urethane, isotonicity agents such as sodium chloride and glucose, preservatives such as phenol, cresol, p-hydroxybenzoic ester and chlorobutanol, antioxidants such as ascorbic acid and sodium pyrosulfite, and the like in a conventional manner.

IV. General Description of the Synthetic Processes

The processes for preparing Compound (I) are described below.

Me, Et, Ph, Ac, Bn, Boc, and t-Bu in the structural formulae and tables represent methyl, ethyl, phenyl, acetyl, benzyl, tert-butoxycarbonyl, and tert-butyl, respectively.

The compounds of the present invention can be usually obtained from optically active K-252a as the starting compound, but all possible stereoisomers and their mixtures are also within the scope of the present invention.

In the processes shown below, if the defined groups are converted under the conditions of the processes or are not suitable for carrying out the processes, the desired compounds can be obtained by employing means for introduction or elimination of protective groups conventionally used in organic synthetic chemistry. [See, e.g. T. W. Greene, Protective Groups in Organic Synthesis, John Wiley & Sons Inc. (1981)] Oxidation, reduction, addition, elimination, condensation, or hydrolysis, which is conventionally used in organic synthetic chemistry, may be carried out, and if necessary, the order of the reaction steps for the introduction of substituents, and the like, may be varied. Further, conversion of the functional groups may be carried out more than one time.

Process 1

Compound (I-1), i.e., Compound (I) wherein at least one of $R^1$ and $R^2$ is $-CO(CH_2)_jR^4$ (wherein j and $R^4$ have the same significances as defined above), can be prepared according to the following reaction steps:

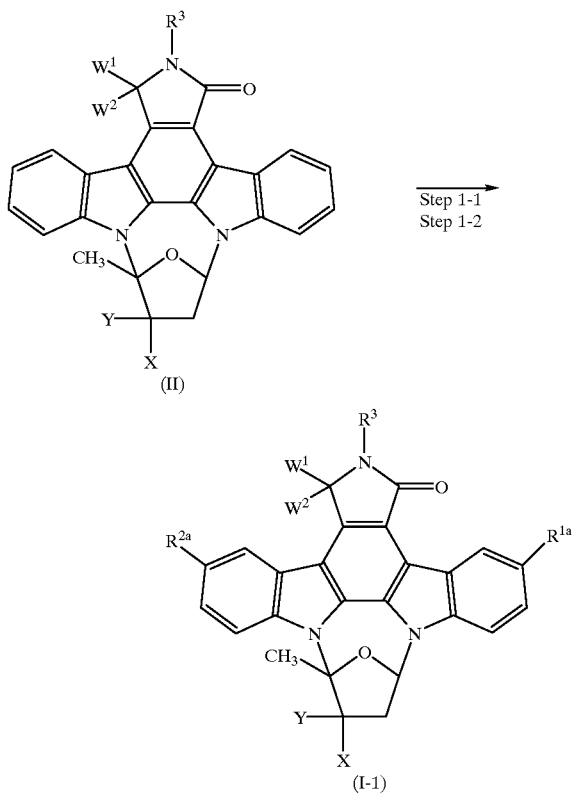

[In the formulae, $R^3$, $W^1$, $W^2$, X and Y have the same significances as defined above; and at least one of $R^{1a}$ and $R^{2a}$ is $-CO(CH_2)_jR^4$ (wherein j and $R^4$ have the same significances as defined above).]

Step 1-1

Compound (I-1a), i.e., Compound (I-1) wherein $R^4$ is halogen, can be obtained by subjecting Compound (II) which is a known compound described below to the Friedel-Crafts reaction with Compound (III) represented by formula (III):

$$R^{4a}-(CH_2)_jCO-Hal \qquad (III)$$

(wherein j has the same significance as defined above; $R^{4a}$ is halogen as defined above; and Hal is chlorine or bromine) or acryloyl chloride in a solvent such as methylene chloride and chloroform in the presence of a Lewis acid such as aluminum chloride.

Compound (III) and the Lewis acid are respectively used in an amount of 1 to 20 equivalents based on Compound (II). The reaction is usually carried out at 0 to 80° C. for 1 to 24 hours.

The starting Compound (II) can be prepared according to the processes disclosed in Japanese Published Unexamined Patent Applications Nos. 295588/88, 295589/88 and 807045/88.

Step 1-2

Compound (I-1b), i.e., Compound (I-1) wherein $R^4$ is $NR^5R^6$ (wherein $R^5$ and $R^6$ have the same significances as defined above), $N_3$, $OR^{29}$ (wherein $R^{29}$ has the same significance as defined above) or $SR^{27}$ (wherein $R^{27}$ has the same significance as defined above) can be obtained by subjecting Compound (I-1a) to reaction with a metallic salt of Compound (IVa) represented by formula (IVa):

$$HNR^5R^6 \qquad (IVa)$$

(wherein $R^5$ and $R^6$ have the same significances as defined above), sodium azide, Compound (IVb) represented by formula (Ivb):

$$R^{29}OH \qquad (IVb)$$

(wherein $R^{29}$ has the same significance as defined above), or Compound (IVc) represented by formula (Ivc):

$$R^{27}SH \qquad (IVc)$$

(wherein $R^{27}$ has the same significance as defined above) in a solvent such as methylene chloride, chloroform, dimethylsulfoxide or N,N-dimethylformamide, or reaction with Compound (IVa), (IVb) or (IVc) in the presence of a base such as potassium carbonate and triethylamine.

Compound (IVa), sodium azide, Compound (IVb), Compound (IVc) or a metallic salt thereof is used in an amount of 1 equivalent to excess amount based on Compound (I-1a), preferably 1 to 20 equivalents based on Compound (I-1a). A base is used in an amount of 1 to 20 equivalents. The reaction is usually carried out at 0 to 100° C. for 1 to 24 hours.

Process 2

Compound (I-2), i.e., Compound (I) wherein at least one of $R^1$ and $R^2$ is —CH=CH(CH$_2$)$_m$R$^{12}$ (wherein m and $R^{12}$ have the same significances as defined above) or —CH=C(CO$_2$R$^{33A}$)$_2$ (wherein $R^{33A}$ has the same significance as defined above) can be prepared according to the following reaction steps:

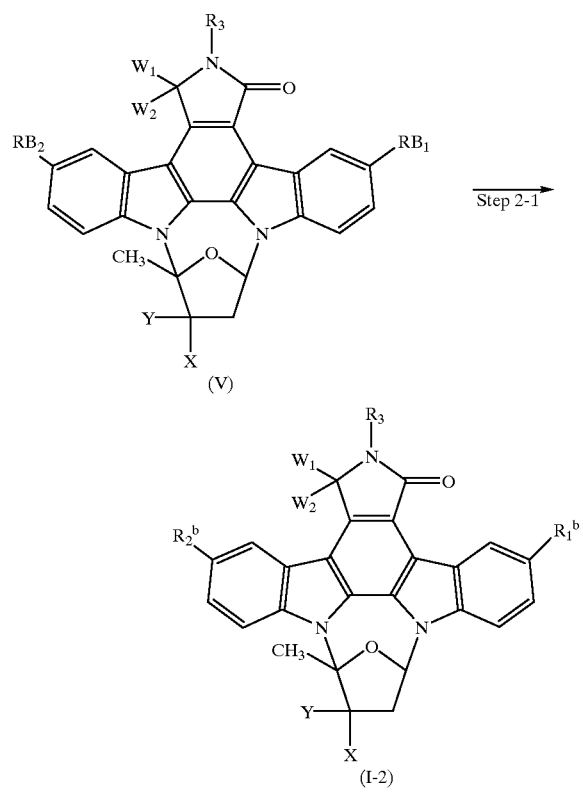

[in the formulae, $R^3$, $W^1$, $W^2$, X and Y have the same significances as defined above; at least one of $R^{B1}$ and $R^{B2}$ is formyl, hydroxymethyl, halogen or —C≡C(CH$_2$)$_m$R$^{12}$ (wherein m and $R^{12}$ have the same significances as defined above); and at least one of $R^{1b}$ and $R^{2b}$ is —CH=CH(CH$_2$)$_m$R$^{12}$ (wherein m and $R^{12}$ have the same significances as defined above) or —CH=C(CO$_2$R$^{33A}$)$_2$ (wherein $R^{33A}$ has the same significance as defined above).]

Step 2-1

Compound (I-2) can be obtained by subjecting Compound (Va) wherein at least one of $R^{B1}$ and $R^{B2}$ is formyl to reaction with Compound (VIa) represented by formula (VIa):

$$(Ph)_3P=CH(CH_2)_mR^{12} \qquad (VIa)$$

(wherein m and $R^{12}$ have the same significances as defined above; and Ph is phenyl) in a solvent such as methylene chloride and chloroform. Alternatively, Compound (I-2) can be obtained by subjecting Compound (Va) to reaction with Compound (VIb) represented by formula (VIb):

$$(Ph)_3P^+CH_2(CH_2)_mR^{12}Hal^- \qquad (VIb)$$

(wherein m, $R^{12}$, Ph and Hal have the same significances as defined above) in a solvent such as methylene chloride and chloroform in the presence of a base such as potassium carbonate and butyllithium. When a base which has poor solubility an the solvent, e.g. potassium carbonate, is used, the reaction is preferably carried out in the presence of a phase transfer catalyst such as 18-crown-6.

Compound (VIa), Compound (VIb) and the base are respectively used in an amount of 1 to 20 equivalents based on Compound (Va), and the phase transfer catalyst is used in an amount of 0.01 to 1 equivalent based on Compound (Va). The reaction is usually carried out at −10 to 100° C. for 1 to 100 hours.

Compound (Va) can be prepared according to the process disclosed in Japanese Published Unexamined Patent Application No. 295588/88.

Step 2-2

Compound (I-2) can be obtained by subjecting a phosphonium salt obtained from Compound (Vb) wherein at least one of $R^{B1}$ and $R^{B2}$ is hydroxymethyl and triphenylphosphine hydrobromide to reaction with Compound (VIc) represented by formula (VIc):

$$R^{12}(CH_2)_mCHO \qquad (VIc)$$

(wherein m and $R^{12}$ have the same significances as defined above) in a solvent such as methylene chloride in the presence of a base such as potassium carbonate and butyllithium. Compound (Vb) can be prepared according to the processes disclosed in Japanese Published Unexamined Patent Application No. 295588/88, WO94/02488,etc. When a base which has poor solubility in the solvent, e.g. potassium carbonate, is used, the reaction is preferably carried out in the presence of a phase transfer catalyst such as 18-crown-6.

Each of Compound (VIc) and the base is used in an amount of 1 to 20 equivalents based on the phosphonium salt (Vb), and the phase transfer catalyst is used in an amount of 0.01 to 1 equivalent based on the phosphonium salt (Vb). The reaction is usually carried out at −10 to 100° C. for 1 to 100 hours.

Step 2-3

Compound (I-2) can be obtained by subjecting Compound (Vc) wherein at least one of $R^{B1}$ and $R^{B2}$ is halogen to Heck reaction with Compound (VId) represented by formula (VId):

$$H_2C=CH(CH_2)_mR^{12} \qquad (VId)$$

(wherein m and $R^{12}$ have the same significances as defined above) in a solvent such as N,N-dimethylformamide in the presence of a palladium compound such as palladium (II) acetate and bistriphenylphosphine parallium (II) chloride, a phosphorus compound such as triphenylphosphine and tris(2-methylphenyl)phosphine and a base such as triethylamine.

Based on Compound (Vc), Compound (VId) is used in an amount of 1 to 40 equivalents, each of the palladium compound and phosphorus compound is used in an amount of 0.1 to 5 equivalents based on Compound (Vc), and the base is used in an amount of 1 to 500 equivalents. When the palladium compound used contains a phosphorus compound as a ligand as in the case of bis(triphenylphosphine) palladium (II) chloride, it is sometimes unnecessary to add the phosphorus compound. The reaction is usually carried out at 0 to 100° C. for 1 to 10 hours.

Step 2-4

Compound (I-2) can be obtained by subject Compound (I-3) synthesized according to Step 3 described below to catalytic reduction in a solvent such as N,N-dimethylformamide in a stream of hydrogen in the presence of a reduction catalyst such as palladium/carbon.

The reduction catalyst is used in an amount of 10 to 100% by weight based on Compound (I-3). The reaction is usually carried out at 0 to 100° C. for 1 to 72 hours.

Step 2-5

Compound (I-2) can be obtained by subjecting Compound (Va) to reaction with a compound represented by formula (VIe):

$$CH_2(CO_2R^{33A}) \qquad (VIe)$$

(wherein $R^{33A}$ has the same significance as defined above) in a solvent such as chloroform and methylene chloride in the presence of a base such as piperidine.

Compound (VIe) is used in an amount of 1 to 40 equivalents based on Compound (Va), and the base is used in an amount of 0.1 equivalent based on Compound (Va) to an amount equivalent to the solvent. The reaction is usually carried out at 20 to 100° C. for 1 to 24 hours.

Process 3

Compound (I-3), i.e., Compound (I) wherein at least one of $R^1$ and $R^2$ is —C≡C(CH_2)_nR^{13} (wherein n and $R^{13}$ have the same significances as defined above), can be prepared according to the following reaction steps:

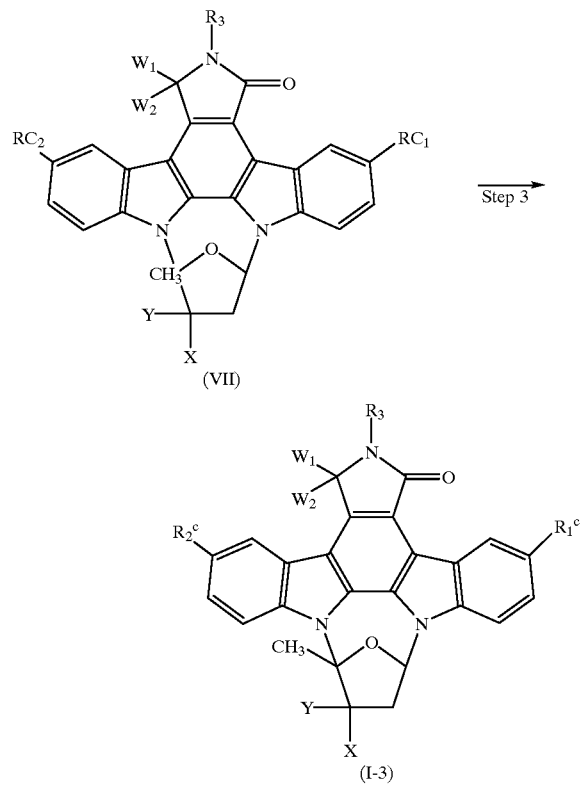

[In the formulae, $R^3$, $W^1$, $W^2$, X and Y have the same significances as defined above; at least one of $R^{C1}$ and $R^{C2}$ is iodine; and at least one of $R^{1c}$ and $R^{2c}$ is —C≡C(CH_2)_nR^{13} (wherein n and $R^{13}$ have the same significances as defined above).]

Step 3

Compound (I-3) can be obtained by subjecting Compound (VII) to the Sonogasira reaction with Compound (VIII) represented by formula (VIII):

$$HC≡C(CH_2)_nR^{13} \qquad (VIII)$$

(wherein n and $R^{13}$ have the same significances as defined above) in a solvent such as methylene chloride and chloroform in the presence of a copper compound such as cuprous iodide, a palladium compound such as palladium(II) acetate and bis(triphenylphosphine) palladium(II) chloride, a phosphorus compound such as triphenylphosphine, and a base such as diethylamine and triethylamine.

Compound (VIII) is used in an amount of 1 to 40 equivalents based on Compound (VII), the copper compound, the palladium compound and the phosphorus compound are respectively used in an amount of 0.1 to 5 equivalents, and the base is used in an amount of 1 to 500 equivalents. When the palladium compound contains the phosphorus compound as a ligand as in the case of bis(triphenylphosphine)palladium(II) chloride, it is not necessary to add the phosphorus compound. The reaction is usually carried out at 0 to 100° C. for 1 to 10 hours.

Compound (VII) can be obtained by subjecting Compound (II) to reaction with iodine in a solvent such as methylene chloride/methanol mixture (4/1) in the presence of a mercury compound such as mercuric nitrate and mercuric chloride. The mercury compound and iodine are respectively used in an amount of 1 to 3 equivalents based on Compound (II). The reaction is usually carried out at 0 to 50° C. for 1 to 24 hours.

Process 4

Compound (I-4), i.e., Compound (I) wherein at least one of $R^1$ and $R^2$ is —$(CH_2)_k R^7$ (wherein k and $R^7$ have the same significances as defined above) or —$CH_2CH(CO_2R^{33A})_2$ (wherein $R^{33A}$ has the same significance as defined above), can be prepared according to the following reaction steps:

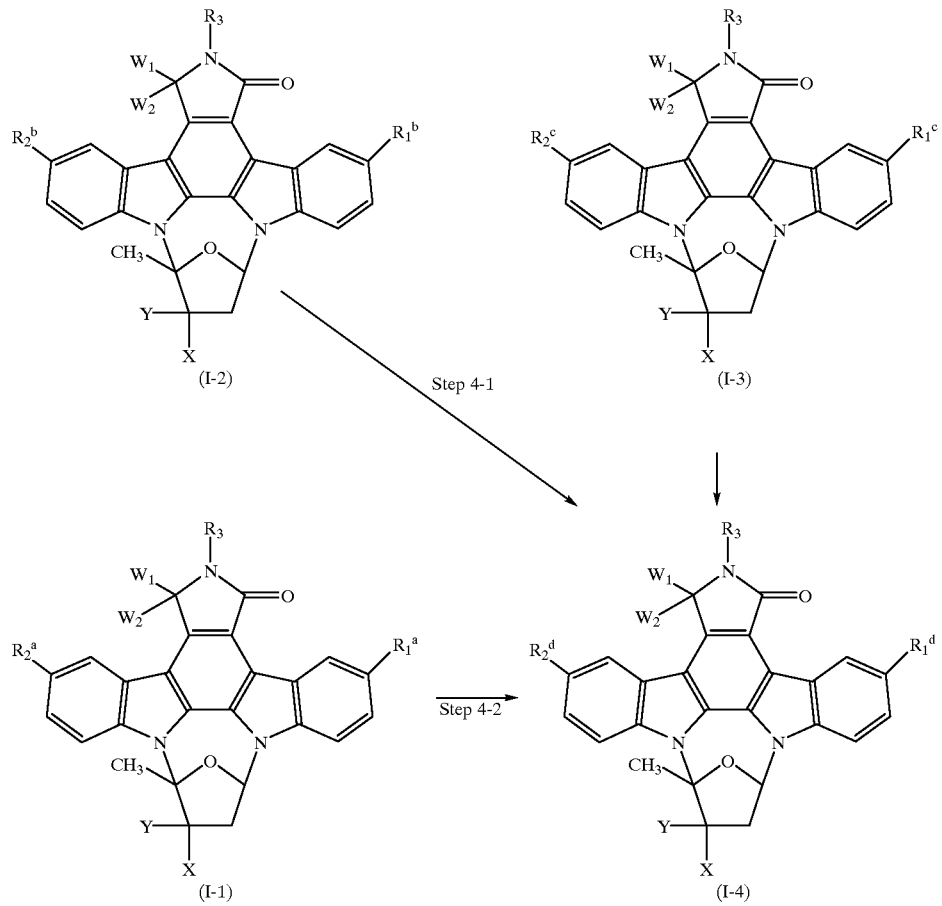

[In the formulae, $R^{1b}$, $R^{2b}$, $R^{1c}$, $R^{2c}$, $R^3$, $W^1$, $W^2$, X and Y have the same significances as defined above; and at least one of $R^{1d}$ and $R^{2d}$ is —$(CH_2)_k R^7$ (wherein k and $R^7$ have the same significances as defined above) or —$CH_2CH(CO_2R^{33A})_2$ (wherein $R^{33A}$ has the same significance as defined above).]

Step 4-1

Compound (I-4) can be obtained by subjecting Compound (I-2) or Compound (I-3) to catalytic reduction in a solvent such as N,N-dimethylformamide in a stream of hydrogen in the presence of a reduction catalyst such as 10% palladium/carbon and plutinum oxide.

The reduction catalyst is used in an amount of 10 to 100% (wt/wt) based on Compound (I-2) or Compound (I-3). The reaction is usually carried out at 0 to 100° C. for 1 to 72 hours.

Step 4-2

Compound (I-4) can be obtained by subjecting Compound (I-1) to reaction with alkylsilane such as ethylsilane in trifluoroacetic acid.

Trifluoroacetic acid is used in an amount equivalent to a solvent for Compound (I-1), and alkylsilane is used in an amount of 1 to 20 equivalents based on Compound (I-1). The reaction is usually carried out at −10 to 20° C. for 1 to 24 hours.

Process 5

Compound (I-5), i.e., Compound (I) wherein either of $R^1$ and $R^2$ is halogen or nitro, can be prepared by subjecting Compound (IX) to the reactions in Steps 1–4 in Processes 1–4 described above. Compound (IX) can be prepared according to the processes described in Japanese Published Unexamined Patent Applications Nos. 120388187 and 295588/88.

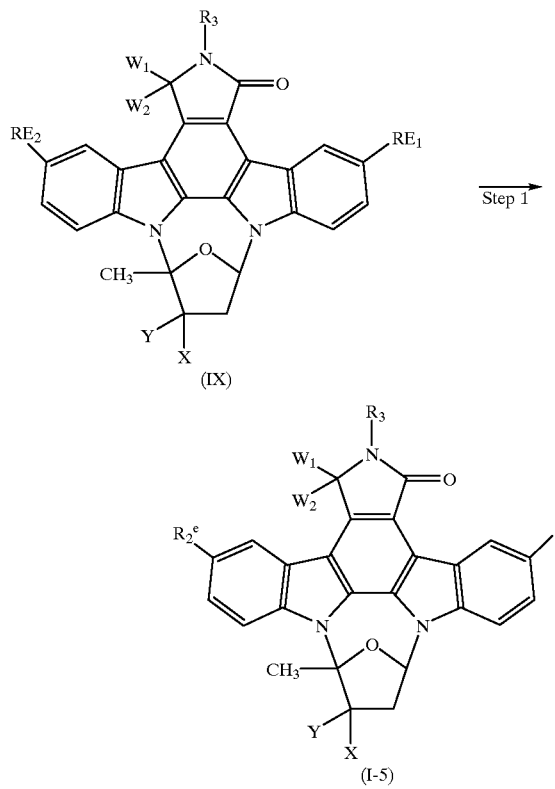

[In the formulae, $R^3$, $W^1$, $W^2$, X and Y have the same significances as defined above; either of $R^{E1}$ and $R^{E2}$ is halogen or nitro, and the other is hydrogen; and either of $R^{1e}$ and $R^{2e}$ is halogen, nitro or amine, and the other is —CO(CH$_2$)$_j$R$^4$ (wherein j and $R^4$ have the same significances as defined above), —CH$_2$)$_k$R$^7$ (wherein k and $R^7$ have the same significances as defined above), —CH=CH(CH$_2$)$_m$R$^{12}$ (wherein m and $R^{12}$ have the same significances as defined above), —CH=C(CO$_2$R$^{33B}$)$_2$ (wherein $R^{33B}$ has the same significance as defined above) or —C≡C(CH$_2$)$_n$R$^{13}$ (wherein n and $R^{13}$ have the same significances as defined above).]

Process 6

Compound (I-6), i.e., Compound (I) wherein either of $R^1$ and $R^2$ is NR$^{14}$R$^{15}$ (wherein $R^{14}$ and $R^{15}$ have the same significances as defined above), and the other is —CO(CH$_2$)$_j$R$^4$ (wherein j and $R^4$ have the same significances as defined above), —CH$_2$)$_k$R$^7$ (wherein k and $R^7$ have the same significances as defined above), —CH=CH(CH$_2$)$_m$R$^{12}$ (wherein m and $R^{12}$ have the same significances as defined above), —CH=C(CO$_2$R$^{33A}$)$_2$ (wherein $R^{33A}$ has the same significance as defined above) or —C≡C(CH$_2$)$_n$R$^{13}$ (wherein n and $R^{13}$ have the same significances as defined above), can be prepared from Compound (I-5) wherein either of $R^{1e}$ and $R^{2e}$ is nitro according to the process described in Japanese Published Unexamined Patent Application No. 295588/88.

Process 7

Compound (Ib), i.e., Compound (I) wherein $R^3$ is hydrogen, can also be prepared from Compound (Ia), i.e., Compound (I) wherein $R^3$ is acyl as defined above, according to the process described in Japanese Published Unexamined Patent Application No. 295588/88.

Process 8

Compound (I-7), i.e., Compound (I) wherein at least one of $R^1$ and $R^2$ is —CH(OH)(CH$_2$)$_b$R$^{44}$ (wherein b and $R^{44}$ have the same significances as defined above) can be obtained by reduction of a compound which can be synthesized according to the above Step 1-1 or 1-2, for example, reaction with a reducing agent such as sodium borohydride in a solvent such as methanol and methanol/chloroform. The reducing agent is used in an amount of 1 to 20 equivalents based on the raw material. The reaction is usually carried out at −10 to 50° C. for 0.5 to 24 hours.

Process 9

Compound (I-8), i.e., Compound (I) wherein either of $R^1$ and $R^2$ is formyl, and the other is —(CH$_2$)$_k$R$^7$ (wherein k and $R^7$ have the same significances as defined above), —CH=CH(CH$_2$)$_m$R$^{12}$ (wherein m and $R^{12}$ have the same significances as defined above), or —C≡C(CH$_2$)$_n$R$^{13}$ (wherein n and $R^{13}$ have the same significances as defined above), can be prepared according to Processes 2 to 4 after formylation of K-252a derivative (which can be prepared according to the process described in Reference Examples) wherein either of $R^1$ and $R^2$ is hydrogen and the other is bromine or iodine or both $R^1$ and $R^2$ are bromine or iodine.

Process 10

Compound (I-9), i.e., Compound (I) wherein either of $R^1$ and $R^2$ is —CH(SR$^{34}$)$_2$ (wherein $R^{34}$ has the same significance as defined above), and the other is —(CH$_2$)$_k$R$^7$ (wherein k and $R^7$ have the same significances as defined above), —CH=CH(CH$_2$)$_m$R$^{12}$ (wherein m and $R^{12}$ have the same significances as defined above), or —C≡C(CH$_2$)$_n$R$^{13}$ (wherein n and $R^{13}$ have the same significances as defined above), can be obtained by subject Compound (I-8) to reaction with Compound (X) represented by formula (X):

$$R^{34}SH \qquad (X)$$

(wherein $R^{34}$ has the same significance as defined above) in the presence of an acid catalyst such as BF$_3$.OEt$_2$.

Each of Compound (X) and the acid catalyst is used in an amount of 1 to 20 equivalents based on Compound (I-8). The reaction is usually carried out at 0 to 80° C. for 1 to 24 hours.

Process 11

Compound (I-10), i.e., Compound (I) wherein either of $R^1$ and $R^2$ is —CH$_2$R$^{35A}$ (wherein $R^{35A}$ has the same significance as $R^{35}$ except tri-lower alkylsilyloxy), and the other is —(CH$_2$)$_k$R$^7$ (wherein k and $R^7$ have the same significances as defined above), —CH=CH(CH$_2$)$_m$R$^{12}$ (wherein m and $R^{12}$ have the same significances as defined above), or —C≡C(CH$_2$)$_n$R$^{13}$ (wherein n and $R^{13}$ have the same significances as defined above), can be obtained by reduction of Compound (I-9) with a reducing agent such as sodium borohydride to form a compound wherein either of $R^1$ and $R^2$ is —CH$_2$OH, and then reaction with Compound (XI) represented by formula (XI):

$$R^{27}SH \qquad (XI)$$

(wherein $R^{27}$ has the same significance as defined above) or Compound (XII) represented by formula (XII):

$$R^{29}OH \qquad (XII)$$

(wherein $R^{29}$ has the same significance as defined above) in the presence of an acid catalyst such as camphorsulfonic acid.

The acid catalyst is used in an amount of 0.1 to 5 equivalents base on Compound (I-9), and Compound (XI) or (XII) is used in an amount of 1 to 20 equivalents based on Compound (I-9). The reaction is usually carried out at 0 to 80° C. for 1 to 100 hours.

Conversion of the functional groups in the substituents in $R^1$ and $R^2$ may be carried out according to the above steps or by known methods [see, e.g. R. C. Larock, Comprehensive Organic Transformations (1989)].

For example, conversion of the functional groups can be carried out by reacting Compound (I) containing a leaving group (e.g., chlorine, bromine, iodine or sulfonyloxy such as methylsulfonyoxy, trifluoromethanesulfonyloxy and p-toluenesulfonyloxy) in $R^1$ or $R^2$ with a nucleophilic reagent such as amine, alcohol, thiol and azide in the presence of a base such as pottasium carbonate to give new Compound (I).

Alternatively, when Compound (I) contains an azide groups in $R^1$ or $R^2$, the functional groups can be converted into amino groups by using a reducing agent such as triphenylphosphine, or the amino groups can be reacted with lower alkyl isocyanate or di-lower alkyl carbonate to obtain an urea derivative or carbamate.

The desired compounds in the processes described above can be isolated and purified by appropriate combinations of purification methods conventionally used in organic synthetic chemistry, for example, filtration, extraction, washing, drying, concentration, crystallization, and various kinds of chromatography. The intermediates may be subjected to the subsequent reaction without purification.

There may be stereoisomers such as geometrical isomers and optical isomers for Compound (I), and the present invention covers all possible isomers and their mixtures in any proportions.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of an acid to form a salt. Compound (I) and pharmaceutically acceptable salts thereof may be in the form of adducts with water or various solvents, which are also within the scope of the present invention.

Examples of Compound (I) are shown in Table 1 and the intermediates are shown in Table 2.

TABLE 1

| Compound | $R^1$ | $R^2$ | $R^3$ | Y |
|---|---|---|---|---|
| 1 | CH=CHCO$_2$Me | CH=CHCO$_2$Me | H | OH |
| 2 | CH=CHCO$_2$Et | H | H | OH |
| 3 | CH=CHCO$_2$Et | CH=CHCO$_2$Et | H | OH |
| 4 | CH=CHCO$_2$Me | H | H | OH |
| 5 | CH=CH—C$_6$H$_5$ | H | H | OH |
| 6 | CH=CH—C$_6$H$_5$ | CH=CH—C$_6$H$_5$ | H | OH |
| 7 | CH=CH-2-Pyr | H | H | OH |
| 8 | CH=CH-2-Pyr | CH=CH-2-Pyr | H | OH |
| 9 | CH$_2$CH$_2$—C$_6$H$_5$ | CH$_2$CH$_2$—C$_6$H$_5$ | H | OH |
| 10 | CH$_2$CH$_2$—C$_6$H$_5$ | H | H | OH |
| 11 | CH$_2$CH$_2$-2-Pyr | CH$_2$CH$_2$-2-Pyr | H | OH |
| 12 | H | CH=CHCO$_2$Et | H | OH |
| 13 | H | CH=CH-2-Pyr | H | OH |
| 14 | H | CH$_2$CH$_2$-2-Pyr | H | OH |
| 15 | NO$_2$ | CH=CH-2-Pyr | Ac | OAc |
| 16 | NO$_2$ | CH=CH-2-Pyr | H | OH |
| 17 | NH$_2$ | CH$_2$CH$_2$-2-Pyr | Ac | OAc |
| 18 | NH$_2$ | CH$_2$CH$_2$-2-Pyr | H | OH |
| 19 | NHCONHEt | CH$_2$CH$_2$-2-Pyr | H | OH |
| 20 | C≡CCH$_2$NMe$_2$ | C≡CCH$_2$NMe$_2$ | H | OH |
| 21 | C≡CCH$_2$OMe | I | H | OH |
| 22 | C≡CCH$_2$OMe | C≡CCH$_2$OMe | H | OH |
| 23 | C≡CCH$_2$OH | C≡CCH$_2$OH | H | OH |
| 24 | COCH$_2$Cl | COCH$_2$Cl | Ac | OAc |
| 25 | COCH$_2$-1-Pip | COCH$_2$-1-Pip | H | OH |
| 26 | COCH$_2$CH$_2$Cl | H | Ac | OAc |
| 27 | COCH$_2$CH$_2$Cl | COCH$_2$CH$_2$Cl | Ac | OAc |
| 28 | COCH$_2$CH$_2$-1-Pip | H | H | OH |
| 29 | COCH$_2$CH$_2$-1-Pip | COCH$_2$CH$_2$-1-Pip | H | OH |
| 30 | COCH$_2$CH$_2$-1-Morph | COCH$_2$CH$_2$-1-Morph | H | OH |
| 31 | COCH$_2$-1-Morph | COCH$_2$-1-Morph | H | OH |
| 32 | COCH$_2$NMe$_2$ | COCH$_2$NMe$_2$ | H | OH |
| 33a | COCH$_2$Cl | H | Ac | OAc |
| 33b | H | COCH$_2$Cl | Ac | OAc |
| 34 | COCH$_2$NMe$_2$ | H | H | OH |
| 35 | COCH$_2$-1-THP | H | H | OH |
| 36a | COCH$_2$-1-Morph | H | Ac | OAc |
| 36b | H | COCH$_2$-1-Morph | Ac | OAc |
| 37a | COCH$_2$-1-Morph | H | H | OH |
| 37b | H | COCH$_2$-1-Morph | H | OH |
| 38 | COCH$_2$-1-THP | COCH$_2$-1-THP | H | OH |
| 39 | COCH$_2$-1-Pipz(4-Me) | COCH$_2$-1-Pipz(4-Me) | Ac | OAc |
| 40 | COCH$_2$-1-Pipz(4-Me) | COCH$_2$-1-Pipz(4-Me) | H | OH |
| 41 | H | COCH$_2$SEt | H | OH |
| 42a | COCH$_2$S-4-Pyr | H | H | OH |
| 42b | H | COCH$_2$S-4-Pyr | H | OH |
| 43 | COCH$_2$SMe | COCH$_2$SMe | H | OH |
| 44 | COCH$_2$SEt | COCH$_2$SEt | H | OH |
| 45 | COCH$_2$SCH$_2$Et | COCH$_2$SCH$_2$Et | H | OH |
| 46 | COCH$_2$S(CH$_2$)$_2$OH | COCH$_2$S(CH$_2$)$_2$OH | H | OH |
| 47 | COCH$_2$S-4-Pyr | COCH$_2$S-4-Pyr | H | OH |
| 48 | COCH$_2$S-2-Pyr | COCH$_2$S-2-Pyr | H | OH |
| 49 | COCH$_2$S-2-Pyrm | COCH$_2$S-2-Pyrm | H | OH |
| 50 | COCH$_2$S—C$_6$H$_4$(4-OH) | COCH$_2$S—C$_6$H$_4$(4-OH) | H | OH |
| 51 | COCH$_2$S-2-Thiazl | COCH$_2$S-2-Thiazl | H | OH |
| 52 | COCH$_2$S-5-Tet(1-Me) | COCH$_2$S-5-Tet(1-Me) | H | OH |
| 53 | CO(CH$_2$)$_2$SMe | CO(CH$_2$)$_2$SMe | H | OH |
| 54 | CO(CH$_2$)$_2$OMe | CO(CH$_2$)$_2$OMe | H | OH |
| 55 | Br | CO(CH$_2$)$_3$H | H | OH |
| 56 | CO(CH$_2$)$_4$H | CO(CH$_2$)$_4$H | Ac | OAc |

TABLE 1-continued

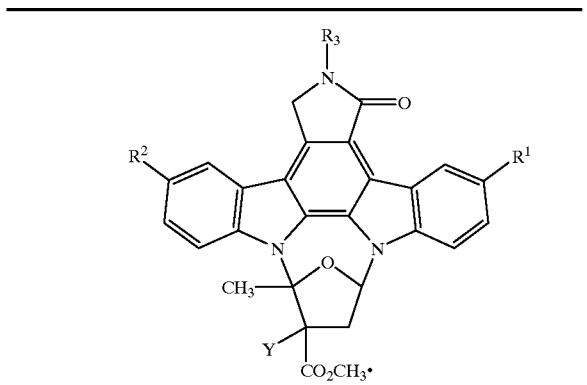

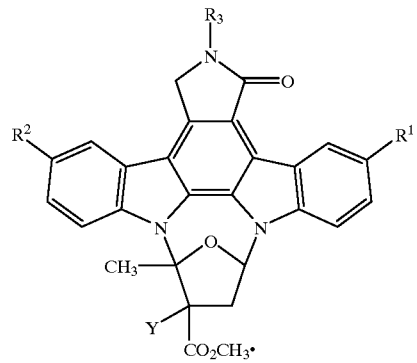

| Compound | R¹ | R² | R³ | Y |
|---|---|---|---|---|
| 57 | COCH$_2$Br | COCH$_2$Br | Ac | OAc |
| 58 | CH(OH)Me | H | Ac | OAc |
| 59 | CH(OH)(CH$_2$)$_2$Cl | CH(OH)(CH$_2$)$_2$Cl | H | OH |
| 60 | CH(OH)CH$_2$-1-Pipz(4-Me) | CH(OH)CH$_2$-1-Pipz(4-Me) | H | OH |
| 61 | C≡CCH$_2$NMe$_2$ | H | H | OH |
| 62 | Br | C≡CCH$_2$NMeBn | H | OH |
| 63 | CH=CHCH$_2$NMe$_2$ | CH=CHCH$_2$NMe$_2$ | Ac | OAc |
| 64 | CH=CHCH$_2$NMe$_2$ | CH=CHCH$_2$NMe$_2$ | H | OH |
| 65 | CH=CHEt | H | Ac | OAc |
| 66 | CH=CHEt | H | H | OH |
| 67 | CH=CHEt | I | Ac | OAc |
| 68 | CH=CHEt | CH=CHEt | H | OH |
| 69 | (CH$_2$)$_2$Cl | (CH$_2$)$_2$Cl | H | OH |
| 70a | (CH$_2$)$_2$I | (CH$_2$)$_2$I | H | OH |
| 70b | (CH$_2$)$_2$OCOH | (CH$_2$)$_2$OCOH | H | OH |
| 70c | (CH$_2$)$_2$OH | (CH$_2$)$_2$OH | H | OH |
| 71 | (CH$_2$)$_2$OCO-4-Pyr | (CH$_2$)$_2$OCO-4-Pyr | H | OH |
| 72a | CH$_2$CO$_2$Me | H | H | OH |
| 72b | CH$_2$CO$_2$Me | CH$_2$CO$_2$Me | H | OH |
| 73a | (CH$_2$)$_3$I | (CH$_2$)$_3$I | H | OH |
| 73b | (CH$_2$)$_3$OCOH | (CH$_2$)$_3$OCOH | H | OH |
| 73c | (CH$_2$)$_3$OH | (CH$_2$)$_3$OH | H | OH |
| 74 | (CH$_2$)$_3$OMe | (CH$_2$)$_3$OMe | H | OH |
| 75 | (CH$_2$)$_2$-1-Pip | (CH$_2$)$_2$-1-Pip | H | OH |
| 76 | (CH$_2$)$_2$-1-Morph | (CH$_2$)$_2$-1-Morph | H | OH |
| 77 | (CH$_2$)$_2$NEt$_2$ | (CH$_2$)$_2$NEt$_2$ | H | OH |
| 78 | (CH$_2$)$_2$NMe(CH$_2$)$_2$OH | (CH$_2$)$_2$NMe(CH$_2$)$_2$OH | H | OH |
| 79 | (CH$_2$)$_2$NHMe | (CH$_2$)$_2$NHMe | H | OH |
| 80 | (CH$_2$)$_2$NHCH$_2$C$_6$H$_4$(4-MeO) | (CH$_2$)$_2$NHCH$_2$C$_6$H$_4$(4-Meo) | H | OH |
| 81 | (CH$_2$)$_2$N$_3$ | (CH$_2$)$_2$N$_3$ | H | OH |
| 82 | (CH$_2$)$_3$-1-Pip | (CH$_2$)$_3$-1-Pip | H | OH |
| 88 | (CH$_2$)$_3$-1-Morph | (CH$_2$)$_3$-1-Morph | H | OH |
| 84 | (CH$_2$)$_3$NEt$_2$ | (CH$_2$)$_3$NEt$_2$ | H | OH |
| 85 | (CH$_2$)$_3$NHCONHEt | (CH$_2$)$_3$NHCONHEt | H | OH |
| 86 | (CH$_2$)$_3$NHCO$_2$t-Bu | (CH$_2$)$_3$NHCO$_2$t-Bu | H | OH |
| 87 | (CH$_2$)$_2$SMe | (CH$_2$)$_2$SMe | H | OH |
| 88 | (CH$_2$)$_2$SEt | (CH$_2$)$_2$SEt | H | OH |
| 89 | (CH$_2$)$_2$SCH$_2$CO$_2$Me | (CH$_2$)$_2$SCH$_2$CO$_2$Me | H | OH |
| 90 | (CH$_2$)$_2$S(CH$_2$)$_2$CO$_2$Et | (CH$_2$)$_2$S(CH$_2$)$_2$CO$_2$Et | H | OH |
| 91 | (CH$_2$)$_2$S—C$_6$H$_4$(4-OH) | (CH$_2$)$_2$S—C$_6$H$_4$(4-OH) | H | OH |
| 92 | (CH$_2$)$_2$S-2-Thiazl | (CH$_2$)$_2$S-2-Thiazl | H | OH |
| 93 | (CH$_2$)$_2$S-4-Pyr | (CH$_2$)$_2$S-4-Pyr | H | OH |
| 94 | (CH$_2$)$_2$S-2-Pyr | (CH$_2$)$_2$S-2-Pyr | H | OH |
| 95 | (CH$_2$)$_3$SMe | (CH$_2$)$_3$SMe | H | OH |
| 96 | (CH$_2$)$_3$S-2-(Benz)Thiazole | (CH$_2$)$_3$S-2-(Benz)Thiazole | H | OH |
| 97 | CH=CH-2-Pyr | CHO | Ac | OAc |
| 98 | CH=CH-2-Pyr | CH$_2$OH | Ac | OAc |
| 99 | CH=CH-2-Pyr | CH$_2$OH | H | OH |
| 100 | CH=CH-2-Pyr | CH$_2$OSiMe$_2$t-Bu | Ac | OAc |
| 101 | CH=CH-2-Pyr | CH$_2$OSiMe$_2$t-Bu | H | OH |
| 102 | CH=CH-2-Pyr | CH$_2$OMe | H | OH |
| 103 | CH=CH-2-Pyr | CH$_2$OEt | H | OH |
| 104 | CH=CH-2-Pyr | CH$_2$O(CH$_2$)$_2$NMe$_2$ | H | OH |
| 105 | CH=CH-2-Pyr | CH$_2$SEt | H | OH |
| 106 | CH=CH-2-Pyr | CH$_2$S(CH$_2$)$_2$NMe$_2$ | H | OH |
| 107 | CH=CH-2-Pyr | CH$_2$S-2-(Benz)Imid | H | OH |
| 108 | CH=CH-2-Pyr | CH$_2$S-2-Pyr | H | OH |
| 109 | CH=CH-2-Pyr | CH(SEt)$_2$ | Ac | OAc |
| 110 | CH=CH-2-Pyr | CH (SEt)$_2$ | H | OH |
| 111 | CHO | CH=CH-2-Pyr | Ac | OAc |
| 112 | CH$_2$OH | CH=CH-2-Pyr | Ac | OAc |
| 113 | CH$_2$OH | CH=CH-2-Pyr | H | OH |
| 114 | CH$_2$OSiMe$_2$t-Bu | CH=CH-2-Pyr | Ac | OAc |
| 115 | CH$_2$OSiMe$_2$t-Bu | CH=CH-2-Pyr | H | OH |
| 116 | CH$_2$OMe | CH=CH-2-Pyr | H | OH |
| 117 | CH$_2$OEt | CH=CH-2-Pyr | H | OH |
| 118 | CH$_2$SEt | CH=CH-2-Pyr | H | OH |
| 119 | CH$_2$S-2-Pyr | CH=CH-2-Pyr | H | OH |
| 120 | CH$_2$S-2-(Benz)Imid | CH=CH-2-Pyr | H | OH |
| 121 | CH=CHEt | CH=CH-2-Pyr | Ac | OAc |
| 122 | CH=CHEt | CH=CH-2-Pyr | H | OH |
| 123 | (CH$_2$)$_2$-2-Pyr | CH$_2$OSiMe$_2$t-Bu | Ac | OAc |
| 124 | (CH$_2$)$_2$-2-Pyr | CH$_2$OSiMe$_2$t-Bu | H | OH |
| 125a | (CH$_2$)$_2$-2-Pyr | CH$_2$OMe | Ac | OAc |
| 125b | (CH$_2$)$_2$-2-Pyr | CH$_2$OMe | H | OAc |
| 126 | (CH$_2$)$_2$-2-Pyr | CH$_2$OMe | H | OH |
| 127a | (CH$_2$)$_2$-2-Pyr | CH$_2$OEt | H | OH |
| 127b | (CH$_2$)$_2$-2-Pyr | CH$_2$OH | H | OH |
| 128 | (CH$_2$)$_2$-2-Pyr | CH$_2$S-2-Pyr | Ac | OAc |
| 129 | (CH$_2$)$_2$-2-Pyr | CH$_2$S-2-Pyr | H | OH |
| 130 | CH$_2$OSiMe$_2$t-Bu | (CH$_2$)$_2$-2-Pyr | Ac | OAc |
| 131 | CH$_2$OSiMe$_2$t-Bu | (CH$_2$)$_2$-2-Pyr | H | OH |
| 132 | CH$_2$OMe | (CH$_2$)$_2$-2-Pyr | H | OH |
| 133 | CH$_2$OEt | (CH$_2$)$_2$-2-Pyr | H | OH |
| 134 | CH$_2$SEt | (CH$_2$)$_2$-2-Pyr | H | OH |
| 135 | CH$_2$S(CH$_2$)$_2$NMe$_2$ | (CH$_2$)$_2$-2-Pyr | H | OH |
| 136 | CH$_2$S-2-Pyr | (CH$_2$)$_2$-2-Pyr | Ac | OAc |
| 137 | CH$_2$S-2-Pyr | (CH$_2$)$_2$-2-Pyr | H | OH |
| *138 | C≡CCH$_2$OMe | C≡CCH$_2$OMe | H | OH |
| 139 | CH$_2$CH$_2$CO$_2$Me | CH$_2$CH$_2$CO$_2$Me | H | OH |
| 140 | CH$_2$CH$_2$CO$_2$Et | CH$_2$CH$_2$CO$_2$Et | H | OH |
| 141 | Br | CH=CH-2-Pyr | Ac | OAc |
| 142 | Br | CH=CH-2-Pyr | H | OH |
| 143 | Br | CH$_2$CH$_2$-2-Pyr | H | OH |
| 144 | CH=CH-4-Pyr | CH=CH-4-Pyr | Ac | OAc |
| 145 | CH=CH-4-Pyr | CH=CH-4-Pyr | H | OH |
| 146 | CH$_2$CH$_2$-4-Pyr | CH$_2$CH$_2$-4-Pyr | H | OH |
| 147 | CH=CH-2-Imid | H | Ac | OAc |
| 148 | CH=CH-2-Imid | H | H | OH |
| 149 | CH$_2$CH$_2$-2-Imid | H | H | OH |
| 150 | CH=C(CO$_2$Me)$_2$ | CH=C(CO$_2$Me)$_2$ | Ac | OAc |
| 151 | CH$_2$CH(CO$_2$Me)$_2$ | CH$_2$CH(CO$_2$Me)$_2$ | Ac | OAc |
| 152 | CH$_2$CH(CO$_2$Me)$_2$ | CH$_2$CH(CO$_2$Me)$_2$ | H | OH |
| 153 | n-C$_4$H$_9$ | (CH$_2$)$_2$-2-Pyr | H | OH |
| 154 | CH$_2$OCH$_2$OMe | H | H | OH |
| 155 | CH$_2$OCH$_2$OMe | CH$_2$OCH$_2$OMe | H | OH |

TABLE 1-continued

| Compound | R¹ | R² | R³ | Y |
|---|---|---|---|---|
| 156 | CH$_2$OCH$_2$OEt | CH$_2$OCH$_2$OEt | H | OH |
| 157 | CH$_2$O(CH$_2$)$_2$OMe | CH$_2$O(CH$_2$)$_2$OMe | H | OH |

Pyr = Pyridyl
Pip = Piperidine
Morph = Morpholine
THP = Tetrahydropyrrole
Pipz = Piperazine
Pyrm = Pyrimidine
Thiazl = Thiazoline
Tet = Tetrazole
Imid = Imidazole
(Benz)Thiazole = Benzothiazole
(Benz)Imid = Benzimidazole
*The CO$_2$CH$_3$ group is replaced with CH$_2$OH.

TABLE 2

| Compound | R1 | R2 | R3 | Y |
|---|---|---|---|---|
| A | Br | H | Ac | OAc |
| B | Br | CHO | Ac | OAc |
| C | H | CHO | Ac | OAc |
| D | NO2 | H | Ac | OAc |
| E | NO2 | CHO | Ac | OAc |
| F | I | I | Ac | OAc |
| G | I | I | H | OH |
| H | I | H | Ac | OAc |
| I | Br | I | Ac | OAc |
| J | CHO | I | Ac | OAc |
| K | CH2OH | I | Ac | OAc |

EXAMPLES

Certain embodiments of the invention are illustrated in the following Examples and Reference Examples.

Figure 9:
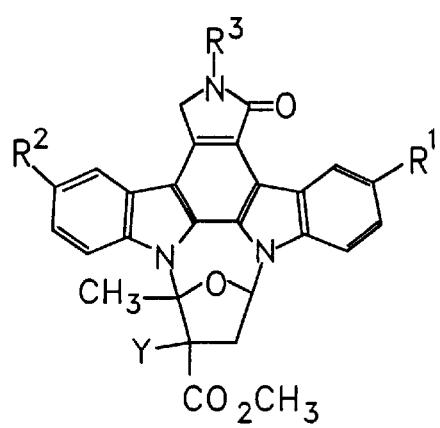
FIG. 9 depicts the structures of certain known K-252a derivatives which are used as starting materials to prepare compounds of the invention.

Compounds a–e and g which are known compounds used as the starting compounds are described in Japanese Published Unexamined Patent Application No. 295588/88. Compounds f and h are described in WO94/02488. The structures are shown below in FIG. 9.

| Compound | R1 | R2 | R3 | Y |
|---|---|---|---|---|
| a | CHO | CHO | Ac | OAc |
| b | CHO | H | Ac | OAc |
| c | H | H | Ac | OAc |
| d | Ac | H | Ac | OAc |
| e | CH$_2$OH | H | Ac | OAc |
| f | CH$_2$OH | CH$_2$OH | Ac | OAc |
| g | Ac | Ac | Ac | OAc |
| h | CH$_2$OH | CH$_2$OH | H | OH |

Example 1

Synthesis of Compound 1

Step A

To a solution of 50.0 mg (0.0824 mmol) of Compound a (Japanese Published Unexamined Patent Application No. 295588/88) in 5 ml of chloroform was added 198 mg (0.592 mmol) of methyl(triphenylphosphoranylidene)acetate, followed by stirring under reflux for 4 hours. After cooling, the solvent was evaporated under reduced pressure, and the residue was purified by silica gel column chromatography (chloroform/methanol=98/2) to give diacetylated Compound 1.

FAB-MS (m/z); 720 (M+1)$^+$

Step B

To a solution of 71.0 mg of diacetylated Compound 1 in a mixture of 4 ml of 1,2-dichloromethane and 1 ml of methanol was added 18 ml (0.09 mmol) of 5.1 N sodium methoxide/methanol solution, and the mixture was stirred at room temperature for 30 minutes. The reaction mixture was poured into water, followed by extraction with tetrahydrofuran. The organic layer was washed with a saturated aqueous solution of sodium chloride and dried over magnesium sulfite. After evaporation of the solvent under reduced pressure, the residue was crystallized from chloroform-methanol to give 16.3 mg (yield from Compound a: 31%) of Compound 1.

$^1$H-NMR (DMSO-d$_6$)δ; 2.04 (dd, 1H, J=4.9, 14.1 Hz), 2.12 (s, 3H), 3.42 (dd, 1H, J=7.5, 14.1 Hz), 3.77 (s, 6 H), 3.93 (s, 3H), 5.10 (s, 2H),6.43 (s, 1H), 6.59 (d, 1H, J=15.9 Hz), 6.78 (d, 1H, J=15.9 Hz), 7.21 (dd, 1H, J=4.9, 7.5 Hz), 7.85 (d, 1H, J=15.9 Hz), 7.95 (d, 1H, J=15.9 Hz), 7.88 –8.00 (m, 4 H), 8.40 (d, 1H, J=1.2 Hz), 8.79 (s, 1H), 9.48 (d, 1H, J=1.7 Hz).

FAB-MS (m/z); 636 (M+1)$^+$

Example 2
Synthesis of Compound 2

The same procedure as in Example 1, Step A was repeated using 55.7 mg (0.0962 mmol) of Compound b (Japanese Published Unexamined Patent Application No. 295588/88) and 92.1 mg. (0.264 mmol) of ethyl (triphenylphosphoranylidene)acetate to give diacetylated Compound 2.

FAB-MS (m/z); 650 (M+1)$^+$

The same procedure as in Example 1, Step B was repeated using diacetylated Compound 2 to give 27.5 mg (yield from Compound b: 51%) of Compound 2.

$^1$H-NMR (DMSO-d$_6$) δ; 1.31 (t, 3H, J=7.1 Hz), 2.05 (dd, 1H, J=4.9, 14.1 Hz) 2.15 (s, 3H), 3.41 (dd, 1H, J=7.3, 14.1 Hz), 3.93 (s, 3H), 4.23 (q, 2H, J=7.1 Hz), 5.00 (d, 1H, J=17.5 Hz), 5.06 (d, 1H, J=17.5 Hz), 6.36 (s, 1H), 6.56 (d, 1H, J=15.9 Hz), 7.19 (dd, 1H, J=4.9, 7.3 Hz), 7.84 (d, 1H, J=15.9 Hz), 7.36–8.08 (m, 6H), 8.69 (s, 1H), 9.47 (d, 1H, J=1.5 Hz).

FAB-MS (m/z); 565 (M)$^+$, 566 (M+1)$^+$

Example 3
Synthesis of Compound 3

The same procedure as in Example 1, Step A was repeated using 50.0 mg (0.0824 mmol) of Compound a and 225 mg (0.645 mmol) of ethyl (triphenylphosphoranylidene)acetate to give diacetylated Compound 3.

FAB-MS (m/z); 747 (M)$^+$, 748 (M+1)$^+$

The same procedure as in Example 1, Step B was repeated using diacetylated Compound 3 to give 29.7 mg (yield from Compound a: 54%) of Compound 3.

$^1$H-NMR (DMSO-d$_6$) δ; 1.31 (t, 6 H, J=7.1 Hz), 2.04 (dd, 1H, J=4.9, 14.2 Hz), 2.15 (s, 3H), 3.42 (dd, 1H, J=7.4, 14.2 Hz), 3.93 (s, 3H), 4.23 (q, 2H, J=7.1 Hz), 4.23 (q, 2H, J=7.1 Hz), 5.10 (s, 2H), 6.43 (s, 1H), 6.58 (d, 1H, J=15.9 Hz), 6.77 (d, 1H, J=16.0 Hz), 7.21 (dd, 1H, J=4.9, 7.4 Hz), 7.83 (d, 1H, J=15.9 Hz), 7.93 (d, 1H, J=16.0 Hz), 7.88–8.00 (m, 4 H, 8.40 (d, 1H, J=1.5 Hz), 8.78 (s, 1H), 9.47 (d, 1H, J=1.6 Hz).

FAB-MS (m/z); 664 (M+1)$^+$

Example 4
Synthesis of Compound 4

The same procedure as in Example 1, Step A was repeated using 50.0 mg (0.0824 mmol) of Compound b and 104 mg (0.311 mmol) of methyl (triphenylphosphoranylidene)-acetate to give diacetylated Compound 4.

FAB-MS (m/z); 636 (M+1)$^+$

The same procedure as in Example 1, Step B was repeated using diacetylated Compound 4 to give 14.6 mg (yield from Compound b: 31%) of Compound 4.

$^1$H-NMR (DMSO-d$_6$)δ; 2.05 (dd, 1H, J=4.9, 14.2 Hz), 2.15 (s, 3H), 3.41 (dd, 1H, J=7.5, 14.2 Hz), 3.77 (s, 3H), 3.93 (s, 3H), 5.00 (d, 1H, J=17.6 Hz), 5.06 (d, 1H, J=17.6 Hz), 6.36 (s, 1H), 6.59 (d, 1H, J=15.8 Hz), 7.19 (dd, 1H, J=4.9, 7.5 Hz),7.85 (d, 1H, J=15.8 Hz), 7.36–8.08 (m, 6 H), 8.70 (s, 1H), 9.47 (d, 1H, J=1.5 Hz).

FAB-MS (m/z); 552 (M+1)$^+$

Example 5
Synthesis of Compound 5

To a solution of 215 mg (0.553 mmol) of benzyltriphenylphosphonium chloride in 2 ml of dichloromethane were added 165 mg (1.19 mmol) of potassium carbonate and 12 mg (0.045 mmol) of 18-crown-6, followed by stirring at room temperature for 5 minutes. After addition of a solution of 80.0 mg (0.138 mmol) of Compound b in 8 ml of dichloromethane, the mixture was stirred overnight at room temperature. Insoluble materials in the reaction mixture were filtered off, and the solvent was evaporated under reduced pressure. The residue was purified by silica gel column chromatography (chloroform) and then by preparative TLC (chloroform/methanol=99/1) to give 80.0 mg (89%) of diacetylated Compound 5.

FAB-MS (m/z); 564 (M+1)$^+$

The same procedure as in Example 1, Step B was repeated using 80.0 mg (0.123 mmol) of diacetylated Compound 5 to give 26.1 mg (37%) of Compound 5 (E/Z=3/7).

$^1$H-NMR (DMSO-d$_6$) δ2.00–2.57 (m, 1H), 2.13 (s, 2.1H), 2.14 (s, 0.9H), 3.37 (dd, 0.7H, J=7.5, 14.2 Hz), 3.40 (dd, 0.3H, J=7.6, 13.7 Hz), 3.90 (s, 2.1H), 3.92 (s, 0.9H), 4.93–5.60 (m, 2H), 6.33 (s, 0.7H), 6.34 (s, 0.3H), 6.621 (d, 0.7H, J=12.4 Hz), 6.849 (d, 0.7H, J=12.4 Hz), 7.072 (dd, 0.7H, J=4.9, 7.5 Hz), 7.132–8.064 (m,11.9H), 8.58 (s, 0.7H), 8.63 (s, 0.3H), 9.15 (m, 0.7H), 9.38 (d, 0.3H, J=1.7 Hz).

FAB-MS (m/z); 570 (M+1)$^+$

Example 6
Synthesis of Compound 6

The same procedure as in Example 5 was repeated using 250 mg (0.643 mmol) of benzyltriphenylphosphonium chloride and 50.0 mg (0.0824 mmol) of Compound a to give 63.5 mg of diacetylated Compound 6.

FAB-MS (m/z); 756 (M+1)$^+$

The same procedure as in Example 1, Step B was repeated using 63.5 mg (0.0841 mmol) of diacetylated Compound 6 to give 49.9 mg (yield from Compound a: 90%) of Compound 6 (R$^1$, R$^2$: cis, trans/R$^1$, R$^2$: cis, cis/R$^1$, R$^2$: trans, cis/R$^1$, R$^2$: trans, trans=2/1/1/1).

$^1$H-NMR (DMSO-d$_6$) δ; 1.99–2.08 (m, 1H), 2.10, 2.12, 2.15, 2.17 (4×s, 3H), 3.35–3.45 (m, 1H), 3.89, 3.92, 3.92, 3.93 (4×s, 3H), 4.50–5.03 (m, 2H), 6.35, 6.36, 6.40, 6.41 (4×s 1H), 6.61–8.23 (m, 20H), 8.59, 8.57, 8.67, 8.72 (m, 1H), 9.13, 9.17, 9.36,9.40 (m, 1H).

FAB-MS (m/z); 672 (M+1)$^+$

Example 7
Synthesis of Compound 7

The same procedure as in Example 5 was repeated using 61.8 mg (0.142 mmol) of 2-pyridinemethyl-triphenylphosphonium bromide and 26.5 mg (0.0458 mmol) of Compound b to give 47.3 mg of diacetylated Compound 7.

FAB-MS (m/z); 655 (M+1)$^+$

The same procedure as in Example 1, Step B was repeated using 47.3 mg of diacetylated Compound 7 to give 13.3 mg (yield from Compound b: 51%) of Compound 7.

$^1$H-NMR (DMSO-d$_6$) δ; 2.05 (dd, 1H, J=5.0, 14.1 Hz), 2.16 (s, 3H), 3.42 (dd, 1H, J=7.3, 14.1 Hz), 3.94 (s, 3H), 5.00 (d, 1H, J=18.0 Hz), 5.06 (d, 1H, J=18.0 Hz), 6.35 (s, 1 H), 7.17 (dd, 1H, J=5.0, 7.3 Hz),7.23–7.97 (m, 8H), 7.30 (d, 1H, J=16.0 Hz), 7.89 (d, 1H, J=16.0 Hz), 8.07 (d, 1H, J=7.3 Hz), 8.59 (m, 1H), 8.67 (s, 1H), 9.46 (d, 1H, J=1.2 Hz).

FAB-MS (m/z); 571 (+1)$^+$

Example 8
Synthesis of Compound 8

The same procedure as in Example 5 was repeated using 244 mg (0.561 mmol) of 2-pyridinemethyl-triphenylphosphonium bromide and 50.0 mg (0.0824 mmol) of Compound a to give 75.3 mg of diacetylated Compound 8.

FAB-MS (m/z); 757 (M)$^+$

The same procedure as in Example 1, Step B was repeated using 75.3 mg of diacetylated Compound 8 to give 22.6 mg (yield from Compound a: 41%) of Compound 8.

$^1$H-NMR (DMSO-d$_6$)δ; 2.06 (dd, 1H, J=5.0, 14.4 Hz), 2.18 (s, 3H), 3.43 (dd, 1H, J=7.6, 14.4 Hz), 3.95 (s, 3H), 5.08–5.17 (m, 2H), 6.42 (s, 1H), 7.19 (dd, 1H, J=5.0, 7.6 Hz), 7.30 (d, 1H, J=16.0 Hz), 7.42 (d, 1H, J=16.0 Hz), 7.22–9.46 (m, 17H).

FAB-MS (m/z); 674 (M+1)$^+$

Example 9

Synthesis of Compound 9

To a solution of 36.9 mg (0.0550 mmol) of Compound 6 in 4 ml of N,N-dimethylformamide was added 25 mg of 10% Pd/C, followed by stirring at 60° C. for 2 hours in an atmosphere of hydrogen. After insoluble materials in the reaction mixture were filtered off, the solvent was evaporated under reduced pressure. The residue was purified by silica gel column chromatography (chloroform) to give 31.1 mg (84%) of Compound 9.

$^1$H-NMR (DMSO-$d_6$) δ; 1.98 (dd, 1H, J=5.1, 14.1 Hz), 2.12 (s, 3H), 2.99–3.14 (m,8H), 3.36 (dd, 1H, J=7.5, 14.1 Hz), 3.92 (s, 3H), 4.92 (d,1H, J=17.6 Hz), 4.97 (d, 1H, J=17.6 Hz), 6.28 (s, 1 H), 7.08 (dd, 1H, J=5.1, 7.5 Hz), 7.17–7.38 (m, 12H), 7.78–7.84 (m, 3H), 8.59 (s, 1H), 9.09 (m, 1H).

FAB-MS (m/z); 676 (M+1)$^+$

Example 10

Synthesis of Compound 10

The same procedure as in Example 9 was repeated using 43.6 mg (0.0766 mmol) of Compound 5 to give 24.2 mg (55%) of Compound 10.

$^1$H-NMR (DMSO-$d_6$)δ; 2.00 (dd, 1H, J=4.9, 14.1 Hz), 2.15 (s, 3H), 2.99–3.11 (m, 4H), 3.37 (dd, 1H, J=7.3, 14.1 Hz), 3.92 (s, 3H), 4.97 (d, 1H, J=17.9 Hz), 5.03 (d, 1H, J=17.9 Hz), 6.32 (s, 1 H), 7.10 (dd, 1H, J=4.9, 7.3 Hz), 7.17–8.06 (m, 11H), 8.58 (s, 1H), 9.11 (m, 1H).

FAB-MS (m/z); 572 (M+1)$^+$

Example 11

Synthesis of Compound 11

The same procedure as in Example 9 was repeated using 15.0 mg (0.0223 mmol) of Compound 8 to give 9.8 mg (65%) of Compound 11.

$^1$H-NMR (CDCl$_3$) δ; 2.19 (s, 3H), 2.42 (dd, 1H, J=4.8, 14.4 Hz), 3.21–3.29 (m, 8H), 3.31 (dd, 1H, J=7.5, 14.4 Hz), 4.08 (s, 3H), 4.19 (br,1H), 4.83 (d, 1H, J=16.2 Hz), 4.88 (d, 1H, J=16.2 Hz), 5.98 (s, 1H), 6.84 (dd, 1H, J=4.8, 7.5 Hz), 7.11–7.33 (m, 7H), 7.56–7.62 (m,2H), 7.68 (s, 1H), 7.73 (d, 1H, J=8.6 Hz), 8.58–8.61 (m, 2H), 9.08 (m, 1H).

FAB-MS (m/z); 678 (M+1)$^+$

Example 12

Synthesis of Compound 12

The same procedure as in Example 1, Step A was repeated using 25.0 mg (0.0432 mmol) of Compound C obtained in Reference Example 3 and 52.0 mg (0.156 mmol) of ethyl (triphenylphosphoranylidene)acetate to give 17.2 mg (63%) of diacetylated Compound 12.

FAB-MS (m/z); 650 (M+1)$^+$

The same procedure as in Example 1, Step B was repeated using diacetylated Compound 12 to give 8.1 mg (54%) of Compound 12.

$^1$H-NMR (DMSO-$d_6$) δ; 1.31 (t, 3 H, J=7.1 Hz), 2.00 (dd, 1H, J=4.9, 14.1 Hz), 2.15 (s, 3H), 3.41 (dd, 1H, J=7.3, 14.1 Hz), 3.93 (s, 3H), 4.23 (q, 2H, J=7.1 Hz), 5.08 (s, 2H), 6.41 (s, 1H), 6.76 (d, 1H, J=15.9 Hz), 7.16 (dd, 1H, J=4.9, 7.3 Hz), 7.93 (d, 1H, J=15.9 Hz), 7.28–7.96 (m,4H), 8.39 (s, 1H), 8.71 (s, 1H), 9.23 (d, 1H, J=7.8 Hz).

FAB-MS (m/z); 566 (M+1)$^+$

Example 13

Synthesis of Compound 13

The same procedure as in Example 5 was repeated using 118 mg (0.855 mmol) of 2-pyridinemethyl-triphenylphosphonium bromide and 39.6 mg (0.0684 mmol) of Compound C obtained in Reference Example 3 to give diacetylated Compound 13.

FAB-MS (m/z); 655 (M+1)$^+$

The same procedure as in Example 1, Step B was repeated using diacetylated Compound 13 to give 30.0 mg (yield from Compound C: 77%) of Compound 13 (E/Z=8/2).

$^1$H-NMR (DMSO-$d_6$)δ; 2.02 (dd, 1H, J=4.9, 14.1 Hz), 2.13 (s, 0.6H), 2.17 (s, 2.4H), 3.41 (dd, 1H, J=7.3, 14.1 Hz), 3.92 (s, 0.6 H), 3.94 (s, 2.4H), 5.03 (d, 0.8H, J=18.8 Hz), 5.13 (d, 0.8H, J=18.8 Hz), 6.35 (s, 0.2H), 6.39 (s, 0.8 H), 6.69 (d, 0.2H, J=12.9 Hz), 6.98 (d, 0.2H, J=12.9 Hz), 7.15 (dd, 1H, J=4.9, 7.3 Hz), 7.24–7.97 (m, 8 H), 7.42(d, 0.8H, J=16.0 Hz), 7.96 (d, 0.8H, J=16.0 Hz), 8.23 (s, 0.2H), 8.30 (s, 0.8H), 8.60 (n 1H), 8.70 (s, 1H), 9.18 (d, 0.2H, J=7.8 Hz), 9.23 (d, 0.8H, J=7.8 Hz).

FAB-MS (m/z); 571 (M+1)$^+$

Example 14

Synthesis of Compound 14

The same procedure as in Example 9 was repeated using 19.9 mg (0.0349 mmol) of Compound 13 to give 16.4 mg (82%) of Compound 14.

$^1$H-NMR (CDCl$_3$)δ; 1.99 (dd, 1H, J=4.9, 14.2 Hz), 2.13 (s, 3H), 3.16–3.24 (m, 4H), 3.38 (dd, 1H, J=7.4, 14.2 Hz), 3.92 (s, 3H), 4.30 (d, 1H, J=17.4 Hz), 4.98 (d, 1H, J=17.4 Hz), 6.29 (s, 1H), 7.12 (dd, 1H, J=4.9, 7.4 Hz), 7.21–7.89 (m, 9H), 8.55 (m, 1H), 8.61 (s, 1H), 9.21 (d, 1H, J=7.6 Hz).

FAB-MS (m/z); 573 (M+1)$^+$

Example 15

Synthesis of Compound 15

The same procedure as in Example 5 was repeated using 144 mg (0.331 mmol) of 2-pyridmemethyl-triphenylphosphonium bromide and Compound E obtained in Reference Example 5 to give 36.3 mg (yield from Compound D: 62%) of Compound 15 (E/Z =9/1).

$^1$H-NMR (CDCl$_3$) δ; 1.81 (s, 0.3H), 1.84 (s, 2.7H), 2.25 (dd, 1H, J=5.2, 14.7 Hz), 2.29 (s, 0.3H), 2.33 (s, 2.7H), 2.65 (s, 2.7H), 2.68 (s, 0.3H), 4.01 (s, 0.3H), 4.04 (s, 2.7H), 4.07 (dd, 1H, J=7.6, 14.7 Hz), 5.08 (m, 0.2H), 5.34 (m, 1.8H), 6.81 (d, 0.1H, J=12.6 Hz), 6.98 (dd, 1H, J=5.2, 7.6 Hz), 7.19 (m, 1H), 7.32 (d, 0.9H, J=16.1 Hz), 7.87 (d, 1H, J=16.1 Hz) 7.95 (d, 1H, J=8.8 Hz), 8.13 (m, 1H), 8.35 (m, 1H), 8.66 (m, 1H), 9.93 (m, 1H).

FAB-MS (m/z); 700 (M+1)$^+$

Example 16

Synthesis of Compound 16

The same procedure as in Example 1, Step B was repeated using 33.1 mg (0.0474 mmol) of Compound 15 to give 24.5 mg (84%) of Compound 16 (E/Z=9/1).

FAB-MS (m/z); 616 (M+1)$^+$ $^1$H-NMR (DMSO-$d_6$)δ; 2.13 (dd, 1H, J=5.0, 14.3 Hz), 2.18 (s, 3H), 3.47 (dd, 1H, J=7.5, 14.3 Hz), 3.93 (s, 0.3H), 3.95 (s, 2.7H), 5.13 (d, 0.9H, J=18.1 Hz), 5.18 (d, 0.9H, J=18.1 Hz), 6.45 (s, 0.1 H), 6.49 (s, 0.9 H), 6.71 (d, 0.1H, J=12.6 Hz), 6.99 (d, 0.1H, J=12.6 Hz), 7.30 (dd, 1H, J=5.0, 7.5 Hz), 7.24–8.60 (m, 9 H), 7.43 (d, 0.9H, J=16.0 Hz), 7.96 (d, 0.9H, J=16.0 Hz), 8.74 (s, 0.1H), 8.88 (s, 0.9H), 10.14 (d, 0.1H, J=2.4 Hz), 10.17 (d, 0.9H, J=2.4 Hz).

Example 17

Synthesis of Compound 17

Compound 15 (133 mg 0.190 mmol) was subjected to catalytic reduction in the same manner as in Example 9 to give 93.2 mg (73%) of Compound 17.

¹H-NMR (DMSO-d₆) δ; 1.68 (s, 3H), 2.09 (dd, 1H, J=4.9, 14.6 Hz), 2.18 (s, 3H), 2.71 (s, 3H), 3.15–3.21 (m, 2H), 3.82 (dd, 1H, J=7.4, 14.6 Hz), 3.93 (s, 3H), 4.97 (br, 2H), 5.35 (s, 2H), 7.11 (dd, 1H, J=4.2,7.4 Hz), 6.90–7.87 (m, 8H), 8.32 (d, 1H, J=2.2 Hz), 8.55 (m, 1H).

FAB-MS (m/z); 672 (M+1)⁺

Example 18

Synthesis of Compound 18

The same procedure as in Example 1, Step B was repeated using 23.6 mg (0.0352 mmol) of Compound 17 to give 16.3 mg (79%) of Compound 18.

FAB-MS (m/z); 588 (M+1)⁺

Example 19

Synthesis of Compound 19

To a solution of 66.2 mg (0.0987 mmol) of Compound 17 in 4 ml of chloroform were added 0.02 ml of triethylamine and 0.1 ml of ethyl isocyanate, followed by stirring at room temperature for 2 hours. After addition of water, the reaction mixture was extracted with chloroform. The organic layer was washed with a saturated aqueous solution of sodium chloride and dried over magnesium sulfate. The solvent was evaporated under reduced pressure, and the residue was purified by silica gel column chromatography (chloroform/methanol=99/1–98/2) to give 68.7 mg (94%) of diacetylated Compound 19.

FAB-MS (m/z); 743 (M+1)⁺

The same procedure as in Example 1, Step B was repeated using 25.5 mg (0.0344 mmol) of diacetylated Compound 19 to give 17.7 mg (78%) of Compound 19.

¹H-NMR (DMSO-d₆) δ; 1.08 (t, 3H, J=7.1 Hz), 1.94 (dd, 1H, J=4.6, 14.1 Hz), 2.11 (s, 3H), 3.10–3.22 (m, 4H), 3.34 (dd, 1H J=7.2, 14.1 Hz), 3.90 (s, 3H), 4.90 (d, 1H, J=17.5 Hz), 4.96 (d, 1H, J=17.5 Hz),6.00 (t, 1H, J=5.4 Hz), 6.26 (s,1H), 7.03 (dd, 1H, J=4.6, 7.2 Hz),7.22–7.86 (m, 8 H), 8.43 (s, 1H), 8.55 (m, 1H), 8.58 (s, 1H), 8.84 (d, 1H, J=2.2 Hz).

FAB-MS (m/z); 659 (M+1)⁺

Example 20

Synthesis of Compound 20

To a solution of 40 mg (0.05 mmol) of Compound F obtained in Reference Example 6 in 3 ml of a dichloromethane/diethylamine mixture (2/1) were added 26 mg (0.025 mmol) of palladium(II) acetate, 13 mg (0.05 mmol) of triphenylphosphine and 9.5 mg (0.05 mmol) of cuprous iodide in a steam of argon, followed by stirring at room temperature for 10 minutes. After addition of 0.16 ml (1.5 mmol) of N,N-dimethylpropargylamine, the mixture was stirred at room temperature for one hour. The solvent was evaporated under reduced pressure, and the residue was purified by silica gel column chromate by (chloroform/methanol=96/4) to give 15.1 mg (42%) of diacetylated Compound 20.

FAB-MS (m/z); 714 (M+1)⁺

The same procedure as in Example 1, Step B was repeated using 6.5 mg (0.0091 mmol) of diacetylated Compound 20 to give 2.0 mg (35%) of Compound 20.

¹H-NMR (CDCl₃) δ; 2.14 (s, 3H), 2.46 (s, 6H), 2.48 (s, 6H), 3.05 (dd, 1H, J=4.5, 14.4 Hz), 3.55 (s, 2H), 3.56 (s, 2H), 3.62 (dd, 1H, J=7.5,14.4 Hz), 4.08 (s, 3H), 4.54 (d, 1H, J=16.9 Hz), 4.70 (d, 1H, J=16.9 Hz), 5.33 (m, 2H), 6.76 (dd, 1H, J=4.5, 7.5 Hz), 7.15 (d, 1H, J=8.5 Hz), 7.34 (dd, 1H, J=1.3, 8.5 Hz), 7.61 (dd, 1H, J=1.3, 8.5 Hz), 7.91 (d, 1H, J=8.8 Hz), 7.96 (d, 1H, J=0.97 Hz), 8.85 (s, 1H).

FAB-MS (m/z); 630 (M+1)⁺

Example 21

Synthesis of Compound 21 and Compound 22

A mixture of 2.2 mg (0.01 mmol) of palladium(II) acetate, 5.0 mg (0.02 mmol) of triphenylphosphine and 1 ml of dichloromethane was stirred at room temperature for 5 minutes in a stream of argon. To the mixture was added a solution of 72 mg (0.1 mmol) of Compound G obtained in Reference Example 7 and 3.8 mg (0.02 mmol) of cuprous iodide in 3 ml of a dichloromethane/diethylamine mixture (2/1), followed by stirring at room temperature for 10 minutes. After addition of 0.056 ml (1 mmol) of 1-methoxy-2-propyne, the mixture was stirred at room temperature for 1.5 hours. The solvent was evaporated under reduced pressure, and the residue was purified by silica gel column chromatography (chloroform) to give 23.0 mg (38%) of Compound 21 and 2.6 mg (4.3%) of Compound 22.

Compound 21

¹H-NMR (CDCl₃) δ; 2.15 (s, 3H), 3.13 (dd, 1H, J=4.5, 14.7 Hz), 3.57 (s, 3H), 3.79 (dd, 1H, J=7.7, 14.7 Hz), 4.09 (s, 3H), 4.46 (s, 2H), 4.53 (d, 1H, J=6.6 Hz), 4.58 (d, 1H, J=6.6 Hz), 5.11 (s, 1H), 5.69 (s, 1H), 6.77 (dd, 1H, J=4.5, 7.7 Hz), 7.10 (d, 1H, J=8.6 Hz), 7.46 (dd, 1H, J=1.7, 8.3 Hz), 7.63 (dd, 1H, J=1.5, 8.5 Hz), 7.92 (d, 1H, J=8.8 Hz), 7.98 (d, 1H, J=1.2 Hz), 8.83 (d, 1H, J=1.5 Hz).

FAB-MS (m/z) ; 703 (M+1)⁺

Compound 22

¹H-NMR (CDCl₃) δ; 2.15 (s, 3H), 2.95 (dd, 1H, J=4.9, 14.7 Hz), 3.54 (s, 3H), 3.55 (s, 3H), 3.60 (dd, 1H, J=7.6, 14.7 Hz), 4.09 (s, 3H), 4.42 (s, 2H), 4.45 (s, 2H), 4.53 (d, 1H, J=17.0 Hz), 4.70 (d, 1H, J=17.0 Hz), 5.19 (br, 1H), 5.32 (br, 1H), 6.78 (dd, 1H, J=4.9, 7.6 Hz), 7.20 (d, 1H, J=8.3 Hz), 7.36 (dd, 1H, J=1.5, 8.3 Hz), 7.61 (dd, 1H, J=1.7, 8.8 Hz), 7.89 (d, 1H, J=8.5Hz), 7.97 (d, 1H, J=1.5 Hz), 8.85 (d, 1H, J=1.0 Hz).

FAB-MS (m/z) ; 603 (M+1)⁺

Example 22

Synthesis of Compound 23

To a solution of 40 mg (0.05 mmol) of Compound F obtained in Reference Example 6 in 3 ml of a dichloromethane/diethylamine mixture (2/1) were added 126 mg (0.18 mmol) of bis(triphenylphosphine)palladium (II) chloride and 42 mg (0.22 mmol) of cuprous iodide in a stream of argon, followed by stirring at room temperature for 20 minutes. After addition of 0.16 ml (1.5 mmol) of propargyl alcohol, the mixture was stirred at room temperature for one hour. The reaction mixture was filtered through Celite and the solvent was evaporated under reduced pressure. The residue was purified by silica gel column chromatography (chloroform/methanol=96/4) to give 456.0 mg (23%) of diacetylaed Compound 23.

FAB-MS (m/z) ; 659 (M+1)⁺

The same procedure as in Example 1, Step B was repeated using 30.0 mg of diacetlated Compound 23 to give 8.0 mg (33%) of Compound 23.

¹H-NMR (CD₃OD) δ; 1.90 (s, 1H), 1.93 (s, 1H), 2.14 (dd, 1H, J=5.0, 14.2 Hz), 2.19 (s, 3H), 3.41 (dd, 1H, J=7.5, 14.2 Hz), 4.01 (s, 3H), 4.78 (m, 4H), 4.98 (d, 1H, J=17.6 Hz), 5.03 (d, 1H, J=17.6 Hz), 7.02 (dd, 1H, J=5.0, 7.5 Hz), 7.35 (dt, 1H, J=0.7, 7.8 Hz), 7.49 (m, 2H), 7.63 (d, 1H, J=8.3 Hz), 7.97 (d, 1H, J=9.2 Hz) 7.99 (d, 1H, J=1.1,8.6 Hz), 9.26 (d, 1H, J =1.0 Hz).

FAB-MS (m/z) ; 576 (M+1)⁺

Example 23

Synthesis of Compound 24

Chloroacetyl chloride (0.95 ml, 10 mmol) was added to 5 ml of a suspension of 1.06 g (8 mmol) of aluminum chloride in dichloromethane, and the mixture was stirred at room temperature for 5 minutes. To the mixture was added dropwise 10 ml of a solution of 500 mg (1 mmol) of Compound c (Japanese Published Unexamined Patent Application No. 295588/88) in dichloromethane, followed by stirring at room temperature for 2.5 hours. The reaction mixture was poured into ice-cold water, followed by extraction with chloroform/methanol (9/1). The extract was washed with a saturated aqueous solution of sodium chloride and dried over magnesium sulfate. After evaporation of the solvent under reduced pressure, the resulting powder was mixed with 1 N hydrochloric acid. The re was stirred for one hour and then filtered. The filtrate was purified by silica gel column chromatography (chloroform) to give 270 mg (38%) of Compound 24.

$^1$H-NMR (CDCl$_3$) δ; 1.82 (s, 3H), 2.20 (dd, 1H, J=5.4, 14.5 Hz), 2.32 (s, 3H), 2.81 (s, 3H), 4.05 (s, 3H), 4.06 (dd, 1H, J=7.3, 14.5 Hz), 4.87 (dd, 1H, J=14.1, 15.6 Hz) 5.03 (d, 1H, J=14.1, 15.6 Hz), 5.45 (m, 2H), 7.03 (dd, 1H, J=5.1, 7.3 Hz), 7.61 (d, 1H, J=8.8 Hz), 8.02 (d, 1H, J=8.8 Hz), 8.21 (dd, 1H, J=1.7, 8.8 Hz), 8.27 (dd, 1H, J=1.7, 8.8 Hz), 8.63 (d, 1H, J=1.5 Hz), 9.87 (d, 1H, J =1.0 Hz).

FAB-MS (m/z); 704 (M+1)$^+$

Example 24

Synthesis of Compound 25

To 1.5 ml of a solution of 36 mg (0.05 mmol) of Compound 24 in chloroform was added 0.025 ml (0.25 mmol) of piperidine, and the mixture was refluxed for 2 hours. The solvent was evaporated under reduced pressure, and the residue was purified by silica gel column chromatography (chloroform/methanol=10/1) to give diacetylated Compound 25.

FAB-MS (m/z); 802 (M+1)$^+$

The same procedure as in Example 1, Step B was repeated using diacetylated Compound 25 to give 16 mg (42%) of Compound 25.

$^1$H-NMR (CDCl$_3$) δ; 1.42 (m, 4H), 1.56 (m, 8H), 2.07 (dd, 1H, J=4.8, 14.2 Hz), 2.18 (s, 3H), 2.56 (m, 8H), 3.45 (dd, 1H, J=7.5, 14.2 Hz), 3.86 (m, 4H), 3.94 (s, 3H), 5.12 (m, 2H), 6.48 (s, 1H), 7.25 (dd, 1H, J=4.8, 7.5 Hz), 8.02 (d, 2H, J=9.0 Hz), 8.14 (dd, 1H, J=1.7, 7.1 Hz), 8.16 (dd, 1H, J=1.7, 7.1 Hz), 8.78 (br, 1H), 8.84 (br, 1H), 9.99 (d, 1H, J=1.5 Hz).

FAB-MS (m/z) ; 718 (M+1)$^+$

Example 25

Synthesis of Compound 26 and Compound 27

The same procedure as in Example 23 was repeated using 55 mg (0.1 mmol) of Compound c (Japanese Published Unexamined Patent Application No. 295588/88) and 3-chloropropionyl chloride to give 4 mg (6%) of Compound 26 and 26 mg (36%) of Compound 27.

Compound 26

FAB-MS (m/z); 642 (M+1)$^+$

Compound 27

FAB-MS (m/z); 732 (M+1)$^+$

Example 26

Synthesis of Compound 28

To 1.5 ml of a solution of 200 mg (0.25 mmol) of Compound 26 in chloroform was added 0.025 ml (0.25 mmol) of piperidine, and the mixture was refluxed for 2 hours. The solvent was evaporated under reduced pressure, and the residue was purified by silica gel column chromatography (chloroform/methanol=10/1) to give diacetylated Compound 28.

FAB-MS (m/z); 689 (M+1)$^+$

The same procedure as in Example 1, Step B was repeated using diacetylated Compound 28 to give 17 mg (11%) of Compound 28.

$^1$H-NMR (CDCl$_3$) δ; 1.48 (br, 2H), 1.65 (t, 4H, J=5.2 Hz), 2.18 (s, 3H), 2.47 (br, 4H), 2.60 (br, 1H), 3.00(br, 1H), 3.57 (dd, 1H, J=8.1, 15.4 Hz), 4.07 (s, 3H), 4.15 (d, 1H, J=15.4 Hz), 4.40 (d, 1H, J=15.8 Hz), 5.73 (br, 2H), 6.71 (dd, J=4.6, 7.3 Hz),7.02 (d, 1H, J=8.1 Hz), 7.30 (dd, 1H, J=5.2, 8.1 Hz), 7.43 (dd, 1H, J=5.2, 8.2 Hz), 7.56 (br, 1H), 7.63 (br, 1H), 7.88 (d, 1H, J=8.2 Hz), 8.84 (s, 1H).

FAB-MS (m/z) ; 605 (M+1)$^+$

Example 27

Synthesis of Compound 29

To 1.5 ml of a solution of 60 mg (0.03 mmol) of Compound 27 in chloroform was added 0.025 ml (0.25 mmol) of piperidine, and the mixture was refluxed for 2 hours. The solvent was evaporated under reduced pressure, and the residue was purified by silica gel column chromatography (chloroform/methanol=10/1) to give diacetylated Compound 29.

FAB-MS (m/z); 830 (M+1)$^+$

The same procedure as in Example 1, Step B was repeated using diacetylated Compound 29 to give 5.1 mg (8.3%) of Compound 29.

$^1$H-NMR (DMSO-d$_6$) δ; 2.06 (dd, 4H, J=4.4, 13.9 Hz), 2.17 (s, 3H), 2.49 (br, 12H), 3.29 (br, 4H), 3.44 (dd, 1H, J=7.3, 13.9 Hz), 3.93 (s, 3H), 5.13 (d, 1H, J=18.4 Hz), 5.80(d, 1H, J=18.4 Hz), 6.48(m, 1H), 7.25 (dd, 1H, J=5.4, 6.3 Hz), 8.00–8.16 (m, 4H), 8.62 (br, 1H), 8.77 (br, 1H), 9.96 (s, 1H).

FAB-MS (m/z); 746 (M+1)$^+$

Example 28

Synthesis of Compound 30

To 1.5 ml of a solution of 40 mg (0.05 mmol) of Compound 27 in chloroform was added 0.02 ml (0.23 mmol) of morpholine, and the mixture was refluxed for 2 hours. The solvent was evaporated under reduced pressure, and the residue was purified by silica gel column chromatography (chloroform/methanol=10/1) to give diacylated Compound 30.

FAB-MS (m/z); 834 (M+1)$^+$

The same procedure as in Example 1, Step B was repeated using diacetylated Compound 30 to give 35.5 mg (31%) of Compound 30.

$^1$H-NMR (DMSO-d$_6$) δ; 2.07 (dd, 1H, J=5.0, 14.7 Hz), 2.16 (s, 3H), 2.45 (m, 8H), 2.77 (br, 4H), 3.30 (m, 4H), 3.44 (dd, 1H, J=7.5, 14.7 Hz), 3.59 (m, 8H), 3.93 (s, 3H), 5.16 (m, 2H), 6.48 (s, 1H), 7.24 (dd, 1H, J=5.0, 7.5 Hz), 8.02 (dd, 1H, J=2.2, 5.5 Hz), 8.11 (dd, 1H, J=1.7, 5.8 Hz), 8.14 (dd, 1H, J=1.7, 5.8 Hz), 8.61 (d, 1H, J=1.0 Hz), 8.76 (br, 1H), 9.96 (d, 1H, J=1.2 Hz).

FAB-MS (m/z); 750 (M+1)$^+$

Example 29

Synthesis of Compound 31

To 3 ml of a solution of 100 mg (0.14 mmol) of Compound 24 in chloroform was added 1 ml of morpholine, and the mixture was refluxed for 3 hours. The solvent was evaporated under reduced pressure, and the residue was purified by silica gel column chromatography (chloroform/methanol=15/1) to give diacetylated Compound 31.

FAB-MS (m/z); 806 (M+1)$^+$

The same procedure as in Example 1, Step B was repeated using diacetylated Compound 31 to give 27 mg (26%) of Compound 31.

$^1$H-NMR (DMSO-d$_6$) δ; 2.06 (dd, 1H, J=5.0, 14.1 Hz), 2.62 (m, 8H), 3.45 (dd, 1H, J=7.3, 14.1 Hz), 3.63 (m, 8H), 3.91 (m, 2H), 3.98 (m, 2H), 5.13 (d, 2H, J=7.3 Hz), 6.49 (s, 1H), 7.25 (dd, 1H, J=5.0, 7.3 Hz), 8.02 (d, 1H, J=8.9 Hz), 8.13 (dd, 1H, J=1.7, 9.0 Hz), 8.15 (dd, 1H, J=1.7, 8.8 Hz), 8.62 (d, 1H, J=1.7 Hz), 8.77 (s, 1H), 8.78 (d, 1H, J=1.5 Hz), 10.01 (dd, 1H, J=0.49, 1.2 Hz)

FAB-MS (mlz) ; 722 (M+1)$^+$

Example 30
Synthesis of Compound 32

To 3 ml of a solution of 110 mg (0.16 mmol) of Compound 24 in N,N-dimethylformamide was added 54 ml of a 50% aqueous solution of dimethylamine, and the mixture was refluxed for 3 hours. The solvent was evaporated under reduced pressure, and the residue was purified by silica gel column chromatrography (chloroform/methanol=10/1) to give 13.7 mg (14%) of Compound 32.

$^1$H-NMR (DMSO-d$_6$) δ; 2.06 (dd, 1H, J=4.9, 14.1 Hz), 2.18 (s, 3H), 2.35 (s, 6H), 2.36 (s, 6H), 3.40 (dd, 1H, J=7.5, 14.1 lHz), 3.87 (m, 2H), 3.93 (m, 2H), 3.94 (s, 3H), 5.13 (m, 2H), 6.47 (s, 1H), 7.25 (dd, 1H, J=4.9, 7.5 Hz), 8.01 (d, 2H, J=9.0 Hz), 8.13 (dd, 1H, J=1.7, 5.6 Hz), 8.16 (dd, 1H, J=1.7, 5.4 Hz), 8.69 (d, 1H, J=1.7 Hz), 8.76 (br, 1H), 9.97 (d, 1H, J=1.2 Hz).

FAB-MS (m/z); 638 (M+1)$^+$

Example 31
Synthesis of Compounds 33a and 33b

To a suspension of 1.06 g (8.0 mmol) of aluminum chloride in 10 ml of methylene chloride was added 0.48 ml (5.0 mmol) of chloroacetyl chloride, and the mixture was stirred at room temperature for 5 minutes. To the mixture was gradually added a solution of 551 mg (1.0 mmol) of Compound c in 10 ml of methylene chloride, followed by stirring for 2.5 hours. The reaction mixture was then poured into ice-cold water, followed by extraction with chloroform/methanol (9/1). The extract was washed with a saturated aqueous solution of sodium chloride and dried over sodium sulfite. After evaporation of the solvent under reduced pressure, the resulting powder was mixed with 1 N hydrochloric acid. The mixture was stirred for one hour, and then insoluble materials were removed by filtration. The filtrate was purified by silica gel column chromatography (chloroform) to give 110 mg (17%) of a mixture of Compounds 33a and 33b.

Compound 33a

FAB-MS (m/z); 628, 630 (M+1)$^+$

Compound 33b

FAB-MS (m/z); 628, 630 (M+1)$^+$

Example 32
Synthesis of Compound 34

To a solution of 64 mg (0.1 mmol) of a mixture of Compounds 33a and 33b in 1.5 ml of N,N-dimethylformamide were added 30 mg (0.2 mmol) of sodium iodide and 1 ml of a 50% aqueous solution of dimethylamine, followed by reflux for 2 hours. The solvent was evaporated under reduced pressure, and the residue was purified by silica gel column chromatography (chloroform/methanol=9/1) to give 3.2 g (5.8%) of Compound 34.

$^1$H-NMR (CDCl$_3$) δ; 1.73 (br, 1H), 2.20 (s, 3H), 2.44 (s, 6H), 2.85 (dd, 1H, J=4.9, 13.7 Hz), 3.61(dd, 1H, J=7.8, 13.7 Hz), 3.70 (m, 2H), 4.09 (s, 3H), 4.50 (d, 1H, J=16.6 Hz), 4.70 (d, 1H, J=16.6 Hz), 5.70 (br, 1H), 6.85 (dd, 1H, J=4.9, 7.3 Hz), 7.29 (d, 1H, J=8.3 Hz), 7.39 (t, 1H, J=7.6 Hz), 7.51 (t, 1H, J=7.6 Hz), 7.83(t, 1H, J=7.6 Hz), 7.89 (d, 1H, J=8.3 Hz),7.90 (d, 1H, J=7.6 Hz), 9.36 (s, 1H).

FAB-MS (m/z); 553 (M+1)$^+$

Example 33
Synthesis of Compound 35

To a solution of 63 mg (0.1 mmol) of a mixture of Compounds 33a and 33b in 2 ml of N,N-dimethylformamide was added 90 mg (0.6 mmol) of sodium iodide, and the mixture was then stirred at room temperature for 2 hours. After the solvent was evaporated under reduced pressure, the residue was treated in the same manner as in Example 1, Step B to give 6.8 mg (12%) of Compound 35.

$^1$H-NMR (DMSO-d$_6$) δ; 2.00–2.40 (m, 7H), 2.70–2.80 (m,4H), 3.40 (br, 1H), 3.94 (s, 3H), 4.22 (br, 2H)),5.02 (d, 1H, J=18.0 Hz), 5.07 (d, 1H, J=18.0 Hz), 6.42 (s, 1H), 6.90 (br, 1H), 7.38 (t, 1H, J=7.5 Hz), 7.51 (dd, 1H, J=7.5, 8.5 Hz), 7.95(d, 1H, J=8.5 Hz), 8.00 (d, 1H, J=8.7 Hz), 8.08 (d, 1H, J=7.5 Hz), 8.12 (dd, 1H, J=1.7,8.7 Hz), 8.69 (s, 1H), 9.95 (d, 1H, J=1.4 Hz).

FAB-MS (m/z); 579 (M+1)$^+$

Example 34
Synthesis of Compounds 36a and 36b

The same procedure as in Example 28 was repeated using 40 mg (0.064 mmol) of a mixture of Compounds 33a and 33b to give 17 mg (40%) of Compound 36a and 10 mg (23%) of Compound 36b.

Compound 36a $^1$H-NMR (CDCl$_3$) δ; 1.80 (s, 3H), 2.18 (dd, 1H, J=5.1, 10.2 Hz), 2.29 (s, 3h), 2.77 (s, 3H), 3.07 (br,4H), 3.93 (br, 4H), 4.00 (dd, 1H, J=7.5, 10.1 Hz), 4.07 (s, 3H), 4.35 (br, 2H), 5.38 (d, 2H, J=5.4 Hz), 6.90 (m, 1H), 7.00 (dd, 1H, J=5.1,7.5 Hz), 7.46 (td, 1H, J=0.5, 7.5 Hz), 7.56 (d, 1H, J=8.5 Hz), 7.57 (td, 1H, J=1.1, 7.5 Hz),7.94 (d, 1H, J=8.5 Hz), 8.07 (d, 1H, J=7.5 Hz), 8.22 (dd, 1H, J=1.6, 7.5 Hz), 9.94 (br, 1H).

FAB-MS (m/z); 679 (M+1)$^+$

Compound 36b $^1$H-NMR (CDCl$_3$) δ; 1.80 (s, 3H), 2.15 (dd, 1H, J=5.1, 12.2 Hz), 2.29 (s, 3H), 2.79 (s, 3H), 2.94 (br,4H), 3.92 (t, 4H, J=4.5 Hz), 4.09 (dd, 1H, J=7.2, 12.2 Hz), 4.02 (s, 3H), 4.35 (br, 2H), 5.38(br, 2H), 7.03 (dd, 1H, J=5.1, 7.2 Hz), 7.38(br, 1H), 7.56 (br, 1H), 7.95 (d, 1H, J=8.9 Hz), 8.21 (d, 1H, J=1.7, 8.9 Hz), 8.78 (br 1H), 9.21 (d, 1H, J=8.0 Hz).

FAB-MS (m/z); 679 (M+1)$^+$

Example 35
Synthesis of Compound 37a

The same procedure as in Example 1, Step B was repeated using 17 mg (0.025 mmol) of Compound 36a to give 3.2 mg (22%) of Compound 37a.

$^1$H-NMR (DMSO-d$_6$) δ; 2.23 (s, 3H), 2.56 (dd, 1H, J=4.5, 14.7 Hz), 2.72 (br, 4H), 3.43 (dd, 1H, J=7.6, 14.7 Hz), 3.82 (t, 4H, J=4.6 Hz), 4.01(br, 1H), 4.11 (s, 3H), 4.86 (d, 1H, J=16.0 Hz), 4.95 (d, 1H, J=16.0 Hz), 5.96 (br, 1H) 6.91 (dd, 1H, J=4.8, 7.4 Hz), 7.41 (t, 1H, J=7.6 Hz), 7.50 (d, 1H, J=7.6 Hz), 7.51 (t, 1H, J=7.6 Hz), 7.85 (d, 1H, J=8.6 Hz), 7.92 (d, 1H, J=7.6 Hz), 8.11 (d, 1H, J=8.6 Hz), 9.81 (br, 1H).

FAB-MS (m/z); 595 (M+1)$^+$

Example 36
Synthesis of Compound 37b

The same procedure as in Example 1, Step B was repeated using 10 mg (0.015 mmol) of Compound 36b to give 1.0 mg (11%) of Compound 3 7b.

$^1$H-NMR (DMSO-d$_6$) δ; 2.23 (s, 3H), 2.42 (dd, 1H, J=4.9,14.5 Hz), 2.64 (br, 4H), 3.35 (dd, 1H, J=7.6, 14.5 Hz), 3.80 (t, 4H, J=4.6 Hz), 3.85 (d, 2H, J=5.3 Hz), 4.12 (s, 3H), 4.29 (br, 1H), 4.80 (d, 1H, J=16.5 Hz), 4.90 (d, 1H, J=16.5 Hz), 6.21 (br, 1H), 6.93 (dd, 1H, J=4.9, 7.4 Hz), 7.30 (br, 1H), 7.49 (m, 2H), 7.83 (d, 1H, J=8.9 Hz), 8.11 (d, 1H, J=8.9 Hz), 8.55 (s, 1H), 8.5(s, 1H), 9.20 (d, J=8.1 Hz, 1H).

FAB-MS (m/z); 595 (M+1)$^+$

Example 37
Synthesis of Compound 38

The same procedure as in Example 33 was repeated using 162 mg (0.23 mmol) of Compound 24 to give 32 mg (46%) of Compound 38.

$^1$H-NMR (DMSO-$d_6$) δ; 1.95 (s, 3H), 2.30 (m, 9H), 2.65 (m, 8H), 3.45 (dd, 1H, J=7.1, 14.4 Hz), 3.94 (s, 3H), 4.13 (m, 4H), 5.12 (m, 2H), 6.52 (s, 1H), 7.24 (dd, 1H, J=4.9, 7.3 Hz), 8.02 (d, 2H, J=8.8 Hz), 8.29 (m, 2H), 8.72 (s, 1H), 8.76(br, 1H) 9.97 (s, 1H).

FAB-MS (m/z); 689 (M+1)$^+$

Example 38
Synthesis of Compound 39

To a solution of 211 mg (0.30 mmol) of Compound 24 in 2 ml of N,N-dimethylformamide were added 300 mg (3.0 mmol) of N-methylpiperazine and 90 mg (0.6 mmol) of sodium iodide, and the mixture was stirred at room temperature for 2 hours. After the solvent was evaporated under reduced pressure, the residue was purified by silica gel column chromatography (chloroform/methanol=9/1) to give 190 mg (76%) of Compound 39.

FAB-MS (m/z); 832 (M+1)$^+$

Example 39
Synthesis of Compound 40

The same procedure as in Example 1, Step B was repeated using 17 mg (0.02 mmol) of Compound 39 to give 5.1 mg (34%) of Compound 40.

$^1$H-NMR (DMSO-$d_6$) δ; 2.06 (dd, J=4.6, 14.4 Hz, 4H), 2.18 (s, 3H), 2.30 (br, 6H), 2.50 (br, 8H), 2.67 (br, 8H), 3.45 (dd, 1H, J=7.1, 14.4 Hz), 3.94 (s, 3H), 3.98 (br, 4H), 5.13 (br, 2H)), 6.49 (s, 1H), 7.25 (dd, 1H, J=4.6, 7.1 Hz), 8.02 (d, 2H, J=8.5 Hz), 8.13 (dd, 1H, J=1.7, 6.8 Hz), 8.16 (dd, 1H, J=1.7, 6.8 Hz), 8.78 (br, 2H), 9.99 (d, 1H, J=1.7 Hz).

FAB-MS (m/z); 748 (M+1)$^+$

Example 40
Synthesis of Compound 41

To a solution of 50 mg (0.078 mmol) of a mixture of Compounds 33a and 33b in 2 ml of methylene chloride was added 66 mg (0.78 mmol) of sodium ethanethiolate, and the mixture was stirred at room temperature for 3 hours. The reaction mixture was poured into ice-cold water, followed by extraction with chloroform/methanol. The extract was washed with a saturated aqueous solution of sodium chloride and dried over sodium sulfate. After evaporation of the solvent under reduced pressure, the residue was purified by silica gel column chromatography (chloroform/methanol= 99.8/0.2) to give 17.0 mg (33%) of diacetylated compound 41.

FAB-MS (m/z); 654 (M+1)$^+$

The same procedure as in Example 1, Step B was repeated using 17 mg (0.026 mmol) of diacetylated Compound 41 to give 5.3 mg (35%) of Compound 41.

$^1$H-NMR (DMSO-$d_6$) δ; 1.23 (t, 3H, J=7.3 Hz), 2.00 (dd, 1H, J=4.7, 13.9 Hz), 2.33 (s, 3H), 2.59 (q, 2H, J=7.3 Hz), 3.42 (dd, 1H, J=7.3, 13.9 Hz), 3.94 (s, 3H), 4.19 (d, 2H, J=3.4 Hz), 5.10 (d, 2H, J=5.1 Hz), 6.44 (br, 1H), 7.18 (dd, 1H, J=4.9, 7.3 Hz), 8.31 (t, 1H, J=8.2 Hz), 7.51 (dt, 1H, J=1.4, 8.3 Hz), 7.92 (d, 1H, J=8.2 Hz), 8.02 (d, 1H, J=9.0 Hz), 8.11 (dd, 1H, J=1.9, 9.0 Hz), 8.63 (d, 1H, J=1.4 Hz), 8.72 (br, 1H), 9.23 (d, 1H, J=8.1 Hz).

FAB-MS (m/z); 570 (M+1)$^+$

Example 41
Synthesis of Compounds 42a and 42b

To a solution of 100 mg (0.16 mmol) of a mixture of Compounds 33a and 33b in 2 ml of N,N-dimethylformamide were added 100 mg (0.9 mmol) of 4-mercaptopyridine and 22 mg (0.16 mmol) of potassium carbonate, followed by stirring at room temperature for 2 hours. The reaction mixture was poured into ice-cold water, followed by on with chloroform/methanol. The extract was washed with a saturated aqueous solution of sodium chloride and dried over sodium sulfate. After evaporation of the solvent under reduced pressure, the residue was purified by silica gel column chromatography (chloroform/methanol=99.8/0.2) to give 70 mg (63%) of a mixture of diacetylated Compounds 42a and 42b.

FAB-MS (m/z); 703 (M+1)$^+$

The same procedure as in Example 1, Step B was repeated using 70 mg (0.10 mmol) of the mixture of diacetylated compounds to give 3.3 mg (5.3%) of Compound 42a and 5.2 mg (8.4%) of Compound 42b.

Compound 42a $^1$H-NMR (DMSO-$d_6$) δ; 2.09 (dd, 1H, J=4.9, 13.9 Hz), 2.19 (s, 3H), 3.44 (dd, 1H, J=7.3, 13.9 Hz), 3.94 (s, 3H), 4.99 (s, 2H), 5.05 (d, 2H, J=5.9 Hz), 6.39 (s, 1H), 7.25 (dd, 1H, J=4.9, 7.3 Hz), 7.39 (t, 1H, J=8.6 Hz)7.41 (d, 1H, J=6.4 Hz), 7.52 (t, 1H, J=8.6 Hz), 7.96 (d, 1H, J=8.6 Hz), 8.071 (d, 1H, J=8.8 Hz), 8.074 (d, 1H, J=8.6 Hz), 8.25 (dd, 1H, J=1.7, 8.8 Hz), 8.40 (d, 2H, J=6.4 Hz), 8.71 (s, 1H), 9.98 (d, 1H, J=1.0 Hz).

FAB-MS (m/z); 619 (M+1)$^+$

Compound 42b $^1$H-NMR (CDCl$_3$) δ; 2.24 (s, 3H), 2.39 (dd, 1H, J=5.1, 14.4 Hz), 3.36 (dd, 1H, J=7.3, 14.4 Hz), 4.12 (s, 3H), 4.46 (d, 2H, J=3.4 Hz), 4.83 (d, 1H, J=16.4 Hz), 4.93 (d, 1H, J=16.4 Hz), 6.15 (s,1H), 6.93 (dd, 1H, J=4.9, 7.3 Hz), 7.11–7.29 (br, 5H), 7.22–7.58 (br, 2H), 7.86 (d, 1H, J=8.3 Hz), 8.04 (d, 1H, J=8.3 Hz), 8.48 (d, 1H, J=2.7 Hz), 8.51 (s, 1H), 9.22 (d, 1H, J=8.3 Hz).

FAB-MS (m/z); 619 (M+1)$^+$

Example 42
Synthesis of Compound 43

To a solution of 211 mg (0.30 mmol) of Compound 24 in 4 ml of chloroform/methanol (3/1) was added 56 mg (0.80 mmol) of sodium methanethiolate, followed by stirring at room temperature for 30 minutes. The reaction mixture was poured into ice-cold water, followed by extraction with chloroform/methanol. The extract was washed with a saturated aqueous solution of sodium chloride and dried over sodium sulfate. The solvent was evaporated under reduced pressure to give 125 mg (57%) of diacetylated Compound 43.

FAB-MS (m/z); 728 (M+1)$^+$

The same procedure as in Example 1, Step B was repeated using 125 mg (0.017 mmol) of diacetylated Compound 43 to give 48 mg (44%) of Compound 43.

$^1$H-NMR (DMSO-$d_6$) δ; 2.07 (dd, 1H, J=4.9, 14.4 Hz), 2.13 (s, 3H), 2.14 (s, 3H), 2.18 (s, 3H), 3.45 (dd, 1H, J=7.3, 14.4 Hz), 3.94 (s, 3H), 4.04 (s, 2H), 4.17 (d, 2H, J=2.9 Hz), 5.14 (d, 2H, J=4.6 Hz), 6.50 (br, 1H), 7.26 (dd, 1H, J=4.9, 7.3 Hz), 8.03 (d, 1H, J=8.8 Hz), 8.04 (d, 1H, J=8.8 Hz), 8.13 (dd, 1H, J=2.0, 8.8 Hz), 8.17 (dd, 1H, J=2.0, 8.8 Hz), 8.65 (d, 1H, J=1.7 Hz), 8.78 (br, 1H), 9.93 (d, 1H, J=1.5 Hz).

FAB-MS (m/z); 644 (M+1)$^+$

Example 43
Synthesis of Compound 44

To a solution of 50 mg (0.07 mmol) of Compound 24 in 2 ml of methylene chloride was added 59 mg (0.7 mmol) of sodium ethanethiolate, followed by stirring at room temperature for 3 hours. After the solvent was evaporated under reduced pressure, the residue was purified by silica gel column chromatography (chloroform/methanol=99.8/0.2) to give 19.7 mg (36%) of diacetylated Compound 44.

FAB-MS (m/z); 756 (M+1)$^+$

The same procedure as in Example 1, Step B was repeated using 19 mg (0.025 mmol) of diacetylated Compound 44 to give 12.5 mg (67%) of Compound 44.

$^1$H-NMR (DMSO-d$_6$) δ; 1.22 (t, 3H, J=7.5 Hz), 1.23 (t, 3H, J=7.5 Hz), 2.08 (dd, 1H, J=4.9, 13.9 Hz), 2.18 (s, 3H), 2.60 (br, 4H), 3.45 (dd, 1H, J=7.3, 13.9 Hz), 3.94 (s, 3H), 4.07 (br, 2H), 4.19 (d, 2H, J=4.2 Hz), 5.14 (br, 2H), 6.49 (br, 1H), 7.26 (dd, 1H, J=4.9, 7.3 Hz), 8.03 (d, 1H, J=9.0 Hz), 8.04 (dd, 1H, J=8.8 Hz), 8.13 (dd, 1H, J=1.7, 9.0 Hz), 8.16 (dd, 1H, J=2.0, 8.8 Hz), 8.65 (d, 1H, J=1.7 Hz), 8.79 (br, 1H), 9.94 (d, 1H, J=1.7 Hz).

FAB-MS (m/z); 672 (M+1)$^+$

Example 44
Synthesis of Compound 45

To a solution of 100 mg (0.16 mmol) of Compound 24 in 3.5 ml of N,N-dimethylformamide/methanol (6/1) were added 0.038 ml (0.32 mmol) of propanethiol and 44 mg (0.32 mmol) of potassium carbonate, followed by stirring at room temperature for 2 hours. The reaction mixture was poured into ice-cold water, followed by extraction with chloroform/methanol. The extract was washed with a saturated aqueous solution of sodium chloride and dried over sodium sulfate. After the solvent was evaporated under reduced pressure, the residue was purified by silica gel column chromatogaphy (chloroform/methanol=95/5) to give 32 mg (23%) of Compound 45.

$^1$H-NMR (DMSO-d$_6$) δ; 0.93 (t, 3H, J=7.3 Hz), 0.94 (t, 3H, J=7.3 Hz), 1.59 (qt, 2H, J=7.2, 7.3 Hz), 1.60 (tq, 2H, J=7.3, 7.2 Hz), 2.07 (dd, 1H, J=5.0, 13.1 Hz), 2.18 (s, 3H), 2.57 (t, 2H, J=7.2 Hz), 2.58 (t, 2H, J=7.2 Hz), 3.45 (dd, 1H, J=7.6, 13.1 Hz), 3.94 (s, 3H), 4.04 (s, 2H), 4.15 (d, 2H, J=5.1 Hz), 5.14 (d, 2H, J=8.0 Hz), 6.50 (br, 1H), 7.26 (dd, 1H, J=5.0, 7.3 Hz), 8.03 (d, 1H, J=8.9 Hz), 8.04 (d, 1H, J=8.7 Hz), 8.12 (dd, 1H, J=1.7, 8.9 Hz), 8.16 (dd, 1H, J=1.7, 8.7 Hz), 8.65 (d, 1H, J=1.6 Hz), 8.80 (br, 1H), 9.93 (d, 1H, J=1.6 Hz).

FAB-MS (m/z); 700 (M+1)$^+$

Example 45
Synthesis of Compound 46

To a solution of 70 mg (0.10 mmol) of Comnpound 24 in 3.5 ml of N,N-dimethylformamide/methanol (6/1) were added 23 mg (0.30 mmol) of 2-hydroxyethanethiol and 50 mg (0.36 mmol) of potassium carbonate, followed by stirring at room temperature for 1 day. The reaction mixture was poured into ice-cold water, followed by extraction with chloroform/methanol. The extract was washed with a saturated aqueous solution of sodium chloride and dried over sodium sulfate. The solvent was evaporated under reduced pressure to give 40 mg (51%) of diacetylated Compound 46.

FAB-MS (m/z); 784 (M+1)$^+$

The same procedure as in Example 1, Step B was repeated using 40 mg (0.051 mmol) of diacetylated Compound 46 to give 20 mg (56%) of Compound 46.

$^1$H-NMR (DMSO-d$_6$) δ; 2.07 (dd, 1H, J=5.1, 14.3 Hz), 2.18 (s, 3H), 2.67 (br, 4H), 3.45 (dd, 1H, J=7.6, 14.3 Hz), 3.59 (br, 4H), 3.94 (s, 3H), 4.10 (s, 2H), 4.22 (d, 2H, J=5.9 Hz), 4.82 (br, 2H), 6.50 (s, 1H), 7.26 (dd, 1H, 5.1, 7.6 Hz), 8.04 (d, 1H, J=9.0 Hz), 8.05 (d, 1H, J=8.7 Hz), 8.13 (dd, 1H, J=1.7, 9.0 Hz), 8.16 (dd, 1H, J=1.7, 8.7 Hz), 8.65 (d, 1H, J=1.7 Hz), 8.81 (s, 1H), 9.93 (d, 1H, J=1.7 Hz).

FAB-MS (m/z); 700 (M+1)$^+$

Example 46
Synthesis of Compound 47

To a solution of 100 mg (0.16 mmol) of Compound 24 in 2 ml of N,N-dimethylformamide were added 100 mg (0.9 mmol) of 4-mercaptopyridine and 44 mg (0.32 mmol) of potassium carbonate, followed by stirring at room temperature for 2 hours. The reaction mixture was poured into ice-cold water, followed by extraction with chloroform/methanol. The extract was washed with a saturated aqueous solution of sodium chloride and dried over sodium sulfate. After the solvent was evaporated under reduced pressure, the residue was purified by silica gel column chromatography (chloroform/methanol=99.8/0.2) to give 67 mg (63%) of diacetylated Compound 47.

FAB-MS (m/z); 854 (M+1)$^+$

The same procedure as in Example 1, Step B was repeated using 67 mg (0.10 mmol) of diacetylated Compound 47 to give 45 mg (58%) of Compound 47.

$^1$H-NMR (DMSO-d$_6$) δ; 2.08 (dd, 1H, J=4.8, 14.3 Hz), 2.19 (s, 3H), 3.47 (dd, 1H, J=7.5, 14.3 Hz), 3.95 (s, 3H), 4.97 (s, 2H), 5.12 (d, 2H, J=4.9 Hz), 5.18 (s, 2H), 6.53 (s, 1H), 7.30 (dd, 1H, J=4.8, 7.5 Hz), 7.37 (br, 4H), 8.07 (d, 1H, J=9.0 Hz), 8.10 (d, 1H, J=8.7 Hz), 8.19 (dd, 1H, J=1.7, 9.0 Hz), 8.29 (dd, 1H, J=1.8, 8.7 Hz), 8.21–8.57 (br, 4H), 8.76 (d, 1H, J=1.7 Hz), 8.86 (s, 1H), 9.99 (d, 1H, J=1.8 Hz).

FAB-MS (m/z); 770 (M+1)$^+$

Example 47
Synthesis of Compound 48

To a solution of 160 mg (0.26 mmol) of Compound 24 in 2 ml of N,N-dimethylformamide were added 290 mg (2.6 mmol) of 2-mercaptopyridine and 83 mg (0.6 mmol) of potassium carbonate, followed by stirring at room temperature for 2 hours. The reaction mixture was poured into ice-cold water, followed by extraction with chloroform/methanol. The extract was washed with a saturated aqueous solution of sodium chloride and dried over sodium sulfate. After the solvent was evaporated under reduced pressure, the residue was purified by silica gel column chromatography (chloroform/methanol=99.8/0.2) to give 123 mg (55%) of diacetylated Compound 48.

FAB-MS (m/z); 854 (M+1)$^+$

The same procedure as in Example 1, Step B was repeated using 20 mg (0.023 mmol) of diacetylated Compound 48 to give 10 mg (53%) of Compound 48.

$^1$H-NMR (DMSO-d$_6$) δ; 2.09 (dd, 1H, J=4.8, 14.2 Hz), 2.19 (s, 3H), 3.47 (dd, 1H, J=7.3, 14.2 Hz), 3.95 (s, 3H), 4.94 (s, 2H), 5.02 (d, 2H, J=3.4 Hz), 5.10 (d, 2H, J=7.7 Hz), 6.52 (s, 1H), 7.01–7.27 (br, 5H), 7.41 (d, 2H, J=8.0 Hz), 7.66 (dt, 2H, J=1.1, 8.0 Hz), 8.06 (d, 1H, J=8.8 Hz), 8.29 (d, 1H, J=8.8 Hz), 8.37 (ddd, 2H, J=0.8, 4.1, 8.0 Hz), 8.72 (s, 1H), 8.81 (s, 1H), 10.02 (s, 1H).

FAB-MS (m/z); 770 (M+1)$^+$

Example 48
Synthesis of Compound 49

To a solution of 140 mg (0.10 mmol) of Compound 24 in 3 ml of N,N-dimethylformamide were added 70 mg (0.60 mmol) of 2-mercaptopyridine and 50 mg (0.36 mmol) of potassium carbonate, followed by stirring at room temperature for 3 hours. The reaction mixture was poured into ice-cold water, followed by extraction with chloroform/methanol. The extract was washed with a saturated aqueous solution of sodium chloride and dried over sodium sulfate. After the solvent was evaporated under reduced pressure, the residue was purified by silica gel column chromatography (chloroform/methanol=95/5) to give 17 mg (16%) of diacetylated Compound 49 and 15 mg (18%) of monoacetylated Compound 49.

Diacetylated Compound FAB-MS (m/z); 856 (M+1)$^+$
Monoacetylated Compound FAB-MS (m/z); 814 (M+1)$^+$ The same procedure as in Example 1, Step B was repeated using 17 mg (0.020 mmol) of diacetylated Compound 49 to give 8.7 mg (56%) of Compound 49.

$^1$H-NMR (DMSO-d$_6$) δ; 2.09 (dd, 1H, J=4.9, 14.0 Hz), 2.19 (s, 3H), 3.30 (br, 1H), 3.95 (s, 3H), 4.96 (s, 2H), 5.03 (s, 2H), 5.15 (d, 2H, J=2.7 Hz), 6.52 (s, 1H), 7.28–7.30 (m, 3H), 8.08 (d, 1H, J=8.8 Hz), 8.09 (d, 1H, J=8.8 Hz), 8.19 (dd, 1H, J=1.7, 8.8 Hz), 8.23 (dd, 1H, J=1.7, 8.8 Hz), 8.59 (d, 2H, J=4.9 Hz), 8.61 (d, 2H, J=4.9 Hz), 8.74 (d, 1H, J=1.7 Hz), 8.80 (br, 1H), 10.0 (d, 1H, J=1.7 Hz).

FAB-MS (m/z); 772 (M+1)$^+$

Example 49
Synthesis of Compound 50

To a solution of 105 mg (0.15 mmol) of Compound 24 in 1.8 ml of N,N-dimethylformamide/methanol (5/1) were added 38 mg (0.30 mmol) of 4-hydroxymercaptobenzene and 50 mg (0.36 mmol) of potassium carbonate, followed by stirring at room temperature for 12 hours. The reaction mixture was poured into ice-cold water, followed by extraction with chloroform/methanol. The extract was washed with a saturated aqueous solution of sodium chloride and dried over sodium sulfate. After the solvent was evaporated under reduced pressure, the residue was purified by silica gel column chromatography (chloroform/methanol=9/1) to give 76 mg (63%) of Compound 50.

$^1$H-NMR (DMSO-d$_6$) δ; 2.08 (s,3H), 2.09 (dd, 1H, J=2.7, 7.6 Hz), 3.45 (dd, 1H, J=7.6, 14.2 Hz), 3.94 (s, 3H), 4.44 (br, 2H), 4.56 (d, 2H, J=5.1 Hz), 5.11 (d, 2H, J=4.4 Hz)6.50 (s, 1H), 6.73 (td, 4H, J=2.2, 8.9 Hz), 7.27 (m, 3H), 8.02 (d, 1H, J=8.9 Hz), 8.04 (d, 1H, J=1.7, 8.9 Hz), 8.09 (dd, 1H, J=1.7, 8.9 Hz), 8.14 (dd, 1H, J=1.9, 8.9 Hz), 8.61 (d, 1H, J=1.7 Hz), 8.77 (s,1H), 9.58 (s, 2H), 9.92 (d, 1H, J=1.4 Hz).

FAB-MS (m/z); 800 (M+1)$^+$

Example 50
Synthesis of Compound 51

To a solution of 70 mg (0.10 mmol) of Compound 24 in 2 ml of N,N-dimethylformamide were added 25 mg (0.21 mmol) of 2-mercaptothiazoline and 28 mg (0.20 mmol) of potassium carbonate, followed by stirring at room temperature for 1 hour. To the mixture was added a solution of sodium methoxide in methanol, followed by stirring for 30 minutes. The reaction mixture was poured into ice-cold water, followed by e ion with chloroform/methanol. The extract was washed with a saturated aqueous solution of sodium chloride and dried over sodium sulfate. After the solvent was evaporated under reduced pressure, the residue was purified by silica gel column chromatography (chloroform/methanol=9/1) to give 30 mg (38%) of Compound 51.

$^1$H-NMR (DMSO-d$_6$) δ; 2.07 (br, 1H), 2.18 (s, 3H), 3.48 (br, 5H), 3.95 (s, 3H), 4.11 (t, 2H, J=8.0 Hz), 4.15 (t, 2H, J=8.0 Hz), 4.96 (s, 2H), 5.02 (s, 2H), 5.16 (d, 2H, J=2.7 Hz), 6.51 (s, 1H), 7.27 (dd, 1H, J=4.9, 7.2 Hz), 8.06 (d, 2H, J=8.8 Hz), 8.13 (dd, 1H, J=1.7, 8.8. Hz),8.17 (dd, 1H, J=1.7, 8.8 Hz), 8.68 (d, 1H, J=1.7 Hz), 8.82 (s, 1H), 9.96 (d, 1H, J=1.7 Hz).

FAB-MS (m/z); 786 (M+1)$^+$

Example 51
Synthesis of Compound 52

To a solution of 160 mg (0.26 mmol) of Compound 24 in 2 ml of N,N-dimethylformamide were added 290 mg (2.6 mmol) of 5-mercapto-1-methyltetrazole and 83 mg (0.6 mmol) of potassium carbonate, followed by stirring at room temperature for 2 hours. The reaction mixture was poured into ice-cold water, and precipitates were removed by filtration. The filtrate was purified by silica gel column chromatography (chloroform/methanol=9/1) to give 50 mg (23%) of diacetylated Compound 52.

FAB-MS (m/z); 864 (M+1)$^+$

The same procedure as in Example 1, Step B was repeated using 50 mg (0.058 mmol) of diacetylated Compound 52 to give 20 mg (44%) of Compound 52.

$^1$H-NMR (DMSO-d$_6$) δ; 2.10 (dd, 1H, J=4.8, 14.2 Hz), 2.19 (s, 3H), 3.47 (dd, 1H, J=7.5, 14.2 Hz), 3.95 (s, 3H), 4.05 (s, 6H), 5.20 (s, 2H), 5.24 (s, 2H), 5.33 (s, 2H), 6.54 (s, 1H), 7.30 (dd, 1H, J=4.8, 7.5 Hz), 8.08 (d, 1H, J=9.0 Hz), 8.10 (d, 1H, J=9.0 Hz), 8.16 (d, 1H, J=9.0 Hz), 8.21 (d, 1H, J=9.0 Hz), 8.72 (s, 1H), 8.84 (s, 1H), 9.98 (s, 1H).

FAB-MS (m/z); 780 (M+1)$^+$

Example 52
Synthesis of Compound 53

To a solution of 211 mg (0.30 mmol) of Compound 27 in 5 ml of chloroform/methanol (1/1) was added 56 mg (0.80 mmol) of sodium methanethiolate, followed by stirring at room temperature for 3 hours. The reaction mixture was poured into ice-cold water, followed by extraction with chloroform/methanol. The extract was washed with a saturated aqueous solution of sodium chloride and dried over sodium sulfate. The solvent was evaporated under reduced pressure to give 52 mg (26%) of Compound 53.

$^1$H-NMR (DMSO-d$_6$) δ; 2.07 (dd, 1H, J=4.9, 14.1 Hz), 2.16 (s, 3H), 2.17 (s, 3H), 2.18 (s, 3H), 2.87 (dd, 1H, J=7.4, 14.1 Hz), 2.88 (t, 2H, J=7.1 Hz), 2.89 (t, 2H, J=7.1 Hz), 3.44 (t, 2H, J=7.1 Hz), 3.53 (t, 2H, J=7.1 Hz), 3.94 (s, 3H), 5.16 (d, 2H, J=3.9 Hz), 6.49 (s, 1H), 7.25 (dd, 1H, J=4.9, 7.4 Hz), 8.03 (d, 1H, J=9.0 Hz), 8.04 (d, 1H, J=8.8 Hz), 8.12 (dd, 1H, J=1.7, 9.0 Hz), 8.14 (dd, 1H, J=1.7, 8.8 Hz), 8.61 (d, 1H, J=1.7 Hz), 8.77 (br, 1H), 9.96 (d, 1H, J=1.5 Hz).

FAB-MS (m/z); 672 (M+1)$^+$

Example 53
Synthesis of Compound 54

To a solution of 110 mg (0.2 mmol) of Compound c in 5 ml of methylene chloride was added 0.16 ml (2 mmol) of acryloyl chloride, followed by stirring at room temperature for 5 minutes. To the mixture was gradually added 0.40 g (3 mmol) of aluminum chloride, followed by stirring for 2.5 hours. The reaction mixture was poured into ice-cold water, followed by extraction with chloroform/methanol. The extract was washed with a saturated aqueous solution of sodium chloride and dried over sodium sulfate. The solvent was evaporated under reduced pressure to give diacetylated Compound 54. The same procedure as in Example 1, Step B was repeated using the diacetylated Compound 54 to give 32 mg (25%) of Compound 54.

$^1$H-NMR (DMSO-d$_6$) δ; 2.07 (dd, 1H, J=4.9, 14.4 Hz), 2.17 (s, 3H), 2.50 (s, 6H), 3.37 (t, 2H, J=6.2 Hz), 3.45 (br, 1H), 3.46 (t, 2H, J=6.2 Hz), 3.80 (dt, 4H, J=1.2, 6.2 Hz), 3.94 (s, 3H), 5.16 (d, 2H, J=3.9 Hz), 6.49 (s, 1H), 7.25 (dd, 1H, J=4.9, 7.2 Hz), 8.03 (dd, 2H, J=1.9, 9.0 Hz), 8.11 (dd, 1H, J=1.5, 9.0 Hz), 8.13 (dd, 1H, J=1.5, 9.0 Hz), 8.62 (d, 1H, J=1.6 Hz), 8.77 (br, 1H), 9.96 (d, 1H, J=1.7 Hz).

FAB-MS (m/z); 640 (M+1)$^+$

Example 54
Synthesis of Compound 55

To a solution of 126 mg (0.2 mmol) of Compound A in 5 ml of methylene chloride was added 0.21 ml (2.0 mmol) of n-butyl chloride, followed by stirring at room temperature for 5 minutes. To the mixture was gradually added 0.40 g (3 mmol) of aluminum chloride, followed by stirring for 2.5 hours. The reaction mixture was poured into ice-cold water, followed by extraction with chloroform/methanol. The extract was washed with a saturated aqueous solution of sodium chloride and dried over sodium sulfate. The solvent was evaporated under reduced pressure to give diacetylated Compound 55. The same procedure as in Example 1, Step B was repeated using the diacetylated compound to give 21 mg (25%) of Compound 55.

$^1$H-NMR (DMSO-$d_6$) δ; 1.01 (t, 2H, J=7.3 Hz), 1.74 (tq, 2H, J=7.1, 7.3 Hz), 2.01 (dd, 1H, J=4.9, 14.2 Hz), 2.17 (s, 3H), 2.19 (t, 2H, J=7.1 Hz), 3.41 (dd, 1H, J=7.3, 14.2 Hz), 3.93 (s, 3H), 5.13 (d, 2H, J=3.9 Hz), 6.45 (s, 1H), 7.19 (dd, 1H, J=4.9, 7.3 Hz), 7.64 (dd, 1H, J=2.0, 8.8 Hz), 7.95 (d, 1H, J=8.8 Hz), 8.02 (d, 1H, J=9.0 Hz), 8.12 (dd, 1H, J=1.7, 9.0 Hz), 8.59 (d, 1H, J=1.5 Hz), 8.78 (s, 1H), 9.41 (d, 1H, J=1.7Hz).

FAB-MS (m/z); 616, 618 (M+1)$^+$

Example 55
Synthesis of Compound 56

To a solution of 82 mg (0.15 mmol) of Compound c in 2 ml of methylene chloride was added 0.18 ml (1.5 mmol) of valeroyl chloride, followed by stirring at room temperature for 5 minutes. To the mixture was gradually added 0.27 g (2.0 mmol) of aluminum chloride, followed by stirring for 3 hours. The reaction mixture was poured into ice-cold water, followed by extraction with chloroform/methanol. The extract was washed with a saturated aqueous solution of sodium chloride and dried over sodium sulfite. After the solvent was evaporated under reduced pressure, the residue was purified by silica gel column chromatography (chloroform/methanol=99/1) to give 59 mg (45%) of Compound 56.

$^1$H-NMR (CDCl$_3$) δ; 1.01 (t, 3H, J=7.6 Hz), 1.02 (t, 3H, J=7.6 Hz), 1.51 (br, 4H), 1.80 (s, 3H), 1.82 (br, 4H), 2.17 (dd, 1H, J=5.1, 14.7 Hz), 2.31 (s, 3H), 2.77 (s, 3H), 3.15 (br, 4H), 4.02 (dd, 1H, J=7.4, 14.7 Hz), 4.03 (s, 3H), 5.38 (d, 2H, J=2.32 Hz), 6.99 (dd, 1H, J=5.1, 7.4 Hz), 7.52 (d, 1H, J=8.7 Hz), 7.96 (d, 1H, J=8.8 Hz), 8.18 (dd, 1H, J=1.7, 8.7 Hz), 8.19 (dd, 1H, J=1.8, 8.8 Hz), 8.57 (d, 1H, J=1.5 Hz), 9.82 (d, 1H, J=1.6 Hz).

FAB-MS (m/z); 720 (M+1)$^+$

Example 56
Synthesis of Compound 57

To a solution of 127 mg (0.2 mmol) of Compound g in 3.0 ml of chloroform were added 48 mg (0.1 mmol) of tetrabutylammonium bromide and 1 ml of methanol, followed by reflux for 5 hours. The reaction mixture was poured into ice-cold water, followed by extraction with chloroform/methanol (9/1). The extra was washed with a saturated aqueous solution of sodium chloride and dried over sodium sulfite. After the solvent was evaporated under reduced pressure, the residue was purified by silica gel column chromatography (chloroform/methanol=99/1) to give 21 mg (13%) of Compound 57.

$^1$H-NMR (CDCl$_3$) 67 ; 1.82 (s, 3H), 2.18 (dd, 1H, J=5.1, 14.5 Hz), 2.33 (s, 3H), 2.77 (s, 3H), 4.04 (s, 3H), 4.05 (dd, 1H, J=7.3, 14.5 Hz), 4.62 (d, 2H, J=4.9 Hz), 4.76(d, 2H, J=1.0 Hz), 5.41 (d, 2H, J=1.5 Hz), 7.02 (dd, 1H, J=5.1, 7.3 Hz), 7.5 (d, 1H, J=8.8 Hz), 8.01 (d, 1H, J=8.8 Hz), 8.23 (dd, 1H, J=1.7, 8.8 Hz), 8.25 (dd, 1H, J=1.7, 8.8 Hz), 8.64 (d, 1H, J=1.7 Hz), 9.88 (d, 1H, J=1.7 Hz).

FAB-MS (m/z);794, 796, 798(M+1)$^+$

Example 57
Synthesis of Compound 58

To a solution of 105 mg (0.18 mmol) of Compound d in 3 ml of methanol/chloroform (1/1) was added 6.8 mg (0.18 mmol) of sodium borohydride, followed by stirring under ice cooling for 30 minutes. The reaction mixture was then poured into ice-cold water, followed by extraction with chloroform/methanol (9/1). The extract was washed with a saturated aqueous solution of sodium chloride and dried over sodium sulfite. After the solvent was evaporated under reduced pressure, the residue was purified by silica gel column chromatography (chloroform/methanol=99/1) to give 85 mg (81%) of Compound 58.

FAB-MS (m/z); 596 (M+1)$^+$

Example 58
Synthesis of Compound 59

The same procedure as in Example 1, Step B was red using the product obtained by repeating the same procedure as in Example 57 using 73 mg (0.1 mmol) of Compound 27 to give 37 mg (65%) of Compound 59.

$^1$H-NMR (DMSO-$d_6$) δ; 1.98 (br, 1H), 2.10 (br, 2H), 2.14 (s, 3H), 2.22 (br, 2H), 3.37 (dd, 1H, J=7.3, 13.9 Hz), 3.65 (br, 2H), 3.80 (br, 2H), 3.93 (s, 3H), 4.85 (br, 2H), 5.10 (br, 2H), 5.43 (br, 1H), 5.48 (br, 1H), 6.31 (s, 1H), 7.12 (dd, 1H, J=6.8, 7.3 Hz), 7.48 (br, 2H), 7.85 (br, 2H), 7.96 (d, 0.5 H, J=1.5 Hz), 7.97 (d, 0.5 H, J=1.5Hz), 8.59 (s, 1H), 9.16 (d, 0.5 H, J=1.5Hz), 9.19 (d, 0.5 H, J=1.5 Hz).

FAB-MS (m/z); 652 (M+1)$^+$

Example 59
Synthesis of Compound 60

The same procedure as in Example 57 was repeated using 100 mg (0.12 mmol) of Compound 40 to give 47 mg (51%) of Compound 60.

FAB-MS (m/z); 640 (M+1)$^+$

Example 60
Synthesis of Compound 61

The same procedure as in Example 20 was repeated using 68 mg (0.10 mmol) of Compound H to give 8.7 mg (16%) of Compound 61.

$^1$H-NMR (DMSO-$d_6$) δ; 2.18 (s, 3H), 2.46 (s, 6H), 2.83 (dd, 1H, J=4.9, 14.4 Hz), 3.52 (dd, 1H, J=7.3, 14.4 Hz), 3.56 (s, 2H), 4.08 (s, 3H), 4.71 (d, 1H, J=15.9 Hz), 4.80 (d, 1H, J=15.9 Hz), 4.90 (br, 1H), 5.46 (br, 1H), 6.80 (dd, 1H, J=4.9, 7.3 Hz), 7.24 (d, 1H, J=8.3 Hz), 7.41 (br, 2H), 7.53 (dt, 1H, J=1.1, 7.1 Hz), 7.93 (br, 2H), 9.06 (s, 1H).

FAB-MS (m/z); 549 (M+1)$^+$

Example 61
Synthesis of Compound 62

In a 30-ml two-necked flask were placed 12.6 mg (0.018 mmol) of bistriphenylphosphine palladium (II) chloride and 4.2 mg (0.022 mmol) of CuI, and the atmosphere was replaced with argon. To the mixture was added a solution of 40 mg (0.059 mmol) of Compound I in 3 ml of methylene choloride/diethylamine (2/1), followed by stirring at room temperature for 20 minutes. To the mixture was added 0.16 ml (1.5 mmol) of N-methyl-N-propargylbenzylamine, followed by stirring at room temperature for 3 hours. After insoluble materials were removed by filtration, the filtrate was evaporated under reduced pressure. The residue was purified by silica gel column chromatography (methanol/chloroform=1/25) to give 12.3 mg (Z-form, 30%) of Compound 62.

$^1$H-NMR (DMSO-$d_6$) δ; 2.02 (dd, 1H, J=4.9, 13.7 H), 2.14 (s, 3H), 2.34 (s, 3H), 3.28 (d, 2H, J=9.5 Hz), 3.40 (dd, 1H, J=7.3, 13.7 Hz), 3.57 (s, 2H), 3.66 (s, 2H), 3.93 (s, 3H), 5.05 (d, 1H, J=18.2 Hz), 5.10 (d, 1H, J=18.2 Hz), 6.42 (s,1H), 7.17 (dd, 1H, J=4.9, 7.3), 7.29 (br, 1H), 7.37 (br, 4H), 7.58 (d, 1H, J=1.5, 8.8 Hz), 7.63 (d, 1H, J=2.2, 8.8 Hz), 7.94

(d, 2H, J=8.8 Hz), 8.11 (d, 1H, J=1.5 Hz), 8.74 (s, 1H), 9.40 (d, 1H, J=2.2 Hz).

FAB-MS (m/z); 704, 706 (M+1)$^+$

Example 62

Synthesis of Compound 63

To a solution of 71.4 mg (0.1 mmol) of diacetylated Compound 20 in 3 ml of methanol was added 25 mg of 10% Pd/C, followed by reflux in a hydrogen atmosphere for 1 hour. Insoluble materials were removed by filtration, and the filtrate was evaporated under reduced pressure. The residue was purified by silica gel column chromatography (chloroform) to give 23.0 mg (Z-form, 33%) of Compound 63.

FAB-MS (m/z); 718 (M+1)$^+$

Example 63

Synthesis of Compound 64

The same procedure as in Example 1, Step B was repeated using 23 mg (0.033 mmol) of Compound 63 to give 8.7 mg (41%) of Compound 64.

$^1$H-NMR (CD$_3$OD) δ; 2.11 (dd, 1H, J=5.0, 14.1 Hz), 2.21 (s, 3H), 2.34 (s, 6H), 2.44 (s, 6H), 3.43 (dd, 1H, J=7.7, 14.4 Hz), 3.55 (dd, 2H, J=1.5, 6.5 Hz), 3.67 (dd, 2H, J=1.5, 6.5 Hz), 4.02 (s, 3H), 5.03 (d, 2H, J=5.8 Hz), 5.74 (dt,1H, J=6.5, 11.7 Hz), 5.80 (s, 1H), 6.87 (d, 1H, J=11.7 Hz), 6.88 (d, 1H, J=11.7 Hz), 7.05(dd, 1H, J=5.0, 7.7 Hz), 7.20–7.58 (m, 2H),7.68 (d, 1H, J=8.4 Hz), 7.86 (s, 1H), 7.95 (d,1H, J=8.8 Hz), 9.16 (s, 1H).

FAB-MS (m/z); 634 (M+1)$^+$

Example 64

Synthesis of Compound 65

To a solution of 1.16 g (0.64 mmol) of Compound e in 100 ml of acetonitrile was added 823 mg (2.4 mmol) of triphenylphosphine hydrobromide, followed by stirring at 80_C. for 1 hour. To the mixture was added ethyl acetate, and the precipitated phosphonium salt was collected by filtration, and dried under reduced pressure to give 1.22 g (67%) of crude phosphonium salt. To a solution of 91 mg (0.1 mmol) of the phosphonium salt in 3 ml of methylene chloride were added 16.5 mg (1.3 mmol) of potassium carbonate and 3.0 mg (0.011 mmol) of 18-crown-6, followed by stirring at room temperature for 30 minutes. To the mixture was added 2.3 ml (5.0 mmol) of propionaldehyde, followed by stirring at room temperature for 4 days. The reaction mixture was the poured into a saturated aqueous solution of ammonium chloride, followed by extraction with chloroform. The extract was washed with a saturated aqueous solution of sodium chloride, and dried over sodium sulfate. After the solvent was evaporated under reduced pressure, the residue was purified by silica gel column chromatography (chloroform/methanol=200/1) to give 22.6 mg (E/Z=1/1, 37%) of Compound 65.

FAB-MS (m/s); 606 (M+1)$^+$

Example 65

Synthesis of Compound 66

The same procedure as in Example 1, Step B was repeated using 22.6 mg (0.037 mmol) of Compound 65 to give 13.1 mg (EZ=1/1, 68%) of Compound 66.

FAB-MS (m/s); 522 (M+1)$^+$

Example 66

Synthesis of Compound 67

The same procedure as in Example 64 was repeated using 450 mg (0.64 mmol) of Compound K to give 367 mg (E/Z=1/1, 78%) of Compound 67.

FAB-MS (m/s); 732 (m+1)$^+$

Example 67

Synthesis of Compound 68

To a solution of 120 mg (0.02 mmol) of Compound f in 100 ml of acetonitrile was added 823 mg (2.4 mmol) of triphenylphosphine hydrobromide, followed by stirring at 80_C. for 1 hour. To the mixture was then added ethyl acetate, and the precipitated phosphonium salt was collected by filtration, and dried under reduced pressure to give crude phosphonium salt. To a solution of the phosphonium salt in 3 ml of methylene chloride were added 26 mg (0.2 mmol) of potassium-t-butoxide and 6.0 mg (0.022 mmol) of 18-crown-6, followed by stirring at room temperature for 30 minutes. To the mixture was added 0.12 ml (0.25 mmol) of propionaldehyde, followed by stirring at room temperature for 4 days. The reaction mixture was the poured into a saturated aqueous solution of ammonium chloride, followed by extraction with chloroform. The extract was washed with a sated aqueous solution of sodium chloride, and dried over sodium sulfate. The solvent was evaporated under reduced pressure to give diacetylated Compound 68. The same procedure as in Example 1, Step B was repeated using the diacetylated compound to give 17.0 mg (mixture of E and Z, 13%) of Compound 68.

FAB-MS (m/s); 576 (M+1)$^+$

Example 68

Synthesis of Compound 69

To a solution of 211 mg (0.3 mmol) of Compound 24 in 2 ml of trifluoroacetic acid was added 0.19 ml (1.5 mmol) of triethylsilane, followed by stirring under ice cooling for 2 hours. The reaction mixture was the poured into ice-cold water, and the resulting precipitates were collected by filtration, and washed with hexane. The product was then purified by silica gel column chromatography (chloroform) to give 150 mg (73%) of diacetylated Compound 69. The same procedure as in Example 1, Step B was repeated using 68 mg (0.1 mmol) of diacetylated Compound 69 to give 48 mg (81%) of Compound 69.

$^1$H-NMR (DMSO-d$_6$) δ; 1.98 (dd, 1H, J=3.8, 5.5 Hz), 2.13 (s, 3H), 3.24 (m, 5H), 3.92 (s, 3H), 3.93 (t, 2H, J=7.2 Hz), 3.97 (t, 2H, 7.5 Hz), 5.01 (br, 2H), 6.30 (s, 1H), 7.11 (dd, 1H, J=3.8, 7.2 Hz), 7.40 (dd, 1H, J=1.5, 8.3 Hz), 7.42 (dd, 1H, J=1.5, 8.3 Hz), 7.84 (d, 1H, J=8.3 Hz), 7.86 (d, 1H, 8.3 Hz), 7.97 (d, 1H, J=1.2 Hz), 8.63 (br, 1H), 9.08 (d, 1H, J=1.2 Hz).

FAB-MS (m/s); 592, 594, 596(M+1)$^+$

Example 69

Synthesis of Compounds 70a, 70b and 70c

To a solution of 679 mg (1.2 mmol) of Compound 69 in 10 ml of N,N-dimethylformamide was added 380 mg (23 mmol) of potassium iodide, followed by stirring at 90_C. for 3 hours. The reaction mixture was poured into ice-cold water, followed by extraction with chloroform/methanol (9/1). The extract was washed with a saturated aqueous solution of sodium chloride and then dried over sodium sulfate. After evaporation under reduced pressure, the residue was purified by silica gel column chromatography (chloroform) to give 300 mg (67%) of Compound 70a, 89 mg (15%) of Compound 70b, and 42 mg (5%) of Compound 70c.

Compound 70a $^1$H-NMR (CDCl$_3$) δ; 2.20 (s, 3H), 2.47 (dd, 1H, J=4.8, 8.3 Hz), 3.40 (br, 9H), 4.10 (s, 3H), 4.26 (br,1H), 4.86 (d, 1H, J=16.7 Hz), 4.93 (d, 1H, J=16.7 Hz), 5.91 (br, 1H), 6.85 (dd, 1H, J=4.8,7.5 Hz), 7.28 (br, 2H), 7.37 (d, 1H, J=8.3 Hz),7.72 (br, 1H), 7.78 (d, 1H, J=8.6 Hz), 8.97(br, 1H).

FAB-MS (m/s); 776 (M+1)+

Compound 70b $^1$H-NMR (DMSO-d$_6$) δ; 2.20 (s, 3H), 2.43 (dd, 1H, J=4.8, 14.3 Hz), 3.17 (t, 2H, J=7.1 Hz), 3.21 (t,2H, J=7.1 Hz), 3.32 (dd, 1H, J=7.4, 14.3 Hz),4.00 (s, 3H), 4.23 (br, 1H, 4.50 (br, 4H), 4.84(d, 1H, J=15.9 Hz), 4.93 (d, 1H, J=15.9 Hz),6.00 (br, 1H), 6.87 (dd, 1H, J=4.8, 7.4 Hz),7.32 (dd, 1H, J=1.7, 8.3 Hz), 7.34 (dd, 1H, J=1.7, 8.4 Hz), 7.39 (d, 1H, J=8.3 Hz), 7.72 (s,1H), 7.76 (d, 1H, J=8.4 Hz), 8.08 (s, 1H), 8.09(s, 1H), 9.04 (br, 1H).

FAB-MS (m/s); 612 (M+1)+

Compound 70c $^1$H-NMR (CDCl$_3$) δ; 1.95 (dd, 1H, J=4.8, 14.0 Hz), 2.13 (s, 3H), 2.92 (t, 2H, J=7.1 Hz), 3.16 (t, 2H, J=7.1 Hz), 3.34 (dd, 1H, J=7.4, 14.0 Hz), 3.70 (m, 4H), 3.92 (s, 3H), 4.67 (t, 2H, J=5.3 Hz), 4.99 (d, 1H, J=5.8 Hz), 6.28 (br, 1H), 7.08 (dd, 1H, J=4.8, 7.4 Hz), 7.32 (dd, 1H, J=1.7, 8.4 Hz), 7.34 (dd, 1H, J=1.7, 8.4 Hz), 7.78 (d, 1H, J=8.4 Hz), 7.82 (d, 1H, J=8.4 Hz), 8.59 (s, 1H), 9.03 (br, 1H).

FAB-MS (m/s); 556 (M+1)+

Example 70

Synthesis of Compound 71

To a solution of 55 mg (0.1 mmol) of Compound 70c in 5 ml of methylene chloride were added 0.5 ml of triethylamine and 71 mg (0.4 mmol) of isonicotinoyl chloride hydrochloride, followed by stirring at room temperature for 3 hours. The reaction mixture was poured into ice-cooled 1 N hydrochloric acid, followed by extraction with chloroform/methanol. The extract was washed with a saturated aqueous solution of sodium chloride and dried over sodium sulfate. After the solvent was evaporated under reduced pressure, the residue was purified by silica gel column chromatography (chloroform/methanol=20/1) to give 32 mg (42%) of Compound 71.

$^1$H-NMR (CDCl$_3$) δ; 1.97 (dd, 1H, J=4.9, 13.9 Hz), 2.12 (s, 3H), 3.30 (br, 5 H), 3.91 (s, 3H), 4.58 (dt, 2H, J=2.2, 6.7 Hz), 4.65 (t, 2H, J=6.7 Hz), 4.97 (br, 2H), 6.29 (s, 1H), 7.09 (dd, 1H, J=4.9, 7.1 Hz), 7.45 (d, 2H, J=8.6 Hz), 7.85 (br, 5H), 8.66 (s, 1H), 8.77 (d, 4H, J=6.1 Hz),8.81 (d, 4H, J=6.1 Hz), 9.01 (d, 1H, J=1.5 Hz).

FAB-MS (m/s); 766 (M+1)+

Example 71

Synthesis of Compounds 72a and 72b

The same procedure as in Example 23 was repeated using 110 mg (0.2 mmol) of Compound c and 0.32 ml (2.0 mmol) of methyloxalyl chloride give a product. The same procedure as in Example 68 was repeated using the obtained product to give 12.2 mg (11%) of Compound 72a and 37.2 mg (31%) of Compound 72b.

Compound 72a $^1$H-NMR (CDCl$_3$) δ; 2.16 (s, 3H), 2.72 (dd, 1H, J=4.8, 14.4 Hz), 3.43 (dd, 1H, J=7.6, 14.4 Hz), 3.77 (s, 3H), 3.78 (s, 2H), 4.09 (s, 3H), 4.64 (d, 1H, J=16.3 Hz), 4.75 (d, 1H, J=16.3 Hz), 4.85 (br, 1H), 5.54 (br, 1H), 6.80 (dd, 1H, J=4.8, 7.6 Hz), 7.36 (d, 1H, J=7.3 Hz), 7.39 (dt, 1H, J=0.8, 7.3 Hz), 7.50 (s, 2H), 7.88 (d, 1H, J=7.3 Hz), 7.91 (d, 1H, J=8.3 Hz), 8.82 (br, 1H).

FAB-MS (m/s); 540 (M+1)+

Compound 72b $^1$H-NMR (CDCl$_3$) δ; 2.00 (dd, 1H, J=4.7, 14.0 Hz), 2.15 (s, 3H), 3.30 (s, 1H), 3.65 (s, 6H), 3.84 (s, 2H), 3.90 (s, 2H), 3.93 (s, 3H), 5.00 (d, 2H, J=5.4 Hz), 6.33 (s, 1), 7.12 (dd, 1H, J=4.7,7.1 Hz), 7.36 (d, 1H, J=7.3 Hz), 7.85 (d, 1H, J=7.3 Hz), 7.94 (d, 1H, J=7.3 Hz), 7.95 (s,1H), 8.05 (d, 1H, J=7.3 Hz), 8.62 (br, 1H), 9.08 (s, 1H).

FAB-MS (m/s);612(M+1)+

Example 72

Synthesis of Compounds 73a, 73b and 73c

The same procedure as in Examples 68 and 69 was repeated using 141 mg (0.2 mmol) of Compound 27 to give 56 mg (67%) of Compound 73a, 3.0 mg (2.4%) of Compound 73b and 27 mg (23%) of Compound 73c.

Compound 73a

FAB-MS (m/s); 804(M+1)+

Compound 73b hu 1H-NMR (CDCl$_3$)δ; 2.10–2.18 (m, 4H), 2.21 (s, 3H), 2.29 (dd, 1H, J=4.9, 14.3 Hz), 2.92 (t, 2H, J=7.4 Hz), 2.94 (t, 2H, J=7.4 Hz), 3.27 (dd, 1H,J=7.5, 14.3 Hz), 4.24 (s, 3H), 4.26 (t, 2H, J=7.4 Hz), 4.28 (t, 2H, J=7.4 Hz), 5.02 (d, 2H,=6.4 Hz), 6.09 (br, 1H), 6.88 (dd, 1H, J=2.7, 4.7 Hz), 7.30 (d, 1H, J=8.0 Hz), 7.37 (d, 1H, J=8.3 Hz), 7.42 (d, 1H, J=8.0 Hz), 7.71 (d, 1H,J=1.7 Hz), 7.72 (d, J=8.3 Hz), 8.12 (s, 1H), 8.14 (s, 1H), 9.14 (d, 1H, J=1.2 Hz).

FAB-MS (m/s); 640 (M+1)+

Compound 73c $^1$H-NMR (CDCl$_3$)δ; 1.85 (s, 4H), 1.97 (dd, 1,H, J=4.9, 14.1 Hz), 2.17 (s, 3H), 2.81 (dt, 4H, J=10.0, 16.0 Hz), 3.33 (dd, 1H, J=7.1, 14.1 Hz), 3.50 (t, 4H, J=6.4 Hz), 3.92 (s, 3H), 4.49 (br, 2H),4.99 (d, 1H, J=5.4 Hz), 6.27 (S, 1H), 7.07 (dd, 1H, J=4.9, 7.3 Hz), 7.32 (d, 2H, J=8.4 Hz),7.78 (d, 1H, J=8.4 Hz), 7.82 (s, 1H), 7.83 (d, 1H, J=8.4 Hz), 9.03 (d, 1H, J=1.2 Hz).

FAB-MS (m/s); 584 (M+1)+

Example 73

Synthesis of Compound 74

To a solution of 31 mg (0.05 mmol) of Compound 22 in 3 ml of N,N-dimethylformamide was added 15 mg of 10% Pd/C, followed by stirring in a hydrogen atmosphere at 60_C. for 5 hours. After insoluble materials were removed by filtration, the filtrate was evaporated under reduced pressure. The residue was purified by silica gel column chromatography (chloroform) to give 12 mg (20%) of Compound 74.

$^1$H-NMR (CDCl$_3$)δ; 2.05 (br, 4H), 2.20 (s, 3H), 2.44 (dd, 1H, J=4.9, 14.4 Hz), 2.88 (t, 2H, J=7.4 Hz), 2.92 (t, 2H, J=7.4 Hz), 3.32 (dd, 1H, J=7.4, 14.4 Hz), 3.47 (t, 2H, J=7.4 Hz), 3.48 (t, 2H, J=7.4 Hz), 3.78 (s, 6H), 4.00 (s, 3H), 4.12(br, 1H), 4.85 (d, 1H, J=15.8 Hz), 4.92 (d, 1H, J=15.8 Hz), 5.93 (br, 1H), 6.85 (dd, 1H, J=4.9, 7.4 Hz), 7.30 (br, 2H), 7.34 (d, 1H, J=8.0 Hz), 7.70 (d, 1H, J=1.3 Hz), 7.74 (d, 1H, J=7.3 Hz), 8.98 (d, 1H, J=1.0 Hz).

FAB-MS (m/s); 612 (M+1)+

Example 74

Synthesis of Compound 75

To a solution of 50 mg (0.06 mmol) of Compound 70a in 3 ml of N,N-dimethylformamide was added 0.5 ml of piperidine, followed by stirring at room temperature overnight. Water was added to the reaction mixture, followed by extraction with chloroform/methanol (9/1). The extract was washed with a saturated aqueous solution of sodium chloride, and dried over sodium sulfate. After the solvent was evaporated under reduced pressure, the residue was purified by silica gel columnn chromatography (chloroform/methanol=10/1) to give 10 mg (15%) of Compound 75.

$^1$H-NMR (CDCl$_3$)δ; 1.55 (br, 10H)§ 2.19 (s, 3H), 2.31 (dd, 1H, J=4.9, 7.6 Hz), 2.53 (br, 8H), 2.66 (br, 2H), 2.74 (br, 2H), 3.02 (br, 2H), 3.26 (dd, 1H, J=6.8, 7.5 Hz), 4.09 (s, 3H), 4.93 (d, 2H, J=10.2 Hz), 6.09 (br, 1H), 6.86 (dd, 1H, J=4.9, 7.3 Hz), 7.35 (br, 3H), 7.71 (d, 1H, J=8.6 Hz), 7.74 (d, 1H, J=1.5 Hz), 9.08 (br, 1H).

FAB-MS (m/s); 690 (M+1)+

Example 75
Synthesis of Compound 76

The same procedure as in Example 74 was repeated using 50 mg (0.06 mmol) of Compound 70a and 0.5 ml of morpholine to give 24 mg (59%) of Compound 76.

$^1$H-NMR (CDCl$_3$)δ; 2.20 (s, 3H), 2.29 (dd, 1H, J=4.9, 14.4 Hz), 2.69 (br, 8H), 2.71 (br, 4H), 3.01 (br, 4H), 3.26 (dd, 1H, J=7.4, 14.4 Hz), 3.78 (br, 8H), 3.89 (br, 1H), 4.09 (s, 3H), 4.98 (d, 2H, J=4.9 Hz), 6.11 (s, 1H), 6.87 (dd, 1H, J=4.9, 7.4 Hz), 7.34 (br, 2H), 7.70 (d, 1H, J=8.5 Hz), 7.71 (d, 1H, J=8.5 Hz), 7.74 (d, 1H, J=1.2 Hz), 9.12 (s, 1H).

FAB-MS (m/s); 694 (M+1)$^+$

Example 76
Synthesis of Compound 77

The same procedure as in Example 74 was repeated using 50 mg (0.06 mmol) of Compound 70a and 0.5 ml of diethylamine to give 7.3 mg (18%) of Compound 77.

hu 1H-NMR (CDCl$_3$)δ; 1.12 (t, 6H, J=7.2 Hz), 1.14 (t, 6H, J=7.2 Hz), 2.19 (s, 3H), 2.37 (dd, 1H, J=4.9, 14.4 Hz), 2.68 (q, 4H, J=7.2 Hz), 2.72 (q, 4H, J=7.2 Hz), 2.83 (br, 4H), 2.95 (br, 4H), 3.29 (dd, 1H, J=7.4, 14.4 Hz), 4.09 (s, 3H), 4.88 (d, 1H, J=16.4 Hz), 4.96 (d, 1H, J=16.4 Hz), 6.05 (br, 1H), 6.86 (dd, 1H, J=4.9, 7.4 Hz), 7.29 (br, 2H), 7.36 (d, 1H, J=8.3 Hz), 7.70 (s, 1H,), 7.73 (d, 1H, J=8.3 Hz), 9.03 (s, 1H).

FAB-MS (m/s); 666 (M+1)$^+$

Example 77
Synthesis of Compound 78

The same procedure as in Example 74 was repeated using 50 mg (0.06 mmol) of Compound 70a and 1 ml of N-methylethanolamine to give 8.3 mg (21%) of Compound 78.

$^1$H-NMR (CDCl$_3$)δ; 1.60 (br, 2H), 2.18 (s, 3H), 2.31 (dd, 1H, J=4.9, 14.4 Hz), 2.40 (s, 3H), 2.41 (s, 3H), 2.64 (t, 2H, J=5.1 Hz), 2.66 (t, 2H, J=5.1 Hz), 3.01 (br, 4H), 3.26 (br, 5H), 3.59 (t, 2H, J=5.1, 14.4 Hz), 3.61 (t, 2H, J=5.1, 14.4 Hz), 4.08 (s, 3H), 4.89 (d, 1H, J=16.4 Hz), 4.98 (d, 1H, J=16.4 Hz), 6.19 (br, 1H), 6.85 (dd, 1H, J=4.9, 7.3 Hz), 7.28 (d, 1H, J=8.3 Hz), 7.31 (d, 1H, J=8.3 Hz), 7.38 (d, 1H, J=8.3 Hz), 7.69 (br, 1H), 7.72 (d, 1H, J=8.3 Hz), 9.09 (s, 1H).

FAB-MS (m/s); 670 (M+1)$^+$

Example 78
Synthesis of Compound 79

The same procedure as in Example 74 was repeated using 50 mg (0.06 mmol) of Compound 70a and 0.5 ml of a 1.0 N solution of methylamine in ethanol to give 12 mg (34%) of Compound 79.

hu 1H-NMR (CDCl$_3$)δ; 2.15 (s, 3H), 2.23 (br, 1H), 2.47 (s, 3H), 2.49 (s, 3H), 2.94 (br, 2H), 3.00 (br, 6H), 3.25 (dd, 1H, J=7.3, 14.4 Hz), 4.08 (s, 3H), 4.88 (d, 1H, J=16.6 Hz), 4.95 (d, 1H, J=16.6 Hz), 6.21 (br, 1H), 6.85 (dd, 1H, J=4.9, 7.1 Hz), 7.29 (d, 1H, J=8.3 Hz), 7.31 (d, 1H, J=8.3 Hz), 7.39 (d, 1H, J=8.3 Hz), 7.69 (s, 1H), 7.71 (d, 1H, J=8.3 Hz), 9.08 (s, 1H).

FAB-MS (m/s); 582 (M+1)$^+$

Example 79
Synthesis of Compound 80

To a solution of 78 mg (0.1 mmol) of Compound 70a in 3 ml of methylene chloride was added 0.78 ml (6.0 mmol) of p-methoxybenzylamine, followed by reflux for 1 day. Water was added to the reaction mixture, followed by extraction with chloroform/methanol (9/1). The extract was washed with a saturated aqueous solution of sodium chloride, and dried over sodium sulfate. After the solvent was evaporated under reduced pressure, the residue was purified by silica gel column chromatography (chloroform/methanol=10/1) to give 47 mg (59%) of Compound 80.

$^1$H-NMR (CDCl$_3$)δ; 2.16 (s, 3H), 2.33 (dd, 1H, J=4.9, 7.3 Hz), 3.02 (br, 8H), 3.25 (dd, 1H, J=7.3, 14.4 Hz), 3.764 (s, 3H), 3.769 (s, 3H), 3.773 (s, 4H), 4.08 (s, 3H), 4.79 (d, 1H, J=16.7 Hz), 4.87 (d, 1H, J=16.7 Hz), 6.10 (br, 1H), 6.63–7.03 (br, 5H), 7.10–7.34 (br, 7H), 7.67 (s, 1H), 7.71 (d, 1H, J=8.5 Hz), 9.05 (s, 1H).

FAB-MS (m/s); 794 (M+1)$^+$

Example 80
Synthesis of Compound 81

To a solution of 20 mg (0.026 mmol) of Compound 70a in 3 ml of dimethylsulfoxide was added 9.8 mg (0.15 mmol) of sodium azide, followed by stirring at room temperature overnight. Water was added to the reaction mixture, and precipitates were removed by filtration. After the filtrate was evaporated under reduced pressure, the residue was purified by silica gel column chromatography (chloroform/methanol=20/1) to give 14 mg (89%) of Compound 81.

$^1$H-NMR (DMSO-d$_6$)δ; 1.97 (dd, 1H, J=4.9, 13.9 Hz), 2.13 (s, 3H), 3.05 (t, 2H, J=7.0 Hz), 3.09 (t, 2H, J=7.0 Hz), 3.36 (dd, 1H, J=7.3, 13.9 Hz), 3.66 (t, 2H, J=7.0 Hz), 3.69 (t, 2H, J=7.0 Hz), 3.92 (s, 3H), 5.00 (br, 2H), 6.30 (s, 1H), 7.10 (dd, 1H, J=4.9, 7.3 Hz), 7.39 (dd, 1H, J=1.7, 8.3 Hz), 7.41 (dd, 1H, J=1.7, 8.3 Hz), 7.84 (d, 1H, J=8.3 Hz), 7.86 (d, 1H, J=8.3 Hz), 7.95 (dd, 1H, J=1.5 Hz), 8.62 (br, 1H), 9.09 (dd, 1H, J=1.5 Hz).

FAB-MS (m/s); 606 (M+1)$^+$

Example 81
Synthesis of Compound 82

The same procedure as in Example 74 was repeated using 50 mg (0.06 mmol) of Compound 73a and 2.0 ml of piperidine to give 16 mg (36%) of Compound 82.

$^1$H-NMR (CDCl$_3$)δ;1.43 (br, 4H), 1.60 (br, 12H), 1.90 (br, 4H), 2.20 (s, 3H) 2.31 (dd, 1H, J=4.9, 14.4 Hz), 2.38–2.50 (br, 8H), 2.78–2.86 (br, 4H), 3.27 (dd, 1H, J=7.3, 14.4 Hz), 4.09 (s, 3H), 4.97 (d, 2H, J=6.4 Hz), 6.07 (br, 1H), 6.86 (dd, 1H, J=4.9, 7.3 Hz), 7.30 (m, 2H), 7.38 (d, 1H, J=8.3 Hz), 7.700 (d, 1H, J=8.3 Hz), 7.703 (d, 1H, J=1.5 Hz), 9.07 (br, 1H).

FAB-MS (m/s); 718 (M+1)$^+$

Example 82
Synthesis of Compound 83

The same procedure as in Example 74 was repeated using 50 mg (0.06 mmol) of Compound 73a and 0.3 ml of morpholine to give 11 mg (26%) of Compound 83.

HNMR (DMSO-d$_6$)δ;1.81 (br, 4H), 1.97 (dd, 1H, J=4.6, 14.9 Hz), 2.19 (br, 12H), 2.21 (s, 3H), 2.83 (br, 4H), 3.59 (br, 9H), 3.92 (s, 3H), 4.98 (d, 2H, J=4.6 Hz), 6.28 (br, 1H), 7.07 (dd, 1H, J=4.6, 7.3 Hz), 7.32 (d, 1H, J=2.0, 8.8 Hz), 7.33 (d, 1H, J=2.0, 8.8 Hz), 7.77 (d, 1H, J=8.8 Hz), 7.81 (d, 1H, J=8.8 Hz), 7.83 (d, 1H, J=1.0 Hz), 8.57 (s, 1H), 9.04 (d, 1H, J=1.0 Hz).

FAB-MS (m/s); 722 (M+1)$^+$

Example 83
Synthesis of Compound 84

The same procedure as in Example 74 was repeated using 50 mg (0.06 mmol) of Compound 73a and 0.5 ml of diethylamine to give 7.9 mg (19%) of Compound 84.

$^1$H-NMR (DMSO-d$_6$)δ; 0.97 (t, 6H, J=7.1 Hz), 0.98 (t, 6H, J=7.1 Hz), 1.81 (br, 12H), 1.97 (dd, 1H, J=4.9, 14.5 Hz), 2.12 (s, 3H), 2.28 (t, 2H, J=8.8 Hz), 2.30 (t, 2H, J=8.8 Hz), 2.41–2.49 (br, 4H), 3.30 (br, 1H), 3.92 (s, 3H), 4.99 (d, 2H, J=5.4 Hz), 6.28 (s, 1H), 7.07 (dd, 1H, J=4.9, 7.3 Hz), 7.32

(dd, 1H, J=1.9, 8.5 Hz), 7.33 (dd, 1H, J=1.9, 8.5 Hz), 7.77 (d, 1H, J=8.5 Hz), 7.81 (s, 1H), 7.83 (d, 1H, J=8.5 Hz), 8.56 (s, 1H), 9.04 (d, 1H, J=1.5 Hz).

FAB-MS (m/s); 694 (M+1)$^+$

Example 84
Synthesis of Compound 85
Step A

To a solution of 1.0 g (1.25 mmol) of Compound 73a in 10 ml of dimethylsulfoxide was added 488 mg (7.5 mmol) of sodium azide, followed by stirring at room temperature overnight. Water was added to the reaction mixture, and precipitates were collected by filtration. To a solution of 310 mg (about 0.43 mmol) of the obtained product in 5.0 ml of chloroform/methanol (9/1) was added 2.6 g (10 mmol) of triphenylphosphine, followed by stirring at room temperature overnight. To the reaction mixture was added water, followed by extraction with chloroform/methanol (9/1). The extract was washed with a saturated aqueous solution of sodium chloride, and dried over sodium sulfate. The solvent was evaporated under reduced pressure to give 497 mg (quantitative) of a diamino compound.

Step B

To a solution of 58 mg (0.1 mmol) of the diamino compound in 2.0 ml of methylene chloride was added 0.075 ml (0.5 mmol) of ethyl isocyanate, followed by stirring at room temperature overnight. To the reaction mixture was added water, followed by extraction with chloroform/methanol. The extract was washed with a saturated aqueous solution of sodium chloride, and dried over sodium sulfate. After the solvent was evaporated under reduced pressure, the residue was purified by silica gel column chromatography (chloroform/methanol=10/1) to give 2.0 mg (2.7%) of Compound 85.

$^1$H-NMR (DMSO-d$_6$)δ; 0.99 (t, 3H, J=7.2 Hz), 1.00 (t, 3H, J=7.2 Hz), 1.78 (br, 4H), 1.97 (dd, 1H, J=4.8, 14.1 Hz), 2.12 (s, 3H), 2.76 (br, 4H), 3.10 (br, 8H), 3.37 (br, 1H), 3.92 (s, 3H), 5.00 (br, 2H), 5.74 (br, 2H), 5.86 (br, 2H), 6.28 (br, 1H), 7.07 (dd, 1H, J=4.8, 7.3 Hz), 7.31 (d, 2H, J=8.4 Hz), 7.78 (d, 1H, J=8.4 Hz), 7.82 (s, 1H), 7.83 (d, 1H, J=8.4 Hz), 8.58 (s, 1H), 9.03 (d, 1H, J=1.5 Hz).

FAB-MS (m/s); 724 (M+1)$^+$

Example 85
Synthesis of Compound 86

To a solution of 58 mg (0.1 mmol) of the diamino compound obtained in Example 84, Step A in 2.0 ml of methylene chloride were added 0.5 ml of pyridine and 91 mg (0.5 mmol) of di-t-butyl dicarbonate, followed by stirring at room temperature overnight. To the reaction mixture was added water, followed by extraction with chloroform/methanol(9/1). The extract was washed with a saturated aqueous solution of sodium chloride, and dried over sodium sulfate. After the solvent was evaporated under reduced pressure, the residue was purified by silica gel column chromatography (chloroform/methanol=10/1) to give 8.0 mg (10%) of Compound 86.

$^1$H-NMR (CDCl$_3$)δ; 1.45 (s, 18H), 1.92 (br, 4H), 2.19 (s, 3H), 2.40 (dd, 1H, J=4.6, 14.4 Hz), 2.80 (br, 4H), 3.23 (br, 4H), 3.31 (dd, 1H, J=7.3, 14.4 Hz), 4.09 (s, 3H), 4.67 (br, 2H), 4.79 (d, 1H, J=16.4 Hz), 4.89 (d, 1H, J=16.4 Hz), 5.98 (br, 1H), 6.85 (dd, 1H, J=4.6, 7.3 Hz), 7.25–7.29 (m, 2H), 7.35 (d, 1H, J=8.3 Hz), 7.65 (br, 1H), 7.73 (d, 1H, J=8.3 Hz), 8.95 (s, 1H).

FAB-MS (m/s); 782 (M+1)$^+$

Example 86
Synthesis of Compound 87

The same procedure as in Example 68 was repeated using 45 mg (0.070 mmol) of Compound 43 to give 20 mg (46%) of Compound 87.

$^1$H-NMR (CDCl$_3$)δ; 1.97 (dd, 1H, J=4.9, 13.8 Hz), 2.14 (s, 6H), 2.16 (s, 3H), 2.79–2.89 (br, 4H), 2.97–3.09 (br, 4H), 3.35 (dd, 1H, J=7.3, 13.8 Hz), 3.92 (s, 3H), 5.00 (br, 2H), 6.29 (s, 1H), 7.09 (dd, 1H, J=4.9, 7.3 Hz), 7.36 (dd, 1H, J=1.7, 8.5 Hz), 7.38 (dd, 1H, J=1.7, 8.5 Hz), 7.80 (d, 1H, J=8.5 Hz), 7.83 (d, 1H, J=8.5 Hz), 7.90 (d, 1H, J=1.5 Hz), 8.59 (br, 1H), 9.05 (d, 1H, J=1.2 Hz).

FAB-MS (m/s); 616 (M+1)$^+$

Example 87
Synthesis of Compound 88

The same procedure as in Example 68 was repeated using 886 mg (1.3 mmol) of Compound 44 to give 710 mg (85%) of Compound 88.

$^1$H-NMR (CDCl$_3$)δ; 1.31 (t, 3H, J=7.3 Hz), 1.33 (t, 3H, J=7.3 Hz), 2.18 (s, 3H), 2.60–2.68 (m, 5H), 2.86 (br, 2H), 2.94 (br, 2H), 3.06 (br, 2H), 3.12 (br, 2H), 3.37 (dd, 1H, J=7.3, 14.1 Hz), 4.09 (s, 3H), 4.75 (d, 1H, J=16.1 Hz), 4.83 (d, 1H, J=16.1 Hz), 5.73 (s, 1H), 6.82 (dd, 1H, J=4.9, 7.3 Hz), 7.24 (dd, 1H, J=1.7, 8.3 Hz), 7.29 (d, 1H, J=8.3 Hz), 7.33 (dd, 1H, J=1.7, 8.5 Hz), 7.71 (d, 1H, J=1.2 Hz), 7.80 (d, 1H, J=8.5 Hz), 8.85 (br, 1H).

FAB-MS (m/s); 644 (M+1)$^+$

Example 88
Synthesis of Compound 89

To a solution of 77 mg (0.1 mmol) of Compound 70a in 2 ml of N,N-dimethylformamide were added 0.025 ml (0.24 mmol) of methyl 2-mercaptoacetate and 138 mg (1.0 mmol) of potassium carbonate, followed by stirring at room temperature for 2 hours. To the reaction mixture was added water, followed by extration with chloroform/methanol(9/1). The extract was washed with a saturated aqueous solution of sodium chloride, and dried over sodium sulfate. After the solvent was evaporated under reduced pressure, the residue was purified by silica gel column chromatography (chloroform/methanol=20/1) to give 37 mg (51%) of Compound 89.

$^1$H-NMR (CDCl$_3$)δ; 1.96 (dd, 1H, J=5.3, 14.0 Hz), 2.13 (s, 3H), 3.00 (br, 8H), 3.30 (br, 1H), 3.43 (s, 2H), 3.46 (s, 2H), 3.67 (s, 3H), 3.68 (s, 3H), 3.91 (s, 3H), 5.01 (br, 2H), 6.31 (br, 1H), 7.09 (dd, 1H, J=5.3, 7.7 Hz), 7.35 (dd, 1H, J=1.6, 8.7 Hz), 7.37 (dd, 1H, J=1.6, 8.7 Hz), 7.81 (d, 1H, J=8.7 Hz), 7.84 (d, 1H, J=8.7 Hz), 7.89 (s, 1H), 8.62 (s, 1H), 9.04 (s, 1H).

FAB-MS (m/s); 732 (M+1)$^+$

Example 89
Synthesis of Compound 90

The same procedure as in Example 88 was repeated using 77 mg (0.1 mmol) of Compound 70a and 0.027 ml (0.24 mmol) of ethyl 3-mercaptopropionate to give 43 mg (55%) of Compound 90.

$^1$H-NMR (CDCl$_3$)δ; 1.23 (t, 3H, J=7.1 Hz), 1.26 (t, 3H, J=7.1 Hz), 2.18 (br, 3H), 2.59–3.62 (br, 5H), 2.83–2.89 (m, 6H), 2.96 (br, 2H), 3.02–3.07 (br, 2H), 3.10–3.16 (m, 2H), 3.37 (dd, 1H, J=7.6, 14.4 Hz), 4.08 (s, 3H), 4.15 (m, 4H), 4.73 (d, 1H, J=16.6 Hz), 4.75 (br, 1H), 4.83 (d, 1H, J=16.6 Hz), 5.76 (br, 1H), 6.83 (dt, 1H, J=4.9, 7.6 Hz), 7.23 (dd, 1H, J=8.7 Hz), 7.27 (d, 1H, J=8.8 Hz), 7.32 (dd, 1H, J=1.7, 8.8 Hz), 7.70 (s, 1H), 7.80 (d, 1H, J=8.8 Hz), 8.83 (s, 1H).

FAB-MS (m/s); 788 (M+1)$^+$

Example 90
Synthesis of Compound 91

The same procedure as in Example 68 was repeated using 65 mg (0.081 mmol) of Compound 50 to give 42 mg (67%) of Compound 91.

$^1$H-NMR (DMSO-d$_6$)δ; 1.97 (dd, 1H, J=4.7, 7.9 Hz), 2.08 (s, 3H), 3.00–3.05 (br, 4H), 3.15–3.21 (br, 4H), 3.39 (br, 1H), 3.91 (s, 3H), 5.00 (br, 2H), 6.30 (s, 1H), 6.79 (dt, 4H, J=2.2, 8.8 Hz), 7.32 (br, 10H), 7.79 (d, 1H, J=8.6 Hz), 7.83 (d, 1H, J=8.6 Hz), 7.86 (s, 1H), 9.04 (d, 1H, J=1.2 Hz), 9.54 (s, 1H), 9.55 (s, 1H).

FAB-MS (m/s); 772 (M+1)$^+$

Example 91
Synthesis of Compound 92

The same procedure as in Example 68 was repeated using 38 mg (0.05 mmol) of Compound 51 to give 22 mg (56%) of Compound 92.

$^1$H-NMR (DMSO-d$_6$)δ; 1.97 (dd, 1H, J=4.9, 13.8 Hz), 2.06 (s, 8H), 2.13 (s, 3H), 3.21–3.25 (m, 4H), 3.36 (dd, 1H, J=7.3, 13.8 Hz), 3.92 (s, 3H), 3.94 (t, 2H, J=7.3 Hz), 3.97 (t, 2H, J=7.3 Hz), 5.01 (br, 2H), 6.30 (br, 1H), 7.10 (dd, 1H, J=4.9, 7.3 Hz), 7.40 (d, 1H, J=1.7, 8.3 Hz), 7.42 (dd, 1H, J=1.7, 8.3 Hz), 7.84 (d, 1H, J=7.3 Hz), 7.86 (d, 1H, J=8.3 Hz), 7.98 (d, 1H, J=1.4 Hz), 8.63 (br, 1H), 9.08 (d, 1H, J=1.2 Hz).

FAB-MS (m/s); 756 (M+1)$^+$

Example 92
Synthesis of Compound 93

The same procedure as in Example 46 was repeated using 31 mg (0.05 mmol) of Compound 69 to give 10 mg (26%) of Compound 93.

$^1$H-NMR (CDCl$_3$)δ; 2.28 (s, 3H), 2.30 (dd, 1H, J=4.9, 14.2 Hz), 3.17–3.21 (br, 2H), 3.33 (t, 2H, J=7.3 Hz), 3.42–3.46 (m, 3H), 3.48–3.52 (m, 2H), 3.63 (t, 2H, J=7.2 Hz), 4.09 (s, 3H), 4.99 (br, 1H), 6.27 (br, 1H), 6.88 (dd, 1H, J=4.9, 7.0 Hz), 7.09 (d, 2H, J=6.4 Hz), 7.12 (d, 2H, J=6.4 Hz), 7.31 (dd, 1H, J=1.5, 8.3 Hz), 7.33 (dd, 1H, J=1.7, 8.3 Hz), 7.43 (d, 1H, J=8.3 Hz), 7.68 (s, 1H), 7.76 (d, 1H, J=8.4 Hz), 8.21 (d, 2H, J=6.4 Hz), 8.34 (d, 2H, J=6.4 Hz), 9.19 (s, 1H).

FAB-MS (m/s); 742 (M+1)$^+$

Example 93
Synthesis of Compound 94

The same procedure as in Example 47 was repeated using 77 mg (0.1 mmol) of Compound 70a to give 21 mg (28%) of Compound 94.

$^1$H-NMR (CDCl$_3$) δ; 2.16 (s, 3H), 2.78 (dd, 1H, J=4.7, 14.4 Hz), 3.14 (br, 2H), 3.27 (t, 2H, J=7.2 Hz), 3.41 (dd, 1H, J=7.4, 14.4 Hz), 3.50 (br, 2H), 3.63 (t, 2H, J=7.2 Hz), 4.03 (s, 3H), 4.69 (br, 1H), 5.08 (br, 1H), 5.45 (br, 3H), 6.79 (dd, 1H, J=4.7, 7.4 Hz), 6.99 (br, 2H), 7.25 (br, 4H), 7.40 (dd, 1H, J=1.7, 8.5 Hz), 7.48 (br, 2H), 7.75 (s, 1H,), 7.85 (d, 1H, J=8.5 Hz), 8.52 (br, 2H), 8.78 (s, 1H).

FAB-MS (m/s); 742 (M+1)$^+$

Example 94
Synthesis of Compound 95

The same procedure as in Example 68 was repeated using 60 mg (0.089 mmol) of Compound 53 to give 20 mg (35%) of Compound 95.

$^1$H-NMR (DMSO-d$_6$) δ; 1.95 (m, 5H), 2.08 (s, 3H), 2.09 (s, 3H), 2.13 (s, 3H), 2.55 (t, 4H , J=7.6 Hz), 2.86 (t, 2H, J=7.6 Hz), 2.88 (t, 2H, J=7.6 Hz), 3.34 (dd, 1H, J=7.3, 14.1 Hz), 3.92 (s, 3H), 4.99 (d, 2H, J=4.9 Hz), 6.28 (s, 1H), 7.08 (dd, 1H, J=4.9, 7.3 Hz), 7.32 (dd, 1H, J=2.7, 8.5 Hz), 7.38 (dd, 1H, J=1.7, 8.5 Hz), 7.79 (d, 1H, J=8.5 Hz), 7.83 (d, 1H, J=1.2 Hz), 7.84 (d, 1H, J=8.5 Hz), 8.57 (br, 1H), 9.04 (s, 1H).

FAB-MS (m/s); 644 (M+1)$^+$

Example 95
Synthesis of Compound 96

The same procedure as in Example 88 was repeated using 80 mg (0.1 mmol) of Compound 73a and 34 mg (0.20 mmol) of 2-mercaptobenzothiazole to give 35 mg (40%) of Compound 96.

$^1$H-NMR (DMSO-d$_6$) δ; 1.97 (dd, 1H, J=4.9, 14.0 Hz), 2.12 (s, 3H), 2.18–2.22 (m, 4H), 2.96–3.00 (m, 4H), 3.33 (br, 3H), 3.44 (t, 2H, J=2.8 Hz), 3.91 (s, 3H), 4.97 (br, 2H), 6.29 (s, 1H), 7.08 (dd, 1H, J=4.9, 7.3 Hz), 7.26–7.52 (m, 6H), 7.80–8.00 (m, 7H), 8.56 (br, 1H), 9.07 (d, 1H, J=1.2 Hz).

FAB-MS (m/s); 882 (M+1)$^+$

Example 96
Synthesis of Compound 97

To a solution of 335 mg (1.5 mmol) of palladium (II) acetate in 5 ml of N,N-dimethylformamide was added 1.82 mg (6.0 mmol) of bis(o-tolyl)phosphine, followed by stirring in an argon stream at room temperature for 30 minutes. To the mixture were added a solution of 3.29 g (5.0 mmol) of Compound B in 30 ml of N,N-dimethylformamide, 0.60 ml (80 mmol) of triethylamine and 0.28 ml (2.1 mmol) of 2-vinylpyridine, followed by stirring at 60_C. for 3 hours. After the solvent was evaporated under reduced pressure, the residue was purified by silica gel column chromatography (chloroform/methanol=50/1) to give 2.24 g (66%) of Compound 97.

$^1$H-NMR (DMSO-d$_6$) δ; 1.79 (s, 3H), 2.13 (dd, 1H, J=5.1, 15.4 Hz), 2.32 (s, 3H), 2.77 (s, 3H), 3.99 (dd, 1H, J=7.3, 15.4 Hz), 4.02 (s, 3H), 5.35 (br, 2H), 6.98 (dd, 1H, J=5.1, 7.3 Hz), 7.15 (ddd, 1H, J=1.0, 4.8, 7.8 Hz), 7.47 (d, 1H, J=8.8 Hz), 7.48 (d, 1H, J=7.8 Hz), 7.69 (dt, 1H, J=1.7, 8.8 Hz), 7.78 (dd, 1H, J=1.7, 8.8 Hz), 7.83 (d, 1H, J=16.1 Hz), 8.01 (br, 2H), 8.08 (dd, 1H, J=1.7, 7.8 Hz), 8.46 (d, 1H, J=1.5 Hz), 8.63 (ddd, 1H, J=0.7, 1.7, 4.9 Hz), 9.29 (d, 1H, J=1.5 Hz), 10.20 (s, 1H).

FAB-MS (m/s); 683 (M+1)$^+$

Example 97
Synthesis of Compound 98

The same procedure as in Example 57 was repeated using 1.0 g (1.4 mmol) of Compound 97 to give 870 mg (87%) of Compound 98.

FAB-MS (m/s); 685 (M+1)$^+$

Example 98
Synthesis of Compound 99

The same procedure as in Example 1, Step B was repeated using 174 mg (0.25 mmol) of Compound 98 to give 150 mg (98%) of Compound 99.

$^1$H-NMR (DMSO-d$_6$) δ; 2.04 (dd, 1H, J=4.9,13.9 Hz), 2.15 (s, 3H), 3.42 (dd, 1H, J=7.3, 13.9 Hz), 4.72 (s, 2H), 5.02 (d, 1H, J=5.4 Hz), 6.34 (s, 1H), 7.17 (dd, 1H, J=4.9, 7.3 Hz), 7.26–7.29 (m, 2H), 7.30 (d, 1H, J=16.1 Hz), 7.46 (dd, 1H, J=1.5, 8.1 Hz), 7.65 (d, 1H, J=8.1 Hz), 7.85–7.89 (m, 6H), 8.61 (dd, 1H, J=1.0. 3.9 Hz), 9.46 (d, 1H, J=1.2 Hz).FAB-MS (m/s); 685 (M+1)$^+$

Example 99
Synthesis of Compound 100

To a solution of 100 mg (0.15 mmol) of Compound 98 in 5 ml of methylene chloride were added 54 mg (0.36 mmol) of t-butyldimethylsilyl chloride, 75 mg (0.75 mmol) of imidazole and 0.5 ml of triethylamine, followed by stirring for 1 hour. The reaction mixture was poured into ice-cold water, followed by extraction with chloroform. The extract was washed with a saturated aqueous solution of sodium chloride, and dried over sodium sulfate. After the solvent was evaporated under reduced pressure, the residue was triturated with hexane to give 110 mg (92%) of Compound 100.

FAB-MS (m/z); 799 (M+1)$^+$

Example 100
Synthesis of Compound 101

The same procedure as in Example 1, Step B was repeated using 40 mg (0.25 mmol) of Compound 100 to give 27 mg (68%) of Compound 101.

$^1$H-NMR (CDCl$_3$) δ; 0.21 (s, 6H), 1.03 (s, 9H), 2.15 (s, 3H), 2.84 (dd, 1H, J=4.9, 14.4 Hz), 3.50 (dd, 1H, J=7.5, 14.4 Hz), 4.03 (s, 3H), 4.46 (d, 1H, J=16.4 Hz), 4.63 (d, 1H, J=16.4 Hz), 4.94 (s, 2H), 5.52 (br, 1H), 6.73 (dd, 1H, J=4.9, 7.5 Hz), 7.14 (br, 2H), 7.16 (d, 1H, J=8.5 Hz), 7.42 (d, 1H, J=7.5 Hz), 7.44 (dd, 1H, J=1.5, 8.5 Hz), 7.50 (dd, 1H, J=1.5, 8.5 Hz), 7.66 (dt, 1H, J=1.7, 7.5 Hz), 7.71 (d, 1H, J=16.1 Hz), 7.74 (s, 1H), 7.88 (d, 1H, J=8.5 Hz), 8.61 (d, 1H, J=3.9 Hz), 8.95 (s, 1H).

FAB-MS (m/z); 715 (M+1)$^+$

Example 101
Synthesis of Compound 102

To a solution of 90 mg (0.15 mmol) of Compound 99 in 3.0 ml of chloroform/methanol (5/1) was added 104 mg (0.45 mmol) of camphor sulfonic acid, followed by stirring at room temperature for 1 day. The reaction mixture was poured into a saturated aqueous solution of sodium hydrogen carbonate, followed by extraction with chloroform/methanol (9/1). The extract was washed with a saturated aqueous solution of sodium chloride, and dried over sodium sulfate. After the solvent was evaporated under reduced pressure, the residue was purified by silica gel column chromatography (chloroform/methanol=20/1) to give 64 mg (52%) of Compound 102.

$^1$H-NMR (DMSO-d$_6$) δ; 2.04 (dd, 1H, J=4.9, 14.1 Hz), 2.15 (s, 3H), 3.37 (s, 3H), 3.41 (dd, 1H, J=7.5, 14.1 Hz), 3.93 (s, 3H), 4.63 (s, 2H), 5.01 (d, 1H, J=17.2 Hz), 5.06 (d, 1H, J=17.2 Hz), 6.38 (s, 1H), 7.17 (dd, 1H, J=4.9,7.3 Hz), 7.24 (m, 1H), 7.29 (d, 1H, J=16.0 Hz), 7.46 (dd, 1H, J=1.7, 8.7 Hz), 7.61 (d, 1H, J=7.6 Hz), 7.79 (dt, 1H, J=1.7, 7.6 Hz), 7.87 (dd, 1H, J=1.7, 8.7 Hz), 7.88 (d, 1H, J=16.0 Hz), 7.92 (d, 1H, J=8.7 Hz), 7.99 (d, 1H, J=1.0 Hz), 8.59 (d, 1H, J=3.8 Hz), 8.69 (s, 1H), 9.45 (d, 1H, J=1.4 Hz).

FAB-MS (m/s); 615 (M+1)$^+$

Example 102
Synthesis of Compound 103

The same procedure as in Example 101 was repeated using a solution of 60 mg (0.10 mmol) of Compound 99 in 3.0 ml of methylene chloride/ethanol (2/1) and 255 mg (1.1 mol) of camphorsulfonic acid to give 23 mg (41%) of Compound 103.

$^1$H-NMR (CDCl$_3$) δ; 1.33 (t, 3H, J=6.9 Hz), 2.18 (s, 3H), 2.62 (dd, 1H, J=4.9, 14.5 Hz), 3.44 (dd, 1H, J=7.4, 14.5 Hz), 3.66 (q, 2H, J=6.9 Hz), 4.08 (s, 3H), 4.67 (d, 1H, J=15.9 Hz), 4.71 (s, 2H), 4.82 (d, 1H, J=15.9 Hz), 5.77 (s, 1H), 6.82 (dd, 1H, J=4.9, 7.4 Hz), 7.14 (ddd, 1H, J=1.0, 4.9, 7.6 Hz), 7.21 (d, 1H, J=16.1 Hz), 7.32 (d, 1H, J=8.8 Hz), 7.46 (d, 1H, J=8.8 Hz), 7.47 (d, 1H, J=8.6 Hz), 7.64 (dd, 1H, J=1.7, 7.6 Hz), 7.68 (dt, 1H, J=1.7, 7.6 Hz), 7.80 (d, 1H, J=16.1 Hz), 7.83 (d, 1H, J=1.2 Hz), 7.83 (d, 1H, J=8.3 Hz), 8.63 (dd, 1H, J=0.7, 3.9 Hz), 9.21 (d, 1H, J=1.2 Hz).

FAB-MS (m/s); 629 (M+1)$^+$

Example 103
Synthesis of Compound 104

To a solution of 137 mg (0.20 mmol) of Compound 98 in 3.0 ml of methylene chloride was added 0.13 ml (2.0 mmol) of N,N-dimethylethanolamine and 510 mg (2.2 mol) of camphorsulfonic acid, followed by reflux for 1 day. The reaction was poured into a saturated aqueous solution of sodium hydrogen carbonate, followed by extraction with chloroform/methanol (9/1). The extract was washed with a saturated aqueous solution of sodium chloride, and dried over sodium sulfate. The solvent was evaporated under reduced pressure to give diacetylated Compound 104. The same procedure as in Example 1, Step B was repeated using the obtained diacetylated compound to give 21 mg (16%) of Compound 104.

$^{11}$H-NMR (DMSO-d$_6$) δ; 2.03 (dd, 1H, J=4.9, 14.2 Hz), 2.15 (s, 3H), 2.21 (m, 8H), 3.42 (m, 1H), 3.60 (t, 2H, J=5.9 Hz), 3.93 (s, 3H), 4.69 (s, 2H), 4.99 (d, 1 H, J=17.1 Hz), 5.05 (d, 1H, J=17.1 Hz), 6.37 (s, 1H), 7.17 (dd, 1H, J=4.9, 7.3 Hz), 7.24 (m, 1H), 7.30 (d, 1H, J=16.0 Hz), 7.46 (dd, 1H, J=1.5, 8.7 Hz), 7.61 (d, 1H, J=7.9 Hz), 7.67–7.97 (m, 5H), 8.00 (s, 1H), 8.58 (m, 1H), 8.69 (s, 1H), 9.45 (d, 1H, J=1.6 Hz).

FAB-MS (m/s); 672 (M+1)$^+$

Example 104
Synthesis of Compound 105

To a solution of 60 mg (0.10 mmol) of Compound 99 in 2 ml of methylene chloride was added 0.042 ml (0.3 mmol) of trifluoroacetic anhydride, followed by stirring for 20 minutes. To the mixture was added 0.022 ml (0.3 mmol) of ethanethiol, followed by stirring overnight. The reaction mixture was poured into a saturated aqueous solution of sodium hydrogencarbonate, followed by extraction with chloroform/methanol. The exact was washed with a saturated aqueous solution of sodium chloride, and dried over sodium sulfate. After the solvent was evaporated under reduced pressure, the residue was purified by silica gel column chromatography (chloroform/methanol=20/1) to give 26 mg (25%) of Compound 105.

$^1$H-NMR (CDCl$_3$) δ; 1.33 (t, 3H, J=7.3 Hz), 2.18 (s, 3H), 2.56 (q, 2H, J=7.3 Hz), 2.68 (dd, 1H, J=4.9, 14.4 Hz), 3.46 (dd, 1H, J=7.3, 14.4 Hz), 3.85 (s, 2H), 4.08 (s, 3H), 4.65 (d, 1H, J=16.4 Hz), 4.69 (d, 1H, J=16.4 Hz), 5.75 (s, 2H), 6.81 (dd, 1H, J=4.9, 7.3 Hz), 7.18 (m, 1H), 7.19 (d, 1H, J=15.9 Hz), 7.28 (dd, 1H, J=1.7, 8.8 Hz), 7.43 (dd, 1H, J=1.7, 8.8 Hz), 7.46 (d, 1H, J=7.6 Hz), 7.60 (d, 1H, J=8.8 Hz), 7.68 (dt, 1H, J=1.5, 7.6 Hz), 7.79 (br, 3H), 8.62 (dd, 1H, =0.4, 3.7 Hz), 9.13 (s, 1H).

FAB-MS (m/s); 645 (M+1)$^+$

Example 105
Synthesis of Compound 106

The same procedure as in Example 103 was repeated using a solution of 137 mg (0.20 mmol) of Compound 98 in 3.0 ml of methylene chloride, 113 mg (0.8 mmol) of N,N-dimethylethanethiol hydrochloride and 510 mg (2.2 mmol) of camphorsulfonic acid to give 6.1 mg (4.3%) of Compound 106.

$^1$H-NMR (DMSO-d$_6$) δ; 2.03 (dd, 1H, J=4.9, 14.2 Hz), 2.14 (s, 3H), 2.19 (s, 6H), 2.52 (br, 4H), 3.40 (br, 1H), 3.93 (s, 3H), 3.99 (s, 2H), 4.99 (d, 1H, J=17.1 Hz), 5.03 (d, 1H, J=17.1 Hz), 6.37 (s,1H), 7.17 (dd, 1H, J=4.9, 7.4 Hz), 7.23 (m, 1H), 7.30 (d, 1H, J=15.9 Hz), 7.47 (dd, 1H, J=1.7, 8.9

Hz), 7.60 (d, 1H, J=7.6 Hz), 7.79 (dd, 1H, J=1.8, 8.9 Hz), 7.87 (dd, 1H, J=1.7, 8.9 Hz), 7.88 (d, 1H, J=15.9 Hz), 7.90 (d, 1H, J=8.7 Hz), 7.95 (d, 1H, J=8.7 Hz), 7.97 (d, 1H, J=1.5 Hz), 8.58 (m, 1H), 8.70 (s, 1H), 9.45 (d, 1H, J=1.5 Hz).
FAB-MS (m/s); 688 (M+1)$^+$

Example 106
Synthesis of Compound 107

The same procedure as in Example 103 was repeated using a solution of 137 mg (0.20 mmol) of Compound 98 in 3.0 ml of methylene chloride, 111 mg (1.0 mmol) of 2-mercaptopyridine and 510 mg (2.2 mmol) of camphorsulfonic acid to give 33 mg (24%) of Compound 107.

$^1$HNMR (DMSO-d$_6$) δ; 2.00 (dd, 1H, J=4.9, 14.5 Hz), 2.13 (s,3H), 3.40 (br, 1H), 3.92 (s, 3H), 4.66 (s, 2H), 4.95 (d, 1H, J=17.6 Hz), 4.99 (d, 1H, J=17.6 Hz), 6.32 (s, 1H), 7.16 (dd, 2H, J=4.9, 7.6 Hz), 7.24 (br, 1H), 7.29 (d, 1H), 7.36 (d, 1H, J=7.6 Hz), 7.54 (dd, 1H, J=1.7, 8.7 Hz), 7.60 (d, 1H, J=7.6 Hz), 7.67 (dt, 1H, J=1.7, 7.6 Hz), 7.79 (dt, 1H, J=1.7, 7.6 Hz), 7.88 (br, 3H), 7.94 (d, 1H, J=8.8 Hz), 8.10 (d, 1H, J=1.5 Hz), 8.53 (br, 1H), 8.58 (br, 1H), 8.67 (s, 1H), 9.44 (d, 1H, J=1.2 Hz).
FAB-MS (m/s); 694 (M+1)$^+$

Example 107
Synthesis of Compound 108

The same procedure as in Example 103 was repeated using a solution of 68 mg (0.10 mmol) of Compound 98 in 3.0 ml of methylene chloride, 150 mg (1.0 mmol) of 2-mercaptobenzimidazole and 510 mg (2.2 mmol) of camphorsulfonic acid to give 22 mg (30%) of Compound 108.

$^1$H-NMR (DMSO-d$_6$) δ; 1.99 (dd, 1H, J=4.9, 14.1 Hz), 2.12 (s, 3H), 3.38 (dd, 1H, J=4.9, 6.9 Hz), 3.92 (s, 3H), 4.79 (d, 2H, J=3.4Hz), 4.84 (d, 1H, J=16.4 Hz), 4.93 (d, 1H, J=16.4 Hz), 6.30 (s, 1H), 7.18 (br, 5H), 7.24 (d, 1H, J=15.9 Hz), 7.28 (dd, 1H, J=15.9 Hz), 7.38 (dd, J=1.9, 7.6 Hz), 7.60 (br, 2H), 7.79 (dt, 1H, J=1.9, 7.6 Hz), 7.87 (br, 2H), 7.94 (d, 1H, J=8.6 Hz), 8.15 (s, 1H), 8.59 (d, 1H, J=1.8 Hz), 9.21 (s, 1H), 9.43 (s, 1H), 12.2 (s, 1H).
FAB-MS (m/s); 733 (M+1)$^+$

Example 108
Synthesis of Compound 109

To a suspension of 68 mg (0.10 mmol) of Compound 97 in 3.0 ml of methylene chloride were added 0.016 ml (0.22 mmol) of ethanethiol, and 0.018 ml (0.15 mol) of boron trifluoride etherate, followed by stirring at room temperature for 1 hour. The reaction mixture was poured into a saturated aqueous solution of sodium hydrogencarbonate, followed by extraction with chloroform. The extract was washed with a saturated aqueous solution of sodium chloride, and dried over sodium sulfate. After the solvent was evaporated under reduced pressure, the residue was purified by silica gel column chromatophy (chloroform/methanol=20/) to give 21 mg (27%) of Compound 109.
FAB-MS (m/s); 789 (M+1)$^+$ Example 109
Synthesis of Compound 110

The same procedure as in Example 1, Step B was repeated using 21 mg (0.25 mmol) of Compound 109 to give 15 mg (88%) of Compound 110.

$^1$H-NMR (DMSO-d$_6$) δ; 1.22 (dt, 6H, J=2.5, 7.3 Hz), 2.03 (dd, 1H, J=4.9, 14.1 Hz), 2.15 (s, 3H), 2.58 (br, 4H), 3.41 (dd, 1H, J=7.3, 14.1 Hz), 3.93 (s, 3H), 4.98 (d, 1H, J=17.1 Hz), 5.04 (d, 1H, J=17.1 Hz), 5.43 (s, 1H), 6.35 (s, 1H), 7.18 (dd, 1H, J=4.9, 7.3 Hz), 7.25 (br, 1H), 7.30 (d, 1H, J=16.1 Hz), 7.61 (br, 2H), 7.80 (dt, 1H, J=1.7, 7.6 Hz), 7.88 (d, 1H, J=16.1 Hz), 7.89 (d, 1H, J=16.1 Hz), 7.93 (d, 1H, J=8.8 Hz), 7.96 (d, 1H, J=8.8 Hz), 8.09 (d, 1H, J=1.4 Hz), 8.59 (dd, 1H, J=0.8, 3.2 Hz), 8.71 (s, 1H), 9.45 (d, 1H, J=0.6 Hz).
FAB-MS (m/s); 705 (M+1)$^+$

Example 110
Synthesis of Compound 111

The same procedure as in Example 96 was repeated using 1.5 g (2.1 mmol) of Compound J to give 893 mg (62%) of Compound 111.

$^1$H-NMR (CDCl$_3$) δ; 1.81 (s, 3H), 2.16 (dd, 1H, J=5.1, 14.6 Hz), 2.34 (s, 3H), 2.75 (s, 3H), 4.01 (dd, 1H, J=7.3, 14.6 Hz), 4.03 (s, 3H), 5.31 (d, 2H, J=2.0 Hz), 6.99 (dd, 1H, J=5.1, 7.3 Hz), 7.18 (ddd, 1H, J=1.0, 4.9, 7.6 Hz), 7.30 (d, 1H, J=16.1 Hz), 7.52 (d, 1H, J=7.6 Hz), 7.56 (d, 1H, J=8.8 Hz), 7.72 (dt, 1H, J=1.7, 7.6 Hz), 7.82 (dd, 1H, J=1.7, 8.8 Hz), 7.85 (d, 1H, J=8.8 Hz), 7.93 (d, 1H, J=8.8 Hz), 8.03 (dd, 1H, J=1.5, 8.8 Hz), 8.09 (d, 1H, J=1.3 Hz), 8.66 (dd, 1H, J=1.0, 4.6 Hz), 9.57 (d, 1H, J=1.6 Hz), 10.16 (s, 1H).
FAB-MS (m/z); 683 (M+1)$^+$ Example 111
Synthesis of Compound 112

The same procedure as in Example 57 was repeated using 750 mg (1.1 mmol) of Compound 111 to give 620 mg (82%) of Compound 112.
FAB-MS (m/z); 685 (M+1)$^+$ Example 112
Synthesis of Compound 113

The same procedure as in Example 1, Step B was repeated using 620 mg (0.91 mmol) of Compound 112 to give 450 mg (83%) of Compound 113.

$^1$H-NMR (CDCl$_3$) δ; 1.99 (dd, 1H, J=5.0, 13.7 Hz), 2.16 (s, 3H), 3.17 (s, 1H), 3.30 (m, 1H), 3.93 (s, 3H), 4.67 (s, 2H), 5.09 (d, 2H, J=3.5 Hz), 7.13 (dd, 1H, J=5.0, 7.3 Hz), 7.25 (dd, 1H, J=5.0, 7.6 Hz), 7.41 (d, 1H, J=16.1 Hz), 7.48 (dd, 1H, J=1.5, 8.7 Hz), 7.60 (d, 1H, J=7.6 Hz), 7.80 (dt, 1H, J=1.6, 7.6 Hz), 7.84 (dd, 1H, J=1.2, 8.7 Hz), 7.85 (d, 1H, J=8.7 Hz), 7.94 (d, 1H, J=8.7 Hz), 7.95 (d, 1H, J=16.1 Hz), 8.29 (d, 1H, J=0.9 Hz), 8.59 (d, 1H, J=4.0 Hz), 8.69 (s, 1H), 9.16 (s, 1H).
FAB-MS (m/z); 601 (M+1)$^+$

Example 113
Synthesis of Compound 114

The same procedure as in Example 99 was repeated using 82 mg (0.12 mmol) of Compound 112 to give 110 mg (72%) of Compound 114.
FAB-MS (m/z); 798 (M+1)$^+$ Example 114
Synthesis of Compound 115

The same procedure as in Example 1, Step B was repeated using 30 mg (0.038 mmol) of Compound 114 to give 12 mg (44%) of Compound 115.

$^1$H-NMR (CDCl$_3$) δ; 0.13 (s, 3H), 0.15 (s, 3H), 0.97 (s, 9H), 2.19 (s, 3H), 2.73 (dd, 1H, J=4.6, 14.4 Hz), 3.48 (dd, 1H, J=7.3, 14.4 Hz), 4.09 (s, 3H), 4.45 (d, 1H, J=16.5 Hz), 4.68 (d, 1H, J=16.5 Hz), 4.74 (d, 1H, J=12.2 Hz), 4.80 (d, 1H, J=12.2 Hz), 5.69 (br, 1H), 6.81 (dd, 1H, J=4.6, 7.3 Hz), 7.08 (d, 1H, J=16.1 Hz), 7.19 (ddd, 1H, J=0.7, 4.9, 7.3 Hz), 7.29 (d, 1H, J=8.5 Hz), 7.38 (d, 1H, J=7.8 Hz), 7.40 (dd, 1H, J=1.4, 8.5 Hz), 7.62 (br, 2H), 7.71 (d, 1H, J=16.1 Hz), 7.80 (s, 1H), 7.84 (d, 1H, J=8.5 Hz), 8.60 (d, 1H, J=3.9 Hz), 8.75 (s, 1H).
FAB-MS (m/s); 715 (M+1)$^+$

Example 115
Synthesis of Compound 116

The same procedure as in Example 1, Step B was repeated using 60 mg (0.10 mmol) of Compound 113 to give 37 mg (40%) of Compound 116.

$^1$H-NMR (CDCl$_3$) δ; 2.20 (s, 3H), 2.65 (d, 1H, J=15.0 Hz), 3.33 (s, 3H), 3.49 (dd, 1H, J=7.4, 15.0 Hz), 4.08 (s, 3H), 4.32–4.66 (m, 4H), 5.86 (s, 1H), 6.85 (dd, 1H, J=4.6, 7.3 Hz), 6.99 (d, 1H, J=16.1 Hz), 7.10 (dd, 1H, J=4.9, 7.4 Hz), 7.36 (br, 2H), 7.39 (dd, 1H, J=0.5, 8.8 Hz),7.60 (br, 4H), 7.72 (s, 1H), 7.80 (d, 1H, J=8.8 Hz), 8.57 (d, 1H, J=3.9 Hz), 8.72 (s, 1H).

FAB-MS (m/s); 615 (M+1)$^+$

Example 116
Synthesis of Compound 117

The same procedure as in Example 102 was repeated using 60 mg (0.10 mmol) of Compound 113 to give 32 mg (51%) of Compound 117.

$^1$H-NMR (CDCl$_3$) δ; 1.26 (t, 3H, J=7.2 Hz), 2.21 (s, 3H), 2.63 (dd, 1H, J=4.6, 14.4 z), 3.34 (dd, 1H, J=7.4, 14.4 Hz), 3.55 (q, 2H, J=7.2 Hz), 4.10 (s, 3H), 4.50 (d, 1H, J=11.5 Hz), 4.57 (d, 1H, J=16.6 Hz), 4.58 (d, 1H, J=11.5 Hz), 4.77 (d, 1H, J=16.6 Hz), 5.81 (s, 1H), 6.86 (dd, 1H, J=4.6, 7.5 Hz), 7.15 (br, 2H), 7.36 (d, 1H, J=8.6 Hz), 7.40 (d, 1H, J=7.8 Hz), 7.45 (dd, 1H, J=1.7, 8.6 Hz), 7.64 (br, 3H), 7.74 (d, 1H, J=16.1 Hz), 7.84 (d, 1H, J=8.5 Hz), 7.87 (s, 1H), 8.61 (d, 1H, J=3.6 Hz), 8.86 (s, 1H).

FAB-MS (m/s); 629 (M+1)$^+$

Example 117
Synthesis of Compound 118

The same procedure as in Example 104 was repeated using 60 mg (0.10 mmol) of Compound 113 to give 30 mg (46%) of Compound 118.

$^1$H-NMR (CDCl$_3$) δ; 1.24 (t, 3H, J=7.3 Hz), 2.22 (s, 3H), 2.45 (q, 2H, J=7.3 Hz), 2.62 (dd, 1H, J=4.6, 14.5 z), 3.50 (dd, 1H, J=7.3, 14.5 Hz), 3.71 (d, 1H, J=14.9 Hz), 3.77 (d, 1H, J=14.9 Hz), 4.10 (s, 3H), 4.46 (d, 1H, J=16.6 Hz),4.71 (d, 1H, J=16.6 Hz), 5.80 (s, 1H), 6.87 (dd, 1H, J=4.6, 7.3 Hz), 7.04 (d, 1H, J=16.7 Hz), 7.12 (ddd, 1H, J=0.7, 5.2, 7.6 Hz), 7.37 (br, 2H), 7.43 (dd, 1H, J=1.7, 8.6 Hz), 7.62 (br, 3H) 7.78 (s, 1H), 7.81 (d, 1H, J=8.6 Hz), 8.59 (d, 1H, J=3.9 Hz), 8.75 (s, 1H).

FAB-MS (m/s); 645 (M+1)$^+$

Example 118
Synthesis of Compound 119

The same procedure as in Example 106 was repeated using 60 mg (0.10 mmol) of Compound 113 to give 28 mg (40%) of Compound 119.

$^1$H-NMR (CDCl$_3$) δ; 2.00 (dd, 1H, J=4.9, 13.9 Hz), 2.16 (s, 3H), 3.32 (br, 1H), 3.93 (s, 3H), 4.62 (s, 2H), 5.10 (s, 2H), 6.40 (s, 1H), 7.12 (br, 2H), 7.26 (br, 1H), 7.34 (d, 1H, J=7.9 Hz), 7.41 (d, 1H, J=16.1 Hz), 7.54 (dd, 1H, J=2.0, 8.6 Hz), 7.65 (br, 2H), 7.81 (br, 3H), 7.94 (s, 1H), 7.97 (d, 1H, J=6.9 Hz), 8.29 (s, 1H), 8.60 (s, 1H), 8.65 (d, 1H, J=7.1 Hz),8.70 (s, 1H), 9.28 (s, 1H).

FAB-MS (m/s); 694 (M+1)$^+$

Example 119
Synthesis of Compound 120

To a solution of 90 mg (0.15 mmol) of Compound 113 in 3.0 ml of methylene chloride was added 225 mg (1.0 mmol) of 2-mercaptobenzimidazole and 695 mg (3.0 mmol) of camphorsulfonic acid, followed by reflux for 1 day. The reaction mixture was poured into a saturated aqueous solution of sodium hydrogencarbonate, followed by extraction with chloroform/methanol (9/1). The extract was washed with a saturated aqueous solution of sodium chloride, and dried over sodium sulfate. The solvent was evaporated under reduced pressure to give 26 mg (24%) of Compound 120.

$^1$H-NMR (DMSO-d$_6$) δ; 2.00 (dd, 1H, J=4.8, 13.9 Hz), 2.16 (s, 3H), 3.92 (m, 1H), 3.93 (s, 3H), 4.79 (s, 2H), 5.10 (s, 2H), 6.40 (s, 1H), 7.13 (br, 5H), 7.26 (dd, 1H, J=5.4, 6.9 Hz), 7.41 (d, 1H, J=16.1 Hz), 7.59 (br, 3H), 7.84 (br, 3H), 7.94 (d, 1H, J=8.9 Hz), 7.95 (d, 1H, J=16.1 Hz), 8.29 (s, 1H), 8.59 (d, 1H, J=4.0 Hz), 8.71 (s, 1H), 9.30 (d, 1H, J=1.4 Hz), 12.6 (br, 1H).

FAB-MS (m/s); 733 (M+1)$^+$

Example 120
Synthesis of Compound 121

The same procedure as in Example 96 was repeated using 146 mg (0.20 mmol) of Compound 67 to give 57 mg (mixture of E and Z, 40%) of Compound 121.

FAB-MS (m/s); 709 (M+1)$^+$

Example 121
Synthesis of Compound 122

The same procedure as in Example 1, Step B was repeated using 57 mg (0.080 mmol) of Compound 121 to give 32 mg (64%) of Compound 122.

FAB-MS (m/s); 625 (M+1)$^+$

Example 122
Synthesis of Compound 123

The same procedure as in Example 62 was repeated using 68 mg (0.1 mmol) of Compound 100 to give 34 mg (50%) of Compound 123.

FAB-MS (m/z); 802 (M+1)$^+$

Example 123
Synthesis of Compound 124

The same procedure as in Example 1, Step B was repeated using 40 mg (0.050 mmol) of Compound 123 to give 11 mg (31%) of Compound 124.

$^1$H-NMR (CDCl$_3$) δ; 0.19 (s, 6H), 1.02 (s, 9H), 2.19 (s, 3H), 2.51 (dd, 1H, J=4.9, 14.4 Hz), 3.23 (br, 4H), 3.34 (dd, 1H, J=7.3, 14.4 Hz), 4.08 (s, 3H), 4.38 (br, 1H), 4.80 (d, 1H, J=16.4 Hz), 4.88 (d, 1H, J=16.4 Hz), 4.96 (s, 2H), 5.89 (br, 1H), 6.83 (dd, 1H, J=4.9, 7.3 Hz), 7.11 (ddd, 1H, J=1.0, 4.9, 7.3 Hz), 7.16 (d, 1H, J=7.6 Hz), 7.28 (br, 2H), 7.42 (dd, 1H, J=1.7, 8.8 Hz), 7.56 (dt, 1H, J=2.0, 7.6 Hz), 7.80 (d, 1H, J=8.8 Hz), 7.87 (d, 1H, J=1.0 Hz), 8.58 (ddd, 1H, J=0.73, 1.7, 3.9 Hz), 9.02 (s, 1H).

FAB-MS (m/z); 716 (M+1)$^+$

Example 124
Synthesis of Compounds 125a and 125b

To a solution of 80 mg (0.1 mmol) of Compound 123 in 6 ml of chloroform/methanol (5/1) was added 104 mg (0.45 mmol) of camphorsulfonic acid, followed by stirring at 40_C. for 1 day. The reaction sure was poured into a saturated aqueous solution of sodium hydrogencarbonate, followed by extraction with chloroform/methanol. The extract was washed with a saturated aqueous solution of sodium chloride, and dried over sodium sulfate. After the solvent was evaporated under reduced pressure, the residue was purified by silica gel column chromatography (chloroform/methanol=20/1) to give 12 mg (17%) of Compound 125a and 38 mg (58%) of Compound 125b.

Compound 125a

FAB-MS (m/s); 701 (M+1)$^+$

Compound 125b

FAB-MS (m/z); 659 (M+1)$^+$

Example 125
Synthesis of Compound 126

The same procedure as in Example 1, Step B was repeated using 38 mg (0.057 mmol) of Compound 125b to give 21 mg (60%) of Compound 126.

$^1$H-NMR (CDCl$_3$) δ; 2.14 (s, 3H), 2.49 (dd, 1H, J=4.9, 14.4 Hz), 3.19 (br, 4H), 3.34 (dd, 1H, J=7.3, 14.4 Hz), 3.50 (s, 3H), 4.07 (s, 3H), 4.64 (d, 1H, J=16.7 hz), 4.65 (s, 2H), 4.75 (d, 1H, J=16.6 Hz), 6.04 (br, 1H), 6.82 (dd, 1H, J=4.6, 7.3 Hz), 7.10 (dd, 1H, J=4.6, 7.3 Hz), 7.14 (d, 1H, J=7.6 Hz), 7.22 (dd, 1H, J=1.7, 8.5 Hz), 7.28 (d, 1H, J=8.5 Hz), 7.42 (dd, 1H, J=1.5, 8.8 Hz), 7.56 (dt, 1H, J=1.7, 7.6 Hz), 7.79 (s, 1H), 7.82 (d, 1H, J=8.8 Hz), 8.57 (d, 1H, J=4.8 Hz), 8.93 (d, 1H, J=1.0 Hz).

FAB-MS (m/z); 617 (M+1)$^+$

Example 126
Synthesis of Compounds 127a and 127b

The same procedure as in Example 102 was repeated using 80 mg (0.1 mmol) of Compound 123 to give diacetylated Compounds 127a and 127b. The same procedure as in Example 1, Step B was repeated using diacetylated Compounds 127a and 127b to give 14.6 mg (23%) of Compound 127a and 11.0 mg (18%) of Compound 127b.

Compound 127a $^1$H-NMR (CDCl$_3$) δ; 1.33 (t, 3H, J=7.1 Hz), 2.12 (s, 3H), 2.58 (dd, 1H, J=4.8, 14.4 Hz), 3.17 (br, 4H), 3.37 (dd, 1H, J=7.3, 14.4 Hz), 3.65 (q, 2H, J=7.1 Hz), 4.05 (s, 3H), 4.58 (d, 1H, J=16.6 Hz), 4.67 (d, 1H, J=16.6 Hz), 4.69 (s, 2H), 5.9 (s, 1H), 6.80 (dd, 1H, J=4.8, 7.3 Hz), 7.11 (ddd, 1H, J=1.0, 4.9, 7.6 Hz), 7.15 (d, 1H, J=7.6 Hz), 7.17 (dd, 1H, J=1.8, 8.6 Hz), 7.23 (d, 1H, J=8.5 Hz), 7.43 (dd, 1H, J=1.5, 8.5 Hz), 7.56 (dt, 1H, J=1.8, 7.6 Hz), 7.78 (s, 1H), 7.83 (d, 1H, J=8.5 Hz), 8.57 (br, 1H), 8.83 (d, 1H, J=1.0 Hz).

FAB-MS (m/z); 631 (M+1)$^+$

Compound 127b $^1$H-NMR (CDCl$_3$) δ; 1.98 (dd, 1H, J=4.9, 14.4 Hz), 2.14 (s, 3H), 3.29 (br, 4H), 3.36 (dd, 1H, J=7.3, 14.4 Hz), 3.92 (s, 3H), 4.71 (d, 2H, J=5.7 Hz), 4.98 (d, 2H, J=4.9 Hz), 5.21 (t, 1H, J=5.7 Hz), 6.30 (s, 1H), 7.08 (dd, 1H, J=4.9, 7.3 Hz), 7.21 (ddd, 1H, J=1.0, 4.9, 7.3 Hz), 7.32 (d, 1H, J=7.6 Hz), 7.35 (dd, 1H, J=1.7, 8.6 Hz), 7.44 (dd, 1H, J=1.4, 8.6 Hz), 7.69 (dt, 1H, J=1.7, 7.6 Hz), 7.78 (d, 1H, J=8.6 Hz), 7.88 (d, 1H, J=8.6 Hz), 7.96 (s, 1H), 8.53 (ddd, 1H, J=0.7, 1.7, 4.5 Hz), 8.59 (s, 1H), 9.10 (d, 1H, J=1.4 Hz).

FAB-MS (m/z); 603 (M+1)$^+$

Example 127
Synthesis of Compound 128

The same procedure as in Example 106 was repeated using 80 mg (0.1 mmol) of Compound 123 to give 42 mg (54%) of Compound 128.

FAB-MS (m/z); 780 (M+1)$^+$

Example 128
Synthesis of Compound 129

The same procedure as in Example 1, Step B was repeated using 42 mg (0.057 mmol) of Compound 128 to give 13 mg (33%) of Compound 129.

$^1$H-NMR (CDCl$_3$) δ; 2.14 (s, 3H), 2.66 (dd, 1H, J=4.9, 14.4. Hz), 3.18 (br, 4H), 3.39 (dd, 1H, J=7.6, 14.4 Hz), 4.06 (s, 3H), 4.58 (s, 2H), 4.63 (d, 1H, J=13.4 Hz), 4.70 (d, 1H, J=13.4 Hz), 5.71 (br, 1H), 6.77 (dd, 1H, J=4.9, 7.6 Hz), 7.02 (ddd, 1H, J=1.1, 1.2, 7.3 Hz), 7.12 (ddd, 1H, J=1.2, 4.9, 7.6. Hz), 7.15 (d, 1H, J=8.8 Hz), 7.22 (d, 2H, J=7.3 Hz), 7.55 (br, 4H), 7.81 (d, 1H, J=8.8 Hz), 7.92 (d, 1H, J=1.5 Hz), 8.52 (ddd, 1H, J=1.0, 1.7, 4.9 Hz), 8.59 (ddd, 1H, J=1.0, 1.9, 4.9 Hz),8.78 (s, 1H).

FAB-MS (m/z); 679 (M+1)$^+$

Example 129
Synthesis of Compound 130

The same procedure as in Example 62 was repeated using 600 mg (0.057 mmol) of Compound 114 to give 423 mg (71%) of Compound 130.

FAB-MS (m/z); 801 (M+1)$^+$

Example 130
Synthesis of Compound 131

The same procedure as in Example 1, Step B was repeated using 30 mg (0.037 mmol) of Compound 130 to give 9.0 mg (34%) of Compound 131.

$^1$H-NMR (CDCl$_3$) δ; 0.17 (s, 3H), 0.18 (s, 3H), 1.00 (s, 9H), 2.15 (s, 3H), 2.70 (dd, 1H, J=4.9, 14.3 Hz), 3.26–3.36 (m, 4H), 3.39 (dd, 1H, J=7.3, 14.3 Hz), 4.08 (s, 3H), 4.67 (d, 1H, J=16.4 Hz), 4.73 (d, 1H, J=16.4 Hz), 4.92 (s, 2H), 5.70 (br, 2H), 5.70 (br, 1H), 6.79 (dd, 1H, J=4.9, 7.3 Hz), 7.16 (ddd, 1H, J=1.2, 4.9, 7.1 Hz), 7.20 (dt, 1H, J=1.0, 7.6 Hz), 7.28 (br, 2H), 7.41 (dd, 1H, J=1.7, 8.5 Hz), 7.62 (dt, 1H, J=1.9, 7.6 Hz), 7.68 (d, 1H, J=1.5 Hz), 7.78 (d, 1H, J=8.5 Hz), 8.60 (ddd, 1H, J=1.0, 2.0, 4.8 Hz), 8.90 (s, 1H).

FAB-MS (m/z); 717 (M+1)$^+$

Example 131
Synthesis of Compounds 132

The same procedure as in Example 101 was repeated using 80 mg (0.1 mmol) of Compound 130 to give diacetylated Compound 132. The same procedure as in Example 1, Step B was repeated using diacetylated Compound 132 to give 36.5 mg (59%) of Compound 132.

$^1$H-NMR (CDCl$_3$) δ; 2.12 (s, 3H), 2.86 (dd, 1H, J=4.9, 14.4 Hz), 3.28–3.45 (m, 4H), 3.43 (s, 3H), 3.47 (dd, 1H, J=7.3, 14.4 Hz), 4.06 (s, 3H), 4.43–4.59 (m, 4H), 5.70 (br, 1H), 5.75 (br, 1H), 6.73 (dd, 1H, J=4.9, 7.3 Hz), 7.15 (ddd, 1H, J=1.2, 4.9, 7.3 Hz), 7.17 (d, 1H, J=8.5 Hz), 7.20 (d, 1H, J=7.6 Hz), 7.21 (dd, 1H, J=1.7, 8.5 Hz), 7.60 (d, 1H, J=1.7 Hz), 7.61 (dt, 1H, J=1.7, 7.6 Hz), 7.82 (d, 1H, J=8.5 Hz), 8.56 (ddd, 1H, J=1.0, 1.7, 4.9 Hz), 8.72 (d, 1H, J=1.2 Hz).

FAB-MS (m/z); 617 (M+1)$^+$

Example 132
Synthesis of Compounds 133

The same procedure as in Example 102 was repeated using 80 mg (0.1 mmol) of Compound 130 to give diacetylated Compound 133. The same procedure as in Example 1, Step B was repeated using diacetylated Compound 133 to give 4.9 mg (7.8%) of Compound 133.

$^1$H-NMR (CDCl$_3$) δ; 1.31 (t, 3H, J=7.0 Hz), 2.13 (s, 3H), 2.78 (dd, 1H, J=5.1, 14.6 Hz), 3.48 (br, 4H), 3.71 (q, 2H, J=7.0 Hz), 4.07 (s, 3H), 4.55–5.13 (m, 4H), 5.71 (br, 1H), 5.75 (br, 1H), 6.76 (dd, 1H, J=5.1, 7.3 Hz), 7.15 (ddd, 1H, J=1.0, 4.9, 7.3 Hz), 7.22 (br, 3H), 7.36 (dd, 1H, J=1.7, 8.8 Hz), 7.61 (dd, 1H, J=1.7, 7.8 Hz), 7.64 (d, 1H, J=0.8 Hz), 7.80 (d, 1H, J=8.8 Hz), 8.57 (ddd, 1H, J=0.9, 1.9, 4.9 Hz), 8.83 (d, 1H, J=1.0 Hz).

FAB-MS (m/z); 631 (M+1)$^+$

Example 133
Synthesis of Compounds 134

The same procedure as in Example 104 was repeated using 80 mg (0.1 mmol) of Compound 130 to give diacetylated Compound 134. The same procedure as in Example 1, Step B was repeated using diacetylated Compound 134 to give 16 mg (23%) of Compound 134.

$^1$H-NMR (CDCl$_3$) δ; 1.30 (t, 3H, J=7.3 Hz), 2.14 (s,3H), 2.54 (q, 2H, J=7.3 Hz), 2.78 (dd, 1H, J=4.9, 14.4 Hz), 3.18–3.34 (m, 4H), 3.52 (dd, 1H, J=7.3, 14.4 Hz), 3.88 (s, 3H), 4.08 (s, 3H), 4.53 (d, 1H, J=16.6 Hz), 4.63 (d, 1H, J=16.6 Hz),5.68 (s, 1H), 6.78 (dd, 1H, J=4.9, 7.3 Hz), 7.15 (ddd, 1H, J=1.0, 4.8, 7.8 Hz), 7.22 (br,3H), 7.36 (dd, 1H, J=1.7, 8.5 Hz), 7.61 (dd,1H, J=1.7, 7.8 Hz), 7.63 (s, 1H), 7.80 (d, 1H, J=8.5 Hz), 8.58 (ddd, 1H, J=0.9, 1.7, 4.9 Hz), 8.76 (d, 1H, J=1.2 Hz).

FAB-MS (m/z); 647 (M+1)$^+$

Example 134
Synthesis of Compound 135

The same procedure as in Example 105 was repeated using 80 mg (0.10 mmol) of Compound 130 to give 16 mg (23%) of Compound 135.

$^1$H-NMR (CDCl$_3$) δ; 1.99 (dd, 1H, J=4.9, 14.1 Hz), 2.12 (s, 3H), 2.13 (s, 6H), 2.50 (br, 4H), 3.20 (br, 4H), 3.34 (dd, 1H, J=7.1, 14.1 Hz), 3.92 (s, 3H), 3.95 (s, 2H), 4.91 (d, 1H, J=17.5 Hz), 4.98 (d, 1H, J=17.5 Hz), 6.29 (s, 1H), 7.09 (dd, 1H, J=4.9, 7.1 Hz), 7.23 (ddd, 1H, J=0.7, 4.9, 7.5 Hz), 7.33 (br, 2H), 7.44 (dd, 1H, J=1.5, 8.4 Hz), 7.71 (dt, 1H, J=1.9, 7.6 Hz), 7.82–7.85 (m, 2H), 8.55 (ddd, 1H, J=0.7, 1.0, 4.9 Hz), 8.60 (s, 1H), 9.13 (d, 1H, J=1.7 Hz).

FAB-MS (m/z); 690 (M+1)$^+$

Example 135
Synthesis of Compound 136

The same procedure as in Example 106 was repeated using 80 mg (0.1 mmol) of Compound 130 to give 45 mg (58%) of Compound 136.

FAB-MS (m/z); 780 (M+1)$^+$

Example 136
Synthesis of Compound 137

The same procedure as in Example 1, Step B was repeated using 45 mg (0.058 mmol) of Compound 136 to give 24 mg (59%) of Compound 137.

$^1$H-NMR (CDCl$_3$) δ; 2.14 (s, 3H), 3.23 (dd, 1H, J=4.9, 14.4 Hz), 3.22–3.34 (m, 4H), 3.51 (dd, 1H, J=7.6, 14.4 Hz), 4.04 (s, 3H), 4.55–4.68 (m, 4H), 5.59 (br, 1H), 6.77 (dd, 1H, J=4.9, 7.6 Hz), 7.01 (ddd, 1H, J=1.0, 4.9, 7.6 Hz), 7.16 (ddd, 1H, J=1.0, 2.4, 7.6 Hz), 7.23 (br, 4H), 7.34 (dd, 1H, J=1.5, 8.6 Hz), 7.50 (ddd, 1H, J=1.9, 7.6, 7.9 Hz), 7.62 (dt, 1H, J=1.8, 7.6 Hz), 7.67 (d, 1H, J=1.2 Hz), 7.79 (d, 1H, J=8.6 Hz), 8.53 (ddd, 1H, J=0.7, 1.7, 4.7 Hz), 8.59 (ddd, 1H, J=0.7, 1.7, 4.9 Hz), 8.93 (s, 1H).

FAB-MS (m/z); 696 (M+1)$^+$

Example 137
Synthesis of Compound 138

To a solution of 290 mg (0.40 mmol) of Compound G in 3 ml of methanol/methylene chloride (1/1) was added 4.5 mg (0.12 mmol) of sodium borohydride, followed by stirring at room temperature for 1 hour. The reaction mixture was poured into ice-cold water, followed by extraction with chloroform/methanol. The extra was washed with a saturated aqueous solution of sodium chloride, and dried over sodium sulfate. After the solvent was evaporated under reduced pressure, the residue was purified by silica gel column chromatography (chloroform) to give 120 mg (75%) of a hydroxymethyl compound.

The same procedure as in Example 21 was repeated using 210 mg (0.29 mmol) of the obtained hydroxymethyl compound to give 60 mg (39%) of Compound 138.

$^1$H-NMR (DMSO-d$_6$) δ; 1.95 (br, 2H), 2.15 (s, 3H), 3.20 (br, 2H), 3.80 (br, 3H), 4.39 (s, 4H), 5.05 (d, 1H, J=7.8 Hz), 5.15 (t, 1H, J=6.03 Hz), 5.46 (s, 1H), 6.98 (m, 1H), 7.53 (dd, 1H, J=1.7, 8.6 Hz), 7.55 (dd, 1H, J=1.7, 8.8 Hz), 7.82 (d, 1H, J=8.6 Hz), 7.96 (d, 1H, J=8.8 Hz), 8.13 (d, 1H, J=1.2 Hz), 8.70 (br, 1H), 9.33 (d, 1H, J=1.5 Hz).

FAB-MS (m/s); 576 (M+1)$^+$

Example 138
Synthesis of Compound 139

The same procedure as in Example 9 was repeated using 48.2 mg (0.0630 mmol) of Compound 1 to give 29.0 mg (60%) of Compound 139.

$^1$H-NMR (DMSO-d$_6$) δ; 1.96 (dd, 1H, J=4.9, 13.9 Hz), 2.12 (s, 3H), 2.70–2.79 (m, 4H), 3.04–3.10 (m, 4H), 3.35 (dd, 1H, J=7.3, 13.9 Hz), 3.62 (s, 3H), 3.63 (s, 3H), 3.91 (s, 3H), 4.96 (d, 1H, J=17.6 Hz), 5.01 (d, 1H, J=17.6 Hz), 6.28 (s, 1H), 7.08 (dd, 1H, J=4.9, 7.3 Hz), 7.33–7.37 (m, 2H), 7.80 (d, 1H, J=8.5 Hz), 7.83 (d, 1H, J=8.6 Hz), 7.88 (m, 1H), 8.60 (br, 1H), 9.04 (m, 1H).

FAB-MS (m/z); 640 (M+1)$^+$

Example 139
Synthesis of Compound 140

The same procedure as in Example 9 was repeated using 41.8 mg (0.0962 mmol) of Compound 3 to give 27.0 mg (64%) of Compound 140.

$^1$H-NMR (DMSO-d$_6$) δ; 1.19 (t, 3H, J=7.1 Hz), 1.20 (t, 3H, J=7.1 Hz), 1.96 (dd, 1H, J=4.9, 13.9 Hz), 2.12 (s, 3H), 2.68–2.77 (m, 4H), 3.03–3.09 (m, 4H), 3.35 (dd, 1H, J=7.2, 13.9 Hz), 3.91 (s, 3H), 4.08 (q, 2H, J=7.1 Hz), 4.09 (q, 2H, J=0.1 Hz), 4.96 (d, 1H, J=17.7 Hz), 5.01 (d, 1H, J=17.7 Hz), 6.28 (s, 1H), 7.08 (dd, 1H, J=4.9, 7.2 Hz), 7.33–7.37 (m, 2H), 7.79 (d, 1H, J=8.6 Hz), 7.83 (d, 1H, J=8.5 Hz), 7.88 (d, 1H, J=1.5 Hz), 8.60 (br, 1H), 9.04 (d, 1H, J=1.0 Hz).

FAB-MS (m/z); 668 (M+1)$^+$

Example 140
Synthesis of Compound 141

The same procedure as in Example 5 was repeated using 3 mg (0.536 mmol) of 2-pyridylmethyltriphenylphosphonium bromide and 82.8 mg (0.126 mmol) of Compound B to give 62.0 mg (E/Z=9/1, 67%) of Compound 141.

FAB-MS (m/z); 733 (M+1)$^+$, 735 (M+1)$^+$

Example 141
Synthesis of Compound 142

The same procedure as in Example 1, Step B was repeated using 62.0 mg (0.0846 mmol) of Compound 141 to give 36.6 mg (E/Z=9/1, 67%) of Compound 142.

FAB-MS (m/z); 649 (M+1)$^+$, 651 (M+1)$^+$

Example 142
Synthesis of Compound 143

To a solution of 28.1 mg (0.0433 mmol) of Compound 142 in 0.5 ml of N,N-dimethylformamide was added 2.6 mg of platinum oxide, followed by stirring in a hydrogen atmosphere at room temperature for 2 days. Insoluble materials in the reaction mixture were removed by filtration, and the filtrate was evaporated under reduced pressure. The residue was purified by silica gel column chromatography (chloroform/methanol=95/5) to give 10.6 mg (38%) of Compound 143.

$^1$H-NMR (DMSO-d$_6$) δ; 2.00 (dd, 1H, J=4.9, 14.2 Hz), 2.12 (s, 3H), 3.16–3.26 (m, 4H), 3.38 (dd, 1H, J=7.3, 14.2 Hz), 3.91 (s, 3H), 4.94 (d, 1H, J=18.2 Hz), 5.00 (d, 1H, J=18.2 Hz), 6.31 (s, 1H), 7.14 (dd, 1H, J=4.9, 7.3 Hz), 7.23 (m, 1H), 7.34 (d, 1H, J=7.8 Hz), 7.39 (m, 1H), 7.60 (m, 1H), 7.71 (m, 1H), 7.83–7.85 (m, 2H), 7.92 (d, 1H, J=8.8 Hz), 8.55 (m, 1H), 8.72 (s, 1H), 9.38 (d, 1H, J=2.0 Hz).

FAB-MS (m/z); 651 (M+1)$^+$, 653 (M+1)$^+$

Example 143
Synthesis of Compound 144

The same procedure as in Example 5 was repeated using 547 mg (18.2 mmol) of 4-pyridylmethyltriphenylphosphonium chloride and 104 mg (0.171 mmol) of Compound a to give 42.2 mg (33%) of Compound 144.

FAB-MS (m/z); 758 (M+1)$^+$

Example 144
Synthesis of Compound 145

The same procedure as in Example 1, Step B was repeated using 40.0 mg (0.0528 mmol) of Compound 144 to give 16.1 mg (45%) of Compound 145.

$^1$H-NMR (DMSO-d$_6$) δ; 2.06 (dd, 1H, J=5.0, 14.3 Hz), 2.17 (s, 3H), 3.44 (dd, 1H, J=7.5, 14.2 Hz), 3.95 (s, 3H), 5.09 (d, 1H, J=17.2 Hz), 5.14 (d, 1H, J=17.2 Hz), 6.44 (s, 1H), 7.20 (dd, 1H, J=5.0, 7.5 Hz), 7.23 (d, 1H, J=16.3 Hz), 7.36 (d, 1H, J=16.3 Hz), 7.62–7.65 (m, 4H), 7.75 (d, 1H, J=16.3 Hz), 7.82 (d, 1H, J=16.3 Hz), 7.85 (m, 1 H), 7.91 (m, 1H), 7.97–8.00 (m, 2H), 8.31 (d, 1H, J=1.4 Hz), 8.54–8.58 (m, 4H), 8.77 (s, 1H), 9.45 (d, 1H, J=1.6 Hz).

FAB-MS (m/z); 674 (M+1)$^+$

Example 145
Synthesis of Compound 146

The same procedure as in Example 9 was repeated using 21.3 mg (0.0316 mmol) of Compound 145 to give 6.7 mg (31%) of Compound 146.

$^1$H-NMR (DMSO-d$_6$) δ; 1.97 (dd, 1H, J=4.9, 14.1 Hz), 2.12 (s, 3H), 3.02–3.16 (m, 8H), 3.35 (dd, 1H, J=7.3, 14.1 Hz), 3.91 (s, 3H), 4.93 (d, 1H, J=17.6 Hz), 4.97 (d, 1H, J=17.6 Hz), 6.30 (s, 1H), 7.08 (dd, 1H, J=4.9, 7.3 Hz), 7.33–7.38 (m, 6H), 7.79–7.84 (m, 2H), 7.85 (m, 1H), 8.45–7.48 (m, 4H), 8.61 (m, 1H), 9.08 (m, 1H).

FAB-MS (m/z); 678 (M+1)$^+$

Example 146
Synthesis of Compound 147

To a methylene chloride (1 ml) solution of 70.0 mg (0.0824 mmol) of the coarse phosphonium salt, which was obtained by repeating the same method as in Example 64 using 51.3 mg (0.0883 mmol) of Compound e and 44.1 mg (0.128 mmol) of triphenylphosphine hydrobromide, were added 11.6 mg (0.0839 mmol) of potassium carbonate and 0.9 mg (0.0034 mmol) of 18-crown-6, followed by stirring at room temperature for 5 minutes. To the mixture was added 10.2 mg (0.106 mmol) of 2-imidazolecarboxaldehyde, followed by stirring at room temperature for 4 days. After insoluble materials in the reaction mixture were removed by filtration, the filtrate was evaporated under reduced pressure. The residue was purified by silica gel column chromatography (chloroform/methanol=95/5) to give 34.2 mg (69%) of Compound 147.

FAB-MS (m/z); 644 (M+1)$^+$

Example 147
Synthesis of Compound 148

The same procedure as in Example 1, Step B was repeated using 34.2 mg (0.0532 mmol) of Compound 147 to give 22.3 mg (E/Z=1/3, 75%) of Compound 148.

FAB-MS (m/z); 560(M+1)$^+$

Example 148
Synthesis of Compound 149

The same procedure as in Example 9 was repeated using 10.1 mg (0.0181 mmol) of Compound 148 to give 6.9 mg (69%) of Compound 149.

$^1$H-NMR (DMSO-d$_6$) δ; 1.99 (dd, 1H, J=4.9, 14.1 Hz), 2.15 (s, 3H), 3.04–3.07 (m, 2H), 3.15–3.19 (m, 2H), 3.37 (dd, 1H, J=7.4, 14.1 Hz), 3.92 (s, 3H), 4.98 (d, 1H, J=17.2 Hz), 5.03 (d, 1H, J=17.2 Hz), 6.33 (s, 1H), 7.02 (br, 2H), 7.10 (dd, 1H, J=4.9, 7.4 Hz), 7.32 (m, 1H), 7.36 (m, 1H), 7.48 (m, 1H), 7.81 (m, 1H), 7.94 (m, 1H), 8.05 (m, 1H), 8.61 (s, 1H), 9.09 (d, 1H, J=1.0 Hz).

FAB-MS (m/z); 562 (M+1)$^+$

Example 149
Synthesis of Compound 150

To a solution of 75.4 mg (0.124 mmol) of Compound a in 3 ml of chloroform were added 0.15 ml (1.31 mmol) of dimethyl malonate and 0.015 ml of piperidine, followed by stirring under reflux for 12 hours. After cooling, the reaction mixture was poured into 4N hydrochloric acid, followed by extraction with chloroform. The organic layer was washed with a saturated aqueous solution of sodium chloride, and dried over sodium sulfate. After the solvent was evaporated under reduced pressure, the residue was purified by trituration with methanol to give 88.9 mg (86%) of Compound 150.

$^1$H-NMR (CDCl$_3$) δ; 1.80 (s, 3H), 2.14 (dd, 1H, J=5.1, 14.6 Hz), 2.28 (s, 3H), 2.81 (s, 3H), 3.89 (s, 3H), 3.92 (s, 3H), 3.99 (dd, 1H, J=7.5, 14.6 Hz), 4.01 (s, 3H), 4.03 (s, 3H), 4.09 (s, 3H), 5.36 (s, 2H), 7.00 (dd, 1H, J=5.1, 7.5 Hz), 7.53 (d, 1H, J=9.3 Hz), 7.61–7.65 (m, 2H), 7.92 (d, 1H, J=8.8 Hz), 7.98 (s, 1H), 8.04 (s, 1H), 8.18 (d, 1H, J=1.7 Hz), 9.37 (d, 1H, J=1.7 Hz).

FAB-MS (m/z); 836(M+1)$^+$

Example 150
Synthesis of Compound 151

The same procedure as in Example 9 was repeated using 81.7 mg (0.0978 mmol) of Compound 150 to give 65.9 mg (80%) of Compound 151.

FAB-MS (m/z); 840(M+1)$^+$

Example 151
Synthesis of Compound 152

To a mixed solution of 56.5 mg (0.0673 mmol) of Compound 151 in methylene chloride (3 ml)/methanol (0.6 ml) was added 32.8 mg of potassium carbonate, followed by stirring at room temperature for 6 hours. The reaction mixture was poured into water, followed by extraction with chloroform. The organic layer was washed with a stature aqueous solution of sodium chloride, and dried over sodium sulfate. The solvent was evaporated under reduced pressure to give 33.4 mg (66%) of Compound 152.

$^1$H-NMR (CDCl$_3$) δ; 2.14 (s, 3H), 2.80 (dd, 1H, J=4.8, 14.4 Hz), 3.37 (d, 2H, J=7.8 Hz), 3.41–3.47 (m, 2H), 3.53 (dd, 1H, J=6.8, 14.2 Hz), 3.73 (s, 3H), 3.75 (s, 3H), 3.75 (m, 1H), 3.78 (s, 3H), 3.79 (s, 3H), 3.95 (m, 3H), 4.09 (s, 3H), 4.67 (d, 1H, J=16.6 Hz), 4.73 (d, 1H, J=16.6 Hz), 5.11 (br, 1H), 5.42 (s, 1H), 6.77 (dd, 1H, J=4.8, 7.6 Hz), 7.14 (m, 1H), 7.18 (d, 1H, J=8.3 Hz), 7.29 (m, 1H), 7.82 (d, 1H, J=8.8 Hz), 7.88 (d, 1H, J=1.5 Hz), 8.69 (m, 1H).

FAB-MS (m/z); 756 (M+1)$^+$

Example 152
Synthesis of Compound 153

To a solution of 10 mg (0.016 mmol) of Compound 122 in 3 ml of methanol was added 10 mg of 10% Pd/C, followed by reflux in a hydrogen atmosphere for a day. Insoluble materials were removed by filtration, and the filtrate was evaporated under reduced pressure. The residue was purified by silica gel column chromatography (chloroform) to give 2.7 mg (27%) of Compound 153.

1HNMR (CDCl$_3$) δ; 0.97 (t, 3H, J=7.3 Hz), 1.40–1.47 (m, 2H), 1.67–1.78 (m, 2H), 2.19 (s, 3H), 2.35 (dd, 1H, J=4.7, 14.5 Hz), 2.83 (t, 2H, J=7.8 Hz), 3.23–3.31 (m, 5H), 4.08 (s, 3H), 4.88 (d, 2H, J=1.7 Hz), 5.98 (br, 1H), 6.84 (dd, 1H, J=4.7, 7.3 Hz), 7.16 (d, 1H, J=7.7 Hz), 7.26–7.36 (m, 4H), 7.60 (ddd, 1H, J=2.0, 5.9, 7.7 Hz), 7.68–7.73 (m, 3H), 8.61 (d, 1H, J=4.0 Hz), 9.04 (br s, 1H).

FAB-MS (m/z); 629 (M+1)+

Example 153
Synthesis of Compound 154

To a solution of 67.9 mg (0.117 mmol) of Compound e in 3 ml of dichloromethane was added 0.02 ml (0.26 mmol) of chloromethyl methyl ether and 0.02 ml (0.12 mmol) of N,N-diisopropylethylamine, and the mixture was stirred at room temperature for 8 hours. After addition of 1N aqueous solution of sodium hydroxide, the reaction mixture was extracted with chloroform. The organic layer was washed with a saturated aqueous solution of sodium chloride and dried over sodium sulfate. The solvent was evaporated under reduced pressure, and the residue was triturated with methanol to give 53.8 mg (74%) of diacetylated Compound 154.

1H-NMR(CDCl$_3$) δ; 1.80 (s, 3H), 2.16 (dd, 1H, J=5.0, 14.6 Hz), 2.28 (s, 3H), 2.86 (s, 3H), 3.49 (s, 3H), 3.99 (dd, 1H, J=7.5, 14.6 Hz), 4.01 (s, 3H), 4.80 (s, 2H), 4.86 (s, 2H), 5.41 (d, 1H, J=17.6 Hz), 5.46 (d, 1H, J=17.6 Hz), 7.02 (dd, 1H, J=5.0, 7.5 Hz), 7.44 (m, 1H), 7.54 (m, 2H), 7.61 (m, 1H) 7.94 (d, 1H, J=8.6 Hz), 8.09 (m, 1H), 9.23 (m, 1H).

FAB-MS (m/z); 625 (M)+

The same procedure as in Example 1, Step B, was repeated using 51.2 mg (0.0819 mmol) of diacetylated Compound 154 to give 39.2 mg (88%) of Compound 154.

1H-NMR(CDCl$_3$) δ; 2.18 (s, 3H), 2.74 (dd, 1H, J=4.9, 14.4 Hz), 3.46 (dd, 1H, J=7.5, 14.4 Hz), 3.51 (s, 3H), 4.09 (s, 3H), 4.67 (d, 1H, J=16.4 Hz), 4.75 (s, 2H), 4.78 (d, 1H, J=16.4 Hz), 4.80 (s, 2H), 4.88 (s, 1H), 6.46 (s, 1H), 6.81 (dd, 1H, J=4.9, 7.5 Hz), 7.29 (d, 1H, J=8.3 Hz), 7.39 (m,1H), 7.41 (m, 1H), 7.51 (m, 1H), 7.92 (m, 2H), 8.93 (d, 1H, J=1.0 HZ).

FAB-MS (m/z); 541 (M)+

Example 154
Synthesis of Compound 155

The procedure as in Example 153 was repeated using 49.1 mg (0.0804 mmol) of Compound f to give 24.8 mg (44%) of diacetylated Compound 155.

1H-NMR(CDCl$_3$) δ; 1.81 (s, 3H), 2.17 (dd, 1H, J=5.0, 14.4 Hz), 2.26 (s, 3H), 2.87 (s, 3H), 3.49 (s, 3H),@3.50 (s, 3H), 3.99 (dd, 1H, J=7.5, 14.4 Hz), 4.01 (s, 3H), 4.80 (s, 2H), 4.83 (s, 2H), 4.84 (s, 2H), 4.86 (s, 3H), 5.43 (d, 1H, J=17.6 Hz), 5.48 (d, 1H, J=17.6 Hz), 7.02 (dd, 1H, J=5.0, 7.5 Hz), 7.55 (m, 1H), 7.62 (m, 1H), 7.92 (m, 2H), 8.06 (d, 1H, J=1.2 Hz), 9.23 (d, 1H, J=1.0 Hz).

FAB-MS (m/z); 699 (M)+

The same procedure as in Example 1, Step B, was repeated using 24.8 mg (0.0355 mmol) of diacetylated Compound 155 to give 19.9 mg (71%) of Compound 155.

1H-NMR(CDCl$_3$) δ; 2.20 (s, 3H), 2.45 (dd, 1H, J=4.9, 14.4 Hz), 3.34 (dd, 1H, J=7.5, 14.4 Hz), 3.49 (s, 3H), 3.50 (s, 3H), 3.50 (s, 3H), 4.10 (s, 3H), 4.18 (s, 3H), 4.18 (s, 1H), 4.80 (s, 6H), 4.82 (s, 2H), 4.89 (d, 1H, J=15.8 Hz), 4.96 (d, 1H, J=15.8 Hz), 5.87 (s, 1H), 6.87 (dd, 1H, J=4.9, 7.5 Hz), 7.41 (d, 1H, J=8.6 Hz), 7.49 (m,2H), 7.82 (d, 1H, J=8.8 Hz), 7.90 (d, 1H, J=1.5 Hz), 9.16 (d, 1H, J=1.0 HZ).

FAB-MS (m/z); 615 (M)+

Example 155
Synthesis of Compound 156

The procedure as in Example 153 was repeated using 46.0 mg (0.0753 mmol) of Compound f and 0.02 ml (0.22 mmol) of chloromethyl ethyl ether to give 50.9 mg (94%) of diacetylated Compound 156.

1H-NMR(CDCl$_3$) δ; 1.17 (t, 3H, J=7.1 Hz), 1.19 (t, 3H, J=7.1 Hz), 1.81 (s, 3H), 2.17 (dd, 1H, J=5.1, 14.4 Hz), 2.26 (s, 3H), 2.86 (s, 3H), 3.74 (q, 2H, J=7.1 Hz), 3.75 (q, 2H, J=7.1 Hz), 3.98 (dd, 1H, J=7.3, 14.4 Hz), 4.01 (s, 3H), 4.85 (s, 2H), 4.85 (s, 2H), 4.87 (s, 2H), 4.88 (s, 3H), 5.42 (d, 1H, J=17.6 Hz), 5.47 (d, 1H, J=17.6 Hz), 7.01 (dd, 1H, J=5.1, 7.3 Hz), 7.54 (m, 2H), 7.61 (m, 1H), 7.90 (d, 1H, J=8.6 Hz), 8.05 (d, 1H, J=1.7 Hz), 9.23 (m, 1H).

FAB-MS (m/z); 727 (M)+

The same procedure as in Example 1, Step B, was repeated using 50.9 mg (0.0700 mmol) of diacetylated Compound 156 to give 23.1 mg (51%) of Compound 156.

1H-NMR(CDCl$_3$) δ; 1.30 (t, 6H, J=7.1 Hz), 2.20 (s, 3H), 2.41 (dd, 1H, J=4.9, 14.4 Hz), 3.32 (dd, 1H, J=7.6, 14.4 Hz), 3.73 (q, 2H, J=7.1 Hz), 3.73 (q, 2H, J=7.1 Hz), 4.08 (s, 1H), 4.10 (s, 3H), 4.81 (s, 2H), 4.83 (s, 2H), 4.85 (s, 4H), 4.91 (d, 1H, J=16.8 Hz), 4.98 (d, 1H, J=16.8 Hz), 5.91 (s, 1H), 6.88 (dd, 1H, J=4.9, 7.6 Hz), 7.42 (d, 1H, J=8.3 Hz), 7.49 (m,2H), 7.81 (d, 1H, J=8.5 Hz), 7.90 (d, 1H, J=1.2 Hz), 9.18 (d, 1H, J=1.0 Hz).

FAB-MS (m/z); 643 (M)+

Example 156
Synthesis of Compound 157

To a solution of 45.0 mg (0.0854 mmol) of Compound h in 2 ml of dichloromethane was added 0.1 ml (1.3 mmol) of 2-methoxyethanol and 36.2 mg (0.156 mmol) of (±) 10-camphorsulfonic acid, and the mixture was stirred at room temperature for 2 days. After addition of saturated aqueous solution of sodium bicarbonate, the reaction mixture was extracted with chloroform. The organic layer was washed with a saturated aqueous solution of sodium chloride and dried over sodium sulfate. The solvent was evaporated under reduced pressure, and the residue was purified by preparative TLC (chloroform/methanol=95/5) to give 19.9 mg (36%) of Compound 157.

1H-NMR(CDCl$_3$) δ; 2.19 (s, 3H), 2.42 (dd, 1H, J=4.6, 14.3 Hz), 3.32 (dd, 1H, J=7.2, 14.3 Hz), 3.41 (s, 3H), 3.43 (s, 3H), 3.60–3.64 (m, 4H), 4.09 (s, 3H), 4.17 (br, 1H), 4.77 (s, 2H), 4.80 (s, 2H), 4.89 (d, 1H, J=16.6 Hz), 4.97 (d, 1H, J=16.6 Hz), 5.95 (br, 1H), 6.87 (dd, 1H, J=4.6, 7.2 Hz), 7.43 (d, 1H, J=8.5 Hz), 7.47 (m, 1H), 7.53 (d, 1H, J=8.5 Hz), 7.85 (d, 1H, J=8.5 Hz), 7.91 (s, 1H), 9.10 (s, 1H).

FAB-MS (m/z); 643 (M)+

Reference Example 1
Synthesis of Compound A

To a solution of 5.00 g (9.07 mmol) of Compound c (Japanese Published Unexamined Patent Application No. 295588/88) in 100 ml of a 10% methanol/chloroform mixture was added 1.62 g (9.10 mmol) of N-bromosuccinimide under ice cooling, followed by stirring at room temperature for 8.5 hours. The precipitated crystals were separated by filtration and dried to give 3.59 g (63%) of Compound A.

$^1$H-NMR (CDCl$_3$) δ; 1.82 (s, 3H), 2.18 (dd, 1H, J=5.1, 14.5 Hz), 2.30 (s, 3H), 2.83 (s, 3H), 4.00 (dd, 1H, J=7.5, 14.5 Hz), 4.03 (s, 3H), 5.40 (d, 1H, J=17.5 Hz), 5.44 (d, 1H, J=17.5 Hz), 6.98 (dd, 1H, J=5.1, 7.5 Hz), 7.44 (d, 1H, J=8.7 Hz), 7.47 (m, 1H), 7.57 (m, 1H), 7.64 (dd, 1H, J=2.0, 8.7 Hz), 7.96 (d, 1H, J=8.4 Hz), 8.10 (m, 1H), 9.39 (d, 1H, J=2.0 Hz).

FAB-MS (m/z); 630 (M)+, 632 (M+2)+

Reference Example 2
Synthesis of Compound B

A solution of 501 mg (0.794 mmol) of Compound A and 111 mg (0.792 mmol) of hexamethylenetetramine in 5 ml of trifluoroacetic acid was stirred under reflux for 4 hours, followed by addition of water. Resulting insoluble materials were collected by filtration, purified by silica gel column chromatography (chloroform/methanol=99/1) and then by methanol trituration to give 296 mg (57%) of Compound B.

$^1$H-NMR (DMSO-d$_6$) δ; 1.70 (s, 3H), 2.25 (s, 3H), 2.32 (dd, 1H, J=5.0, 14.8 Hz), 2.68 (s, 3H), 3.90 (dd, 1H, J=7.5, 14.8 Hz), 3.96 (s, 3H), 5.44 (d, 1H, J=17.7 Hz), 5.49 (d, 1H, J=17.7 Hz), 7.35 (dd, 1H, J=5.0, 7.5 Hz), 7.69 (m, 1H), 8.05 (d, 1H, J=8.8 Hz), 8.13 (m, 1H), 8.21 (d, 1H, J=8.7 Hz), 8.67 (m, 1H), 9.24 (d, 1H, J=1.9 Hz), 10.24 (s, 1H).

FAB-MS (m/z); 658 (M)$^+$, 660 (M+2)$^+$

Reference Example 3
Synthesis of Compound C

Compound B (237 mg, 0.360 mmol), 64.2 mg (0.0556 mmol) of tetrakis(triphenylphosphine) palladium and 44.6 mg (0.454 mmol) of potassium acetate were dissolved in 2 ml of N,N-dimethylformamide, and the solution was stirred at 100° C. for 2 hours. To the reaction mixture was added water, followed by extraction with chloroform. The extract was washed with a saturated aqueous solution of sodium chloride, and dried over anhydrous sodium sulfate. After evaporation of the solvent under reduced pressure, the residue was purified by silica gel column chromatography (chloroform/methanol=99/1) to give 71.2 mg (34%) of Compound C.

$^1$H-NMR (CDCl$_3$) δ; 1.79 (s, 3H), 2.15 (dd, 1H, J=5.1, 14.7 Hz), 2.25 (s, 3H), 2.71 (s, 3H), 4.00 (dd, 1H, J=7.7, 14.7 Hz), 4.02 (s, 3H), 5.30 (s, 2H), 7.02 (dd, 1H, J=5.1, 7.7 Hz), 7.34 (m, 1H), 7.54 (m, 2H), 8.01 (d, 1H, J=8.8 Hz), 8.08 (m, 1H), 9.43 (d, 1H, J=1.2 Hz), 9.16 (d, 1H, J=8.1 Hz), 10.19 (s, 1H).

FAB-MS (m/z); 580 (M+1)$^+$

Reference Example 4
Synthesis of Compound D

To a solution of 1.02 g of Compound c (Japanese Published Unexamined Patent Application No. 295588/88) in 50 ml of 1,2-dichloroethane was added dropwise 0.17 ml of fuming nitric acid, and the mixture was stirred at room temperature for 10 minutes. A saturated aqueous solution of sodium hydrogen carbonate was added to the reaction mixture, followed by extraction with chloroform. The extract was washed with a saturated aqueous solution of sodium chloride, and dried over anhydrous magnesium sulfate. After evaporation of the solvent under reduced pressure, the residue was purified by silica gel column chromatography (chloroform/methanol=99/1) to give 537 mg (49%) of Compound D.

$^1$H-NMR (CDCl$_3$) δ; 1.82 (s, 3H), 2.26 (dd, 1H, J=5.4, 14.6 Hz), 2.31 (s, 3H), 2.70 (s, 3H), 4.03 (s, 3H), 4.07 (dd, 1H, J=7.5, 14.6 Hz), 5.38 (s, 2H), 6.99 (dd, 1H, J=5.4, 7.5 Hz), 7.48–7.59 (m, 3H), 7.96–8.08 (m, 2H), 8.03 (m, 1H), 10.02 (s, 1H).

FAB-MS (m/z); 597 (M+1)$^+$

Reference Example 5
Synthesis of Compound E

A solution of 50.0 mg (0.0839 mmol) of Compound D and 175 mg (1.25 mmol) of hexamethylenetetramine in 1 ml of trifluoroacetic acid was stirred under reflux for 2 hours. After addition of water, the reaction mixture was neutralized with a saturated aqueous solution of sodium hydrogen carbonate, followed by extraction with chloroform. The extract was washed with a saturated aqueous solution of sodium chloride, and dried over anhydrous sodium sulfate. Evaporation of the solvent under reduced pressure gave Compound E.

$^1$H-NMR (CDCl$_3$) δ; 1.83 (s, 3H), 2.29 (dd, 1H, J=5.3, 14.7 Hz), 2.34 (s, 3H), 2.64 (s, 3H), 4.05 (s, 3H), 4.12 (dd, 1H, J=7.5, 14.7 Hz), 5.34 (d, 1H, J=17.6 Hz), 5.40 (d, 1H, J=17.6 Hz), 7.02 (dd, 1H, J=5.3, 7.5 Hz), 7.54 (d, 1H, J=9.3 Hz), 8.07 (d, 1H, J=8.6 Hz), 8.15 (m, 1H), 8.37 (m, 1H), 8.50 (d, 1H, J=1.5 Hz), 8.90 (d, 1H, J=2.2 Hz), 10.24 (s, 1H).

FAB-MS (m/z); 625 (M+1)$^+$

Reference Example 6
Synthesis of Compound F

Methanol (3 ml) was added to 1.4 g (60–65%, ca. 2.6 mmol) of mercury (II) nitrate monohydrate, followed by stirring at room temperature for 5 minutes. To the mixture were successively added a solution of 551 mg (1.0 mmol) of Compound c (Japanese Published Unexamined Patent Application No. 295588/88) in 12 ml of chloroform and 660 mg (2.6 mmol) of iodine, and the resulting mixture was stirred at room temperature for one hour. The reaction mixture was poured into 150 ml (1 N) of an aqueous solution of sodium thiosulfate, followed by extraction with chloroform. The extract was washed with water, and dried over anhydrous sodium sulfate. After evaporation of the solvent under reduced pressure, the residue was purified by silica gel column chromatography (chloroform) to give 750 mg (93%) of Compound F.

$^1$H-NMR (CDCl$_3$) δ; 2.14 (s, 3H), 3.00 (dd, 1H, J=4.6, 14.5 Hz), 3.72 (dd, 1H, J=4.6, 7.6 Hz), 4.09 (s, 3H), 4.31 (d, 1H, J=16.6), 4.59 (d, 1H, J=16.6 Hz), 5.39 (br, 1H), 5.54 (br, 1H), 6.78 (dd, 1H, J=6.0,7.6 Hz), 7.13 (d, 1H, J=8.5 Hz), 7.45 (dd, 1H, J=1.7, 8.5 Hz), 7.72(d, 1H, J=8.7 Hz), 7.76 (dd, 1H, J=1.7, 8.7 Hz), 8.16 (d, 1H, J=1.5 Hz), 8.83 (d, 1H, J=1.0 Hz).

FAB-MS (m/z); 804 (M+1)$^+$

Reference Example 7
Synthesis of Compound G

The same procedure as in Reference Example 6 was repeated using 23.4 mg (0.05 mmol) of K-252a to give 11 mg (86%) of Compound G.

$^1$H-NMR (CDCl$_3$) δ; 1.80 (s, 3H), 2.11 (dd, 1H, J=7.3, 16.2 Hz), 2.24 (s, 3H), 2.79 (s, 3H), 3.97 (dd, 1H, J=7.3, 9.3 Hz), 4.00 (s, 3H), 5.32 (m, 2H), 6.93 (dd, 1H, J=2.7, 7.6 Hz), 7.27 (m, 1H), 7.68 (d, 1H, J=8.8 Hz), 7.78 (m, 2H), 8.32 (br, 1H), 9.52 (br, 1H).

FAB-MS (m/z); 720 (M+1)$^+$

Example 157
Spinal Cord ChAT Activity Assay

The effect of selected ring substituted K-252a derivatives on ChAT activity was assayed in dissociated spinal cord cultures prepared from fetal rats using the procedure described in U.S. Pat. No. 5,461,146, Columns 26 and 27, Examples 6 and 7. ChAT is the enzyme that catalyzes the synthesis of the neurotransmitter acetylcholine, and it is a specific biochemical marker for cholinergic neurons. In the spinal cord, the large majority of cholinergic neurons are motor neurons. Assay of this enzyme may thus be used as an indication of the effects of a factor, or factors, on the survival of cholinergic neurons and/or regulation of this enzyme.

The compounds were tested at 3 nM and 300 nM, and the data are summarized Table 3. Compounds which increased ChAT activity at least 120% of the control activity are considered active.

TABLE 3

Spinal Cord ChAT Activity

| Compound # | ChAT Activity maximum efficacy % of Control (conc) |
|---|---|
| 1 | 153 (30 nM) |
| 2 | 149 (300 nM) |
| 3 | 134 (300 nM) |
| 4 | 183 (300 nM) |
| 5 | 242 (300 nM) |
| 6 | 149 (2000 nM) |
| 7 | 186 (300 nM) |
| 8 | 150 (300 nM) |
| 9 | <120 |
| 10 | 164 (300 nM) |
| 11 | 236 (300 nM) |
| 12 | 269 (300 nM) |
| 13 | 271 (30 nM) |
| 14 | 282 (300 nM) |
| 16 | 159 (300 nM) |
| 18 | 270 (300 nM) |
| 19 | 228 (300 nM) |
| 20 | 157 (300 nM) |
| 21 | 249 (30 nM) |
| 22 | 258 (100 nM) |
| 23 | 233 (100 nM) |
| 34 | <120 |
| 41 | 204 (300 nM) |
| 42a | 151 (300 nM) |
| 44 | <120 |
| 47 | <120 |
| 52 | <120 |
| 54 | <120 |
| 59 | 160 (300 nM) |
| 62 | 235 (300 nM) |
| 68 | 291 (300 nM) |
| 70b | 169 (300 nM) |
| 70c | 186 (300 nM) |
| 71 | 193 (300 nM) |
| 81 | 131 (300 nM) |
| 87 | 294 (300 nM) |
| 88 | 190 (300 nM) |
| 91 | <120 |
| 92 | 210 (300 nM) |
| 94 | 152 (300 nM) |
| 95 | 272 (300 nM) |
| 116 | 231 (30 nM) |
| 117 | 232 (30 nM) |
| 118 | 249 (30 nM) |
| 119 | 272 (30 nM) |
| 120 | 257 (300 nM) |
| 122 | 279 (300 nM) |
| 139 | <120 |
| 140 | 156 (300 nM) |
| 142 | 223 (300 nM) |
| 143 | 264 (300 nM) |
| 145 | 129 (300 nM) |
| 146 | 153 (300 nM) |
| 148 | 206 (300 nM) |
| 154 | 177 (300 nM) |
| 155 | 197 (300 nM) |
| 156 | 217 (300 nM) |

Example 158
Basal Forebrain ChAT Activity Assay

Compounds of the invention were assessed for their ability to promote survival and increase in ChAT activity in the basal forebrain cultures. ChAT activity in these cultures is a biochemical marker for the cholinergic neurons (less than 5% of the cells in culture), which represent the major cholinergic input to the hippocampal formation, olfactory nucleus, interpeduncular nucleus, cortex, amygdala, and parts of the thalamus. Representative compounds of the invention not only increased ChAT activity but in addition increased general survival of neurons in basal forebrain cultures.

The basal forebrain was dissected from embryonic day 17 or 18 rat embryos and the cells were dissociated with Dispase™ (neutral protease, Collaborative Research). Neurons were plated at $5 \times 10^4$ cells/well ($1.5 \times 10^5$ cells/cm$^2$) in wells of 96-well plates previously coated with poly-1-ornithine and laminin. Cells were cultured in serum-free $N_2$ medium containing 0.05% bovine serum albumin (BSA) (Bottenstein et al., supra) at 37° in a humidified atmosphere of 5% $CO_2$/95% air. ChAT activity was measured in vitro at day six, using a modification of the Fonnum procedure (supra) according to McManaman et al. (supra) and Glicksman et al. (*J. Neurochem,* 61:210–221, 1993).

The compounds were tested at concentrations between 10 nM and 500 nM, and the data are summarized in Table 4. Compounds which increased ChAT activity at least 120% of the control activity are considered active.

TABLE 4

Basal Forebrain ChAT Activity

| Compound # | ChAT Activity maximum efficacy % of Control (conc) |
|---|---|
| 7 | <120 |
| 8 | 144 (100 nM) |
| 11 | 149 (250 nM) |
| 12 | 184 (500 nM) |
| 13 | 167 (100 nM) |
| 14 | 229 (500 nM) |
| 16 | 143 (100 nM) |
| 18 | 148 (250 nM) |
| 19 | 172 (100 nM) |
| 20 | 176 (500 nM) |
| 21 | 171 (50 nM) |
| 22 | 174 (50 nM) |
| 23 | 134 (50 nM) |
| 34 | 145 (500 nM) |
| 41 | <120 |
| 42a | 246 (250 nM) |
| 42b | 164 (250 nM) |
| 44 | <120 |
| 45 | <120 |
| 46 | <120 |
| 47 | <120 |
| 48 | <120 |
| 49 | <120 |
| 52 | <120 |
| 54 | 167 (250 nM) |
| 59 | 131 (250 nM) |
| 61 | 166 (50 nM) |
| 62 | 202 (50 nM) |
| 64 | 165 (250 nM) |
| 68 | 290 (250 nM) |
| 70a | <120 |
| 70b | 239 (250 nM) |
| 70c | 203 (250 nM) |
| 71 | 152 (250 nM) |
| 73b | 171 (250 nM) |
| 73c | 190 (250 nM) |
| 75 | <120 |
| 76 | <120 |
| 77 | 132 (250 nM) |
| 78 | <120 |
| 79 | <120 |
| 80 | <120 |
| 81 | <120 |
| 82 | 150 (250 nM) |
| 83 | <120 |
| 84 | <120 |
| 87 | 262 (250 nM) |
| 88 | <120 |
| 89 | <120 |
| 90 | <120 |
| 91 | <120 |
| 92 | 311 (250 nM) |
| 93 | <120 |

TABLE 4-continued

Basal Forebrain ChAT Activity

| Compound # | ChAT Activity maximum efficacy % of Control (conc) |
|---|---|
| 94 | 166 (250 nM) |
| 95 | 239 (250 nM) |
| 96 | <120 |
| 99 | 136 (50 nM) |
| 102 | 176 (50 nM) |
| 103 | 154 (50 nM) |
| 104 | <120 |
| 105 | 136 (50 nM) |
| 106 | 135 (250 nM) |
| 107 | <120 |
| 108 | <120 |

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention. Documents cited throughout this patent disclosure are hereby incorporated herein by reference.

What is claimed is:

1. A compound defined by the general formula (I):

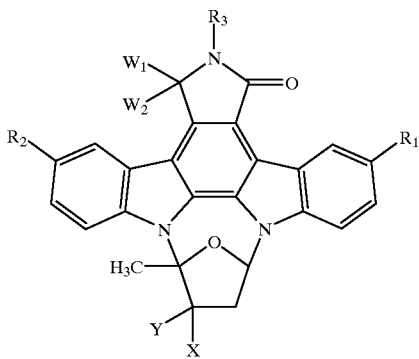

wherein:
one $R^1$ or $R^2$ is selected from $CO(CH_2)_j R^4$, $CH(OH)(CH_2)_b R^{4A}$, $(CH_2)_k R^7$, $C{\equiv}C(CH_2)_n R^{13}$, $HC{=}CH(CH_2)_m R^{12}$, $HC{=}CH(CO_2 R^{33})_2$, $CO(CH_2)_j SR^{27}$, $CH_2 OR^{44}$, $CH_2 CHR^{31} CO_2 R^{32}$, and CHO;

the other $R^1$ or $R^2$ is selected from hydrogen, lower alkyl, halogen, nitro, $NR^{14}R^{15}$, $CH_2 SR^{37}$, $CO(CH_2)_q R^{16}$, $CH(OH)(CH_2)_r R^{38}$, $(CH_2)_t R^{17}$, $HC{=}CH(CH_2)_n R^{18}$, $C{\equiv}C(CH_2)_u R^{19}$, $CO(CH_2)_q SR^{37}$, CHO, $CH(SR^{34})_2$, $CH_2 CHR^{39} CO_2 R^{40}$, and $CH_2 OR^{36}$;

$R^4$ and $R^{16}$ are selected from halogen, $OR^{29}$, and $NR^5 R^6$;

$R^{4A}$ and $R^{38}$ are selected from hydrogen, halogen and $NR^5 R^6$;

$R^5$ and $R^6$ are selected from hydrogen, lower alkyl, and phenyl; or $R^5$ and $R^6$ are combined with a nitrogen atom to form piperidine, morpholine, tetrahydropyrrole or piperazine;

$R^7$ and $R^{17}$ are selected from halogen, phenyl, pyridyl, piperidinyl, morpholinyl, imidazolyl, OC(=O)H, $OR^9$, $NR^{10}R^{11}$, $CO_2 R^8$, $N_3$, and $SR^{27}$;

$R^8$ is selected from hydrogen, lower alkyl, phenyl, and pyridyl;

$R^9$ is selected from hydrogen, pyridylcarbonyl, and lower alkyl;

$R^{10}$ and $R^{11}$ are selected from hydrogen, lower alkyl, hydroxyalkyl, phenyl, benzyl, methoxybenzyl, lower alkyloxycarbonyl, and lower alkylaminocarbonyl; or $R^{10}$ and $R^{11}$ combine together to form piperidine, morpholine, tetrahydropyrrole or piperazine;

$R^{12}$ and $R^{18}$ are selected from hydrogen, lower alkyl, phenyl, pyridyl, imidazolyl, $CO_2 R^8$, and $NR^{10}R^{11}$;

$R^{13}$ and $R^{19}$ are selected from hydrogen, lower alkyl, $NR^{10}R^{11}$, and $OR^9$;

$R^{14}$ and $R^{15}$ are independently selected from hydrogen, lower alkyl, and lower alkylaminocarbonyl;

$R^{27}$ and $R^{37}$ are selected from hydrogen, lower alkyl, hydroxyalkyl, phenyl, hydroxyphenyl, pyridyl, pyrimidine, thiazolinyl, benzothiazolyl, alkyltetrazole, benzimidazole, $(CH_2)_2 NMe_2$, and $(CH_2)_a CO_2 R^{28}$;

$R^{28}$, $R^{29}$, $R^{32}$, $R^{33}$, and $R^{40}$ are selected from hydrogen and lower alkyl;

$R^{31}$ and $R^{39}$ are selected from hydrogen and $CO_2 R^{33}$;

$R^{34}$ is lower alkyl;

$R^{36}$ is selected from hydrogen, $(CH_2)_2 NMe_2$, methoxymethyl, ethoxymethyl, methoxyethyl, and ti-lower alkylsilyl in which the three lower alkyl groups are the same or different;

$R^{44}$ is selected from hydrogen, $(CH_2)_2 NMe_2$, methoxymethyl, ethoxymethyl, and methoxyethyl;

a, b, and e are each 1 or 2;

k and r are each 2, 3 or 4;

m, n, t, and u are each 0 or 1;

j and q are each 1, 2, 3, or 4;

$R^3$ is selected from hydrogen, acetyl, and lower alkyl;

X is selected from hydrogen, hydroxymethyl, lower alkoxycarbonyl, and $CONR^{20}R^{21}$;

$R^{20}$ and $R^{21}$ are independently selected from hydrogen and lower alkyl;

Y is selected from hydroxy, lower alkoxy, aralkyloxy, and acyloxy; and each $W^1$ and $W^2$ is hydrogen or together represent oxygen.

2. The compound of claim 1, wherein $R^3$ is selected from hydrogen and acetyl, X is selected from hydroxymethyl and lower alkoxycarbonyl, Y is selected from hydroxy and acetyloxy, and $W^1$ and $W^2$ are hydrogen.

3. The compound of claim 2 wherein X is selected from hydroxymethyl and methoxycarbonyl, Y is hydroxy, and $R^3$ is hydrogen.

4. The compound of claim 2 wherein:
one of $R^1$ and $R^2$ is selected from:
methoxycarbonylvinyl, ethoxycarbonylvinyl, styryl, 2-pyridylvinyl, 4-pyridylvinyl, 2-pyridylethyl, 4-pyridylethyl, phenylethyl, methoxypropynyl, hydroxypropynyl, $COCH_2 SEt$, $C{\equiv}CCH_2 NMeBn$, $CH{=}CHEt$, $(CH2)_2 SMe$, $(CH_2)_2 S$-2-thiazoline, $(CH_2)_3 SMe$, $CH_2 OMe$, $CH{=}CH$-2-imidazole, $(CH_2)_2 OC(=O)H$, methoxymethoxymethyl, ethoxymethoxymethyl, methoxyethoxymethyl, and 2-hydroxyethyl; and the other of $R^1$ and $R^2$ is selected from:
hydrogen, halogen, methoxycarbonylvinyl, ethoxycarbonylvinyl, styryl, 2-pyridylvinyl, 4-pyridylvinyl, 2-pyridylethyl, 4-pyridylethyl, phenylethyl, nitro, amino, N-ethylurea, methoxypropynyl, hydroxypropynyl, COCH$_2$SEt, C≡CCH$_2$NMeBn, CH=CHEt, (CH$_2$)$_2$SMe, (CH$_2$)$_2$S-2-thiazoline, (CH$_2$)$_3$SMe, CH$_2$OMe, CH$_2$OEt, CH$_2$SEt, pyridylthiomethyl, —CH$_2$S-2-benzmidazole, CH=CHEt, CH=CH-2-imidazole, (CH$_2$)$_2$OC(=O)H, methoxymethoxymethyl, ethoxymethoxymethyl, methoxyethoxymethyl, and 2-hydroxyethyl.

\* \* \* \* \*

UNITED STATES PATENT AND TRADEMARK OFFICE
CERTIFICATE OF CORRECTION

PATENT NO. : 6,306,849 B1
DATED : October 23, 2001
INVENTOR(S) : Robert L. Hudkins et al.

It is certified that error appears in the above-identified patent and that said Letters Patent is hereby corrected as shown below:

<u>Title page,</u>
Item [73], Assignee, please add -- and Kyowa Hakko Kogyo Co., Ltd., Tokyo (Japan) -- after "West Chester, PA (US)".

Item [63], please add -- , now abandoned -- after "Jun. 3, 1996".

Item [56], OTHER PUBLICATIONS,
At Hirata et al., third line thereof, please delete "XP00204135" and insert -- XP002041235 -- therefor.
At Borasio, second line thereof, please delete "in vivo" and insert -- in vitro -- therefor.
At Dunnett S. et al., second line thereof, please delete "interpeting" and insert -- interpreting -- therefor.
At Glicksman, M. et al., second line thereof, please delete "Acetyltransference" and insert -- Acetyltransferase -- therefor.
At Kase et al., second line thereof, please delete "Orgin" and insert -- Origin -- therefor.
At Knüet al., please delete "Knüet al." and insert -- Knüesel et al. -- therefor.
At McManamann, J. et al., second line thereof, please delete "Polypeptides" and insert -- Polypeptide -- therefor.
At Ohno et al., third line thereof, please delete "ot" and insert -- to -- therefor.
At Olton, D. et al., second line thereof, please delete "*Psychopharmcology*" and insert -- *Psychopharmacology* -- therefor.
At Slack et al., third line thereof, please delete "Line" and insert -- Lines -- therefor.

Please delete "Containing Them, Chemical Abstracts 111:728, XP002041235 see abstract and 12$^{th}$ Collective Chemical Substance Index, p. 34237, c. 3 (5-7, 55-60, 66-69), p. 34238, c.1 (41-44), c.2 (25-27, 32-33), p. 3423, c.3 (48-50, 52-53). (No date)."

<u>Column 1,</u>
Line 3, please add -- , now abandoned -- after "Jun. 3, 1996".

<u>Column 5,</u>
Line 11, please delete "allyl" and insert -- alkyl -- therefor.
Line 34, please delete "allyl" and insert -- alkyl -- therefor.
Line 43, please delete "alkyl the lower alkoxy" and insert -- alkyl, the lower alkoxy -- therefor.

<u>Column 6,</u>
Line 24, please delete "vales" and insert -- values -- therefor.
Line 60, please delete "neuror" and insert -- neuron -- therefor.

UNITED STATES PATENT AND TRADEMARK OFFICE
CERTIFICATE OF CORRECTION

PATENT NO. : 6,306,849 B1
DATED : October 23, 2001
INVENTOR(S) : Robert L. Hudkins et al.

It is certified that error appears in the above-identified patent and that said Letters Patent is hereby corrected as shown below:

Column 7,
Line 13, please delete "forebran" and insert -- forebrain -- therefor.
Line 21, please delete "non-neurona cell" and insert -- non-neuronal cells -- therefor.
Line 41, please delete "associate" and insert -- associated -- therefor.
Line 50, please delete "cackling" and insert -- calcium -- therefor.

Column 19,
Line 13, please delete "methylsulfonyoxy" and insert -- methylsulfonyloxy -- therefor.
Line 14, please delete "nucleophllic" and insert -- nucleophilic -- therefor.

Column 28,
Line 15, please delete "(n 1H)" and insert -- (m 1H) -- therefor.
Line 33, please delete "2-pyridmemethyl-" and insert -- 2-pyridenemethyl- -- therefor.

Column 29,
Line 53, please delete "chromate by" and insert -- chromatography -- therefor.

Column 30,
Line 54, please delete "diacetlated" and insert -- diacetylated -- therefor.

Column 31,
Line 11, please delete "The re" and insert -- The mixture -- therefor.

Column 32,
Line 37, please delete "diacylated" and insert -- diacetylated -- therefor.

Column 33,
Line 13, please delete "chromatrography" and insert -- chromatography -- therefor.

Column 36,
Line 4, please delete "by on" and insert -- by extraction -- therefor.

Column 37,
Line 45, please delete "Comnpound" and insert -- Compound -- therefor.

Column 39,
Line 46, please delete "e ion" and insert -- extraction -- therefor.

Column 41,
Line 64, please delete "7.5" and insert -- 7.58 -- therefor.

UNITED STATES PATENT AND TRADEMARK OFFICE
CERTIFICATE OF CORRECTION

PATENT NO.    : 6,306,849 B1
DATED         : October 23, 2001
INVENTOR(S)   : Robert L. Hudkins et al.

It is certified that error appears in the above-identified patent and that said Letters Patent is hereby corrected as shown below:

Column 42,
Line 17, please delete "red" and insert -- repeated -- therefor.
Line 62, please delete "13.7 H" and insert -- 13.7Hz -- therefor.

Column 43,
Line 45, please delete "was the" and insert -- was then -- therefor.

Column 44,
Line 15, please delete "was the" and insert -- was then -- therefor.
Line 18, please delete "sated" and insert -- saturated -- therefor.
Line 31, please delete "was the" and insert -- was then -- therefor.

Column 45,
Line 63, please delete "6.33 (s, 1)" and insert -- 6.33 (s, 1H) -- therefor.

Column 46,
Line 10, please delete "hu 1H-NMR" and insert -- $^{1}$H NMR -- therefor.

Column 47,
Line 19, please delete "hu 1H-NMR" and insert -- $^{1}$H NMR -- therefor.
Line 59, please delete "hu 1H-NMR" and insert -- $^{1}$H NMR -- therefor.

Column 54,
Line 38, please delete "exact" and insert -- extract -- therefor.
Line 51, please delete "1H, =0.4" and insert -- 1H, J=0.4 -- therefor.

Column 58,
Line 55, please delete "sure" and insert -- mixture -- therefor.

Column 64,
Line 45, please delete "stature" and insert -- saturated -- therefor.

Column 68,
Line 65, please delete "summarrized Table 3." and insert -- summarized in Table 3. -- therefor.

UNITED STATES PATENT AND TRADEMARK OFFICE
CERTIFICATE OF CORRECTION

PATENT NO.      : 6,306,849 B1
DATED           : October 23, 2001
INVENTOR(S)     : Robert L. Hudkins et al.

It is certified that error appears in the above-identified patent and that said Letters Patent is hereby corrected as shown below:

Column 72,
Line 28, please delete "ti-lower" and insert -- tri-lower -- therefor.

Column 74,
Line 1, please delete "benzmidazole" and insert -- benzimidazole -- therefor.

Signed and Sealed this

Twenty-second Day of April, 2003

JAMES E. ROGAN
*Director of the United States Patent and Trademark Office*